United States Patent
Woollam et al.

(10) Patent No.: US 7,633,625 B1
(45) Date of Patent: *Dec. 15, 2009

(54) SPECTROSCOPIC ELLIPSOMETER AND POLARIMETER SYSTEMS

(75) Inventors: John A. Woollam, Lincoln, NE (US); Blaine D. Johs, Lincoln, NE (US); Craig M. Herzinger, Lincoln, NE (US); Ping He, Lincoln, NE (US); Martin M. Liphardt, Lincoln, NE (US); Galen L. Pfeiffer, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 283 days.

This patent is subject to a terminal disclaimer.

(21) Appl. No.: 11/901,225

(22) Filed: Sep. 17, 2007

Related U.S. Application Data

(63) Continuation-in-part of application No. 11/497,921, filed on Aug. 3, 2006, now Pat. No. 7,489,400, which is a continuation-in-part of application No. 10/613,051, filed on Jul. 7, 2003, now Pat. No. 7,099,006, application No. 11/901,225, and a continuation-in-part of application No. 09/945,962, filed on Sep. 4, 2001, now Pat. No. 7,075,649, which is a continuation-in-part of (Continued)

(60) Provisional application No. 60/229,755, filed on Sep. 5, 2000, provisional application No. 60/473,615, filed on Aug. 27, 2004, provisional application No. 60/473,616, filed on May 28, 2003, provisional application No. 60/553,032, filed on Mar. 15, 2004, provisional application No. 60/517,566, filed on Nov. 6, 2003, provisional application No. 60/572,204, filed on May 18, 2004, provisional application No. 60/527,554, filed on Dec. 6, 2003, provisional application No. 60/527,638, filed on Dec. 8, 2003, provisional application No. 60/576,466, filed on Jun. 3, 2004, provisional application No. 60/498,479, filed on Aug. 28, 2003, provisional application No. 60/424,589, filed on Nov. 7, 2002, provisional application No. 61/611,173, filed on Sep. 17, 2004, provisional application No. 60/749,768, filed on Dec. 13, 2005.

(51) Int. Cl.
G01B 9/02 (2006.01)
G01J 3/45 (2006.01)
G01J 4/00 (2006.01)

(52) U.S. Cl. .................... 356/451; 356/369

(58) Field of Classification Search ............ 356/369, 356/450, 497, 498, 503, 504
See application file for complete search history.

(56) References Cited

U.S. PATENT DOCUMENTS 2,447,828 A 8/1948 West (Continued)

Primary Examiner—Michael A Lyons
(74) Attorney, Agent, or Firm—James D. Welch

(57) ABSTRACT

A rotating compensator spectroscopic ellipsometer or polarimeter system having a source of a polychromatic beam of electromagnetic radiation, a polarizer, a stage for supporting a material system, an analyzer, a dispersive optics and a detector system which comprises a multiplicity of detector elements, the system being functionally present in an environmental control chamber and therefore suitable for application in wide spectral range, (for example, 130-1700 nm). Preferred compensator design involves a substantially achromatic multiple element compensator systems wherein multiple total internal reflections enter retardance into an entered beam of electromagnetic radiation, and the elements thereof are oriented to minimize changes in the net retardance vs. the input beam angle resulting from changes in the position and/or rotation of the system of elements.

2 Claims, 30 Drawing Sheets

Related U.S. Application Data application No. 09/517,125, filed on Feb. 29, 2000, now abandoned, and a continuation-in-part of application No. 09/246,888, filed on Feb. 8, 1999, now Pat. No. 6,084,675, and a continuation-in-part of application No. 09/232,257, filed on Jan. 19, 1999, now Pat. No. 6,141,102, and a continuation-in-part of application No. 09/225,118, filed on Jan. 4, 1999, now Pat. No. 6,084,674, and a continuation-in-part of application No. 09/223,822, filed on Jan. 4, 1999, now Pat. No. 6,118,537, and a continuation-in-part of application No. 09/225,371, filed on Jan. 4, 1999, now Pat. No. 6,100,981, and a continuation-in-part of application No. 09/225,076, filed on Jan. 4, 1999, now Pat. No. 5,963,325, said application No. 09/246,888 is a continuation-in-part of application No. 08/912,211, filed on Aug. 15, 1997, now Pat. No. 5,872,630, and a continuation-in-part of application No. 08/618,820, filed on Mar. 20, 1996, now Pat. No. 5,706,212, which is a continuation-in-part of application No. 08/530,892, filed on Sep. 20, 1995, now Pat. No. 5,666,201, application No. 11/901,225, and a continuation-in-part of application No. 11/585,301, filed on Oct. 23, 2006, now Pat. No. 7,518,725, which is a continuation-in-part of application No. 10/928,429, filed on Aug. 27, 2004, now Pat. No. 7,317,529, which is a continuation-in-part of application No. 10/829,620, filed on Apr. 22, 2004, now Pat. No. 7,193,710, and a continuation-in-part of application No. 10/699,540, filed on Nov. 1, 2003, now Pat. No. 7,158,231, and a continuation-in-part of application No. 10/425,801, filed on Apr. 29, 2003, now Pat. No. 6,930,813, and a continuation-in-part of application No. 10/034,800, filed on Oct. 28, 2001, now Pat. No. 6,822,738, and a continuation-in-part of application No. 09/583,229, filed on May 30, 2000, now Pat. No. 6,804,004, and a continuation-in-part of application No. 08/912,211, filed on Aug. 15, 1997, now Pat. No. 5,872,630, and a continuation-in-part of application No. 08/530,892, filed on Sep. 20, 1995, now Pat. No. 5,666,201, application No. 11/901,225, which is a continuation-in-part of application No. 11/084,827, filed on Mar. 21, 2005, now Pat. No. 7,301,631.

U.S. PATENT DOCUMENTS

| Patent No. | Date | Inventor | Class |
|---|---|---|---|
| 3,817,624 A | 6/1974 | Martin | |
| 4,053,232 A | 10/1977 | Dill et al. | 356/118 |
| 4,054,812 A | 10/1977 | Lessner et al. | 313/44 |
| 4,176,951 A | 12/1979 | Robert et al. | 356/33 |
| 4,179,217 A | 12/1979 | Robert et al. | 356/33 |
| 4,322,165 A | 3/1982 | Ellenbracht et al. | 356/316 |
| 4,556,292 A | 12/1985 | Mathyssek et al. | 350/394 |
| 4,668,086 A | 5/1987 | Redner | 356/33 |
| 4,764,013 A | 8/1988 | Johnston | 356/484 |
| 4,770,895 A | 9/1988 | Hartley | 427/10 |
| 4,772,104 A | 9/1988 | Buhrer | 350/403 |
| 4,875,773 A | 10/1989 | Burns et al. | 356/328 |
| 4,917,461 A | 4/1990 | Goldstein | 350/286 |
| 4,961,634 A | 10/1990 | Chipman et al. | 350/403 |
| 5,091,320 A | 2/1992 | Aspnes et al. | 437/8 |
| 5,166,752 A | 11/1992 | Spanier et al. | 356/369 |
| 5,229,833 A | 7/1993 | Stewart | 356/364 |
| 5,329,357 A | 7/1994 | Bernoux et al. | 356/369 |
| 5,337,146 A | 8/1994 | Azzam | 356/367 |
| 5,373,359 A | 12/1994 | Woollam et al. | 356/328 |
| 5,475,525 A | 12/1995 | Tournois et al. | 359/245 |
| 5,504,582 A | 4/1996 | Johs et al. | 356/369 |
| 5,521,706 A | 5/1996 | Green et al. | 356/369 |
| 5,581,350 A | 12/1996 | Chen et al. | 356/369 |
| 5,596,406 A | 1/1997 | Rosencwaig et al. | 356/327 |
| 5,666,201 A | 9/1997 | Johs et al. | 356/369 |
| 5,706,212 A | 1/1998 | Thompson et al. | 364/525 |
| 5,793,480 A | 8/1998 | Lacey et al. | 356/73 |
| 5,818,596 A | 10/1998 | Imai et al. | 356/381 |
| 5,859,424 A | 1/1999 | Norton et al. | 250/226 |
| 5,872,630 A | 2/1999 | Johs et al. | 356/369 |
| 5,877,859 A | 3/1999 | Aspnes et al. | 356/364 |
| 5,929,995 A | 7/1999 | Johs | 356/369 |
| 5,946,098 A | 8/1999 | Johs et al. | 356/364 |
| 5,963,325 A | 10/1999 | Johs et al. | 356/364 |
| 5,973,787 A | 10/1999 | Aspnes et al. | 356/369 |
| 6,031,619 A | 2/2000 | Wilkens et al. | 356/419 |
| 6,034,777 A | 3/2000 | Johs et al. | 356/369 |
| 6,084,674 A | 7/2000 | Johs et al. | 356/364 |
| 6,084,675 A | 7/2000 | Herzinger et al. | 356/369 |
| 6,100,981 A | 8/2000 | Johs et al. | 356/364 |
| 6,118,537 A | 9/2000 | Johs et al. | 356/369 |
| 6,134,012 A | 10/2000 | Aspnes et al. | 356/369 |
| 6,141,102 A | 10/2000 | Johs et al. | 356/364 |
| 6,181,421 B1 | 1/2001 | Aspnes et al. | 356/369 |
| 6,320,657 B1 | 11/2001 | Aspnes et al. | 356/369 |
| 6,353,477 B1 | 3/2002 | Johs et al. | 356/369 |
| 6,411,385 B2 | 6/2002 | Aspnes et al. | 356/369 |
| 6,414,302 B1 | 7/2002 | Freeouf | 250/225 |
| 6,449,043 B2 | 9/2002 | Aspnes et al. | 356/369 |
| 6,493,097 B1 | 12/2002 | Ivarsson | 356/630 |
| 6,624,890 B2 | 9/2003 | Backman et al. | 356/369 |
| 6,650,415 B2 | 11/2003 | Aspnes et al. | 356/369 |
| 6,831,743 B2 | 12/2004 | Aspnes et al. | 356/369 |
| 7,075,649 B1 * | 7/2006 | Johs et al. | 356/369 |
| 7,158,231 B1 * | 1/2007 | Woollam et al. | 356/369 |
| 7,173,700 B2 | 2/2007 | Aspnes | 356/369 |
| 7,245,376 B2 * | 7/2007 | Liphardt et al. | 356/369 |

* cited by examiner

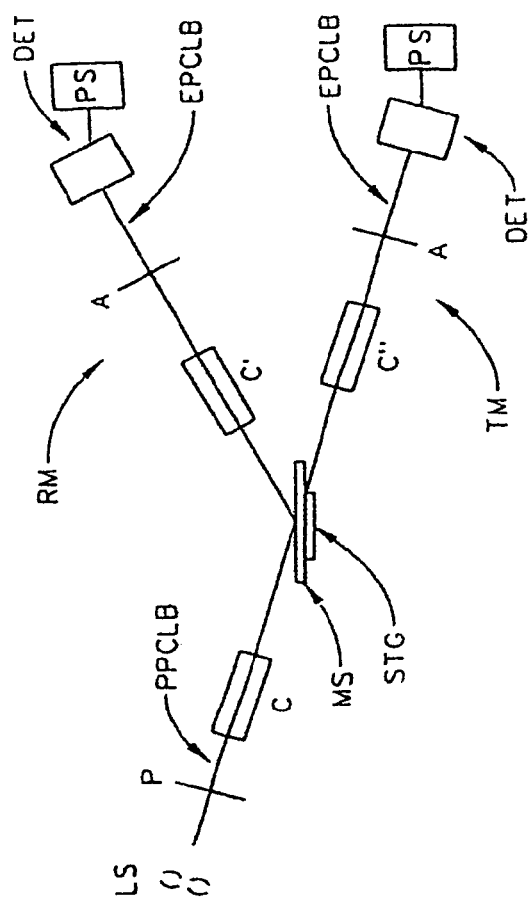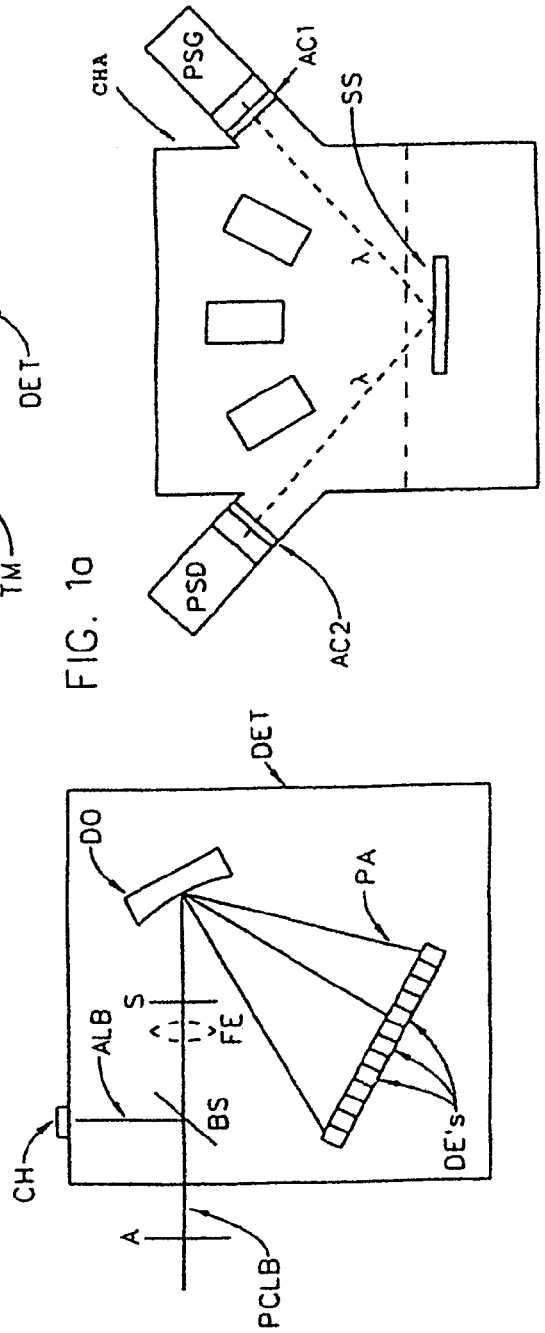

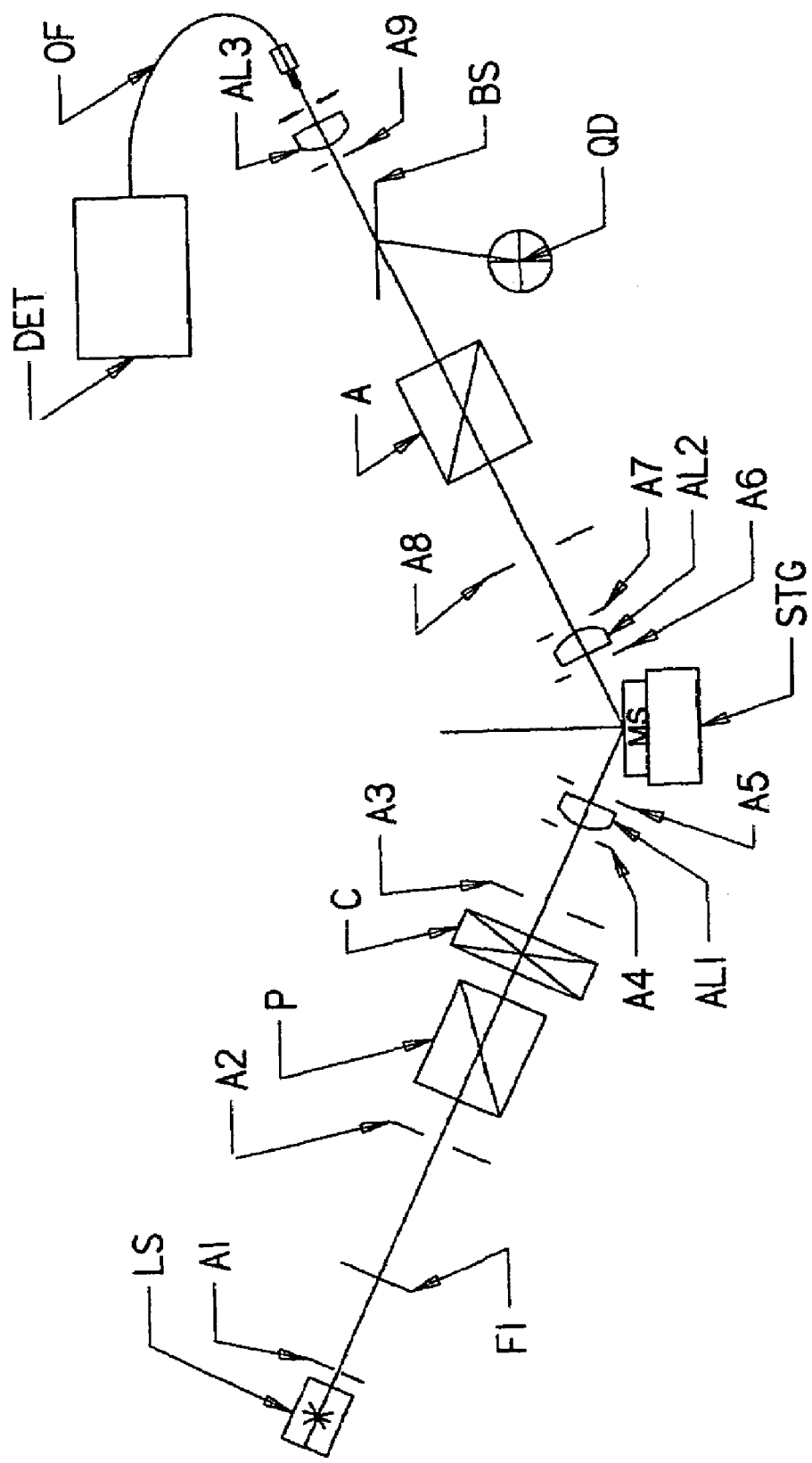
FIG. 1b1

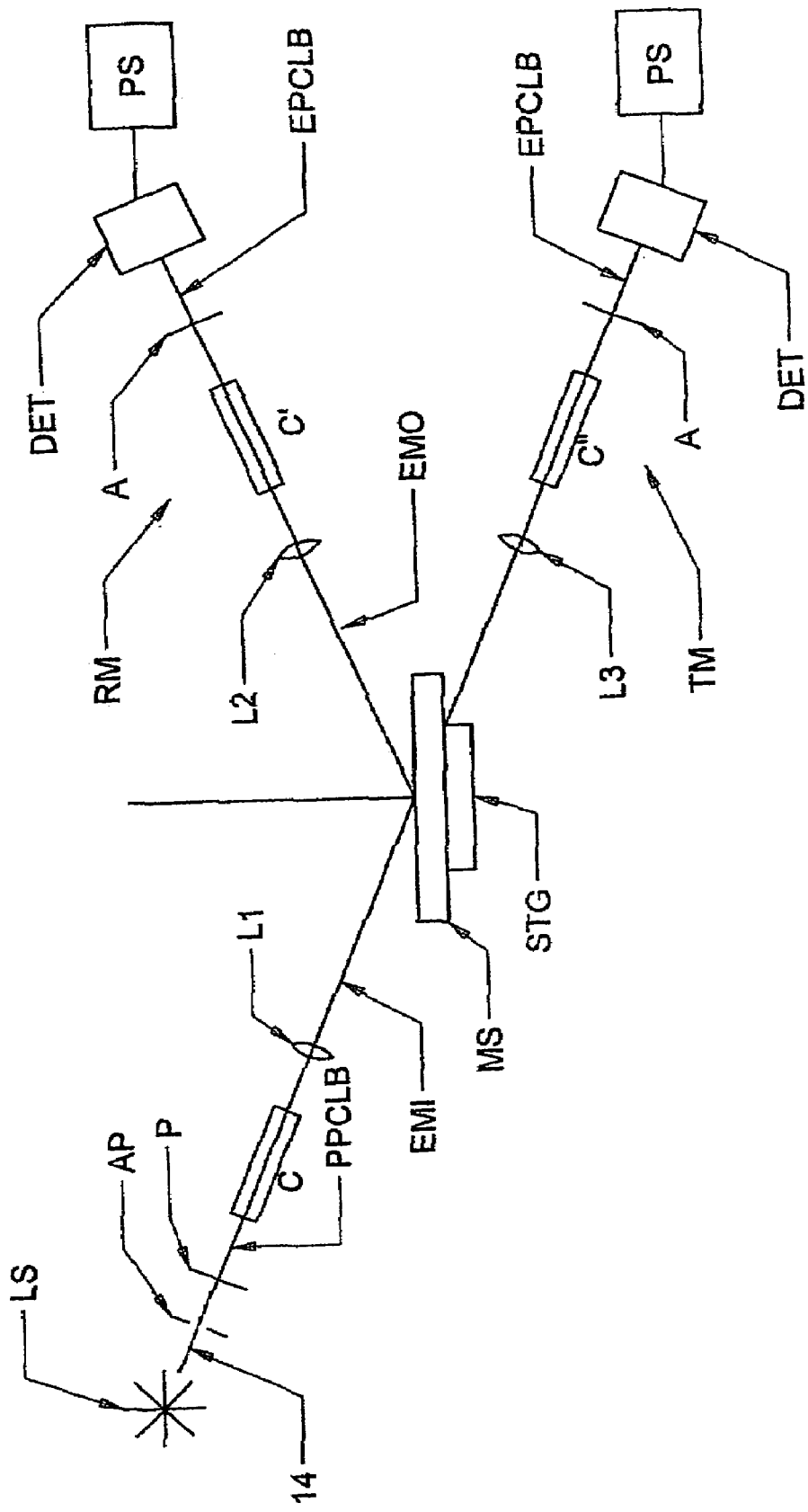
FIG. 1b2

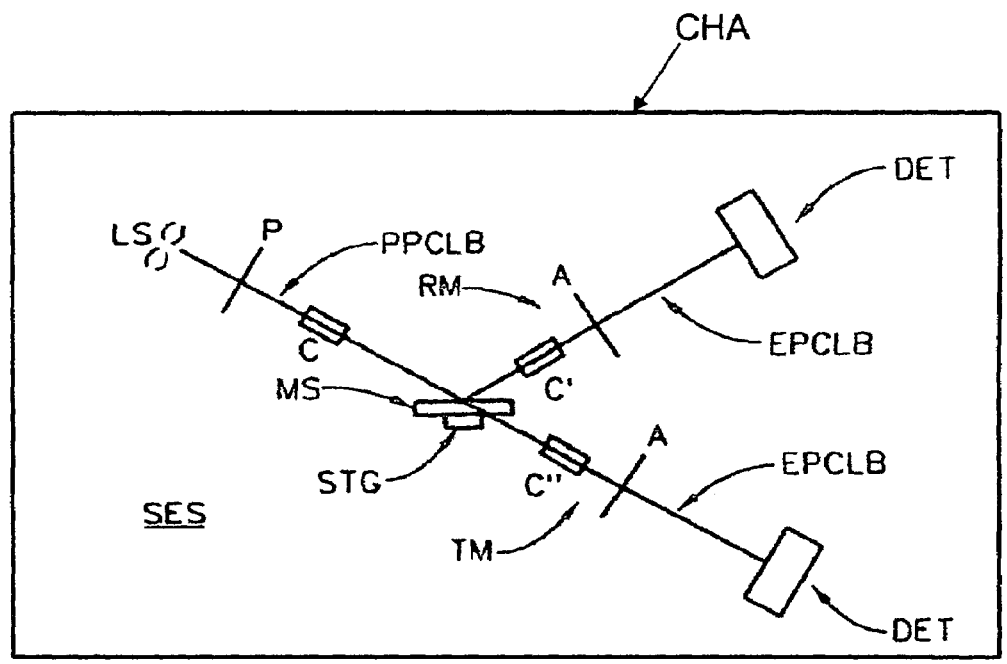
FIG. 1d
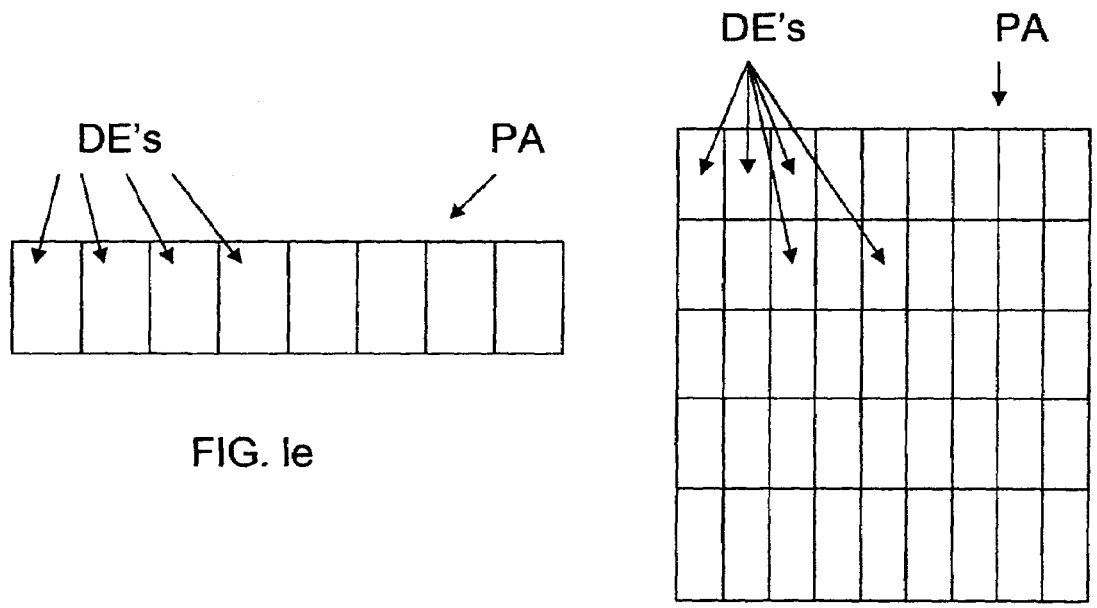
FIG. 1e
FIG. 1f

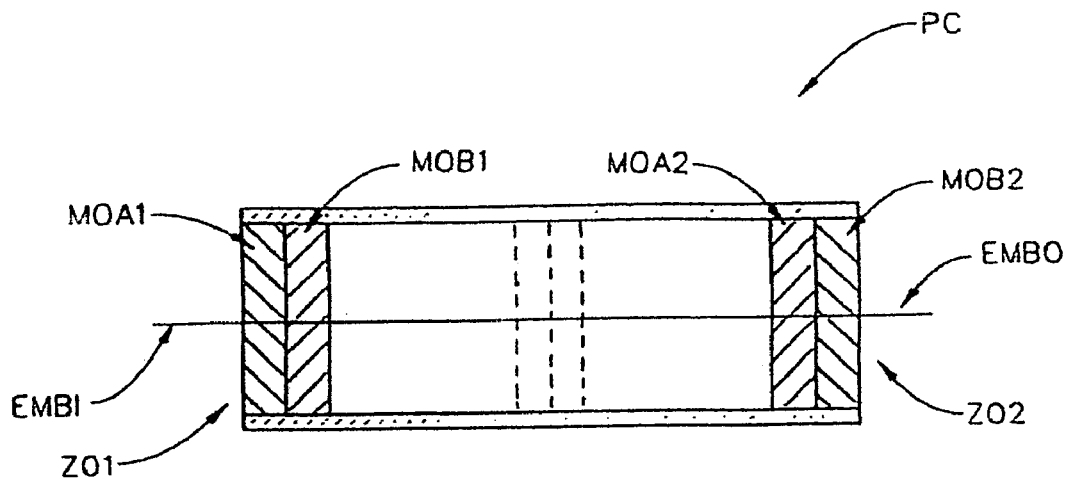
FIG. 9g₁
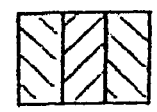
FIG. 9g₂
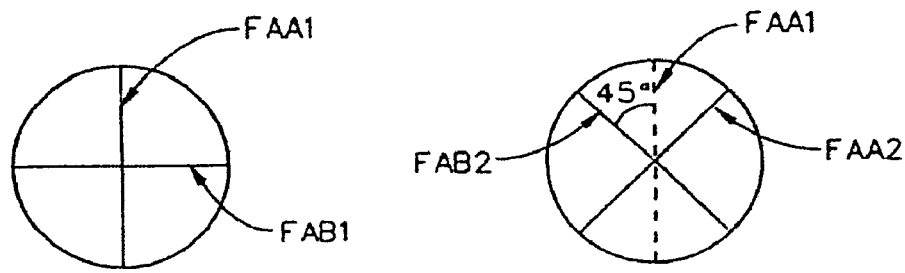
FIG. 9h    FIG. 9i
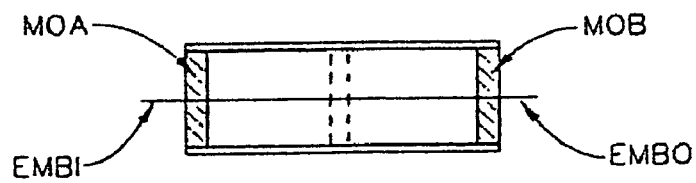
FIG. 9j

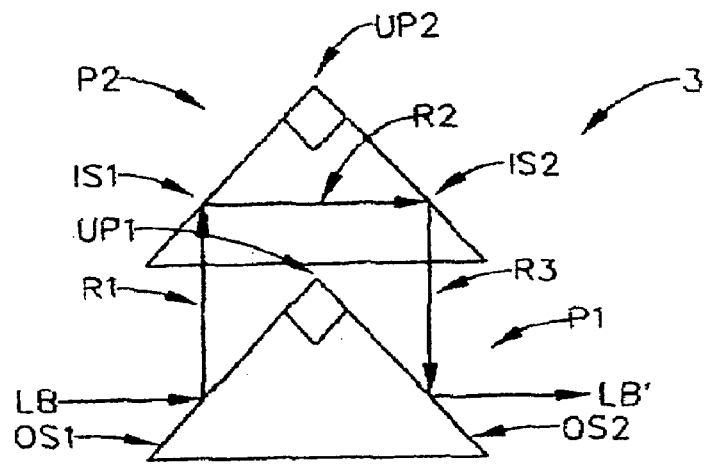
FIG. 9k1
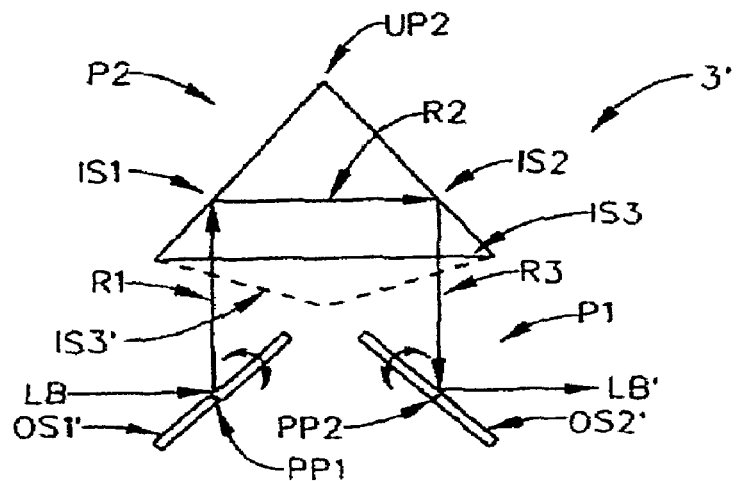
FIG. 9k2
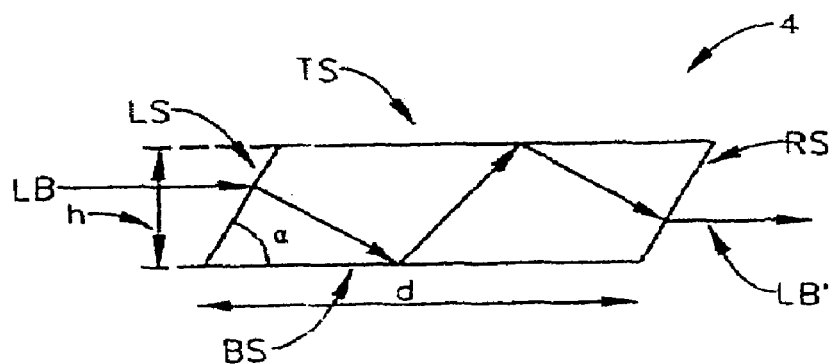
FIG. 9l

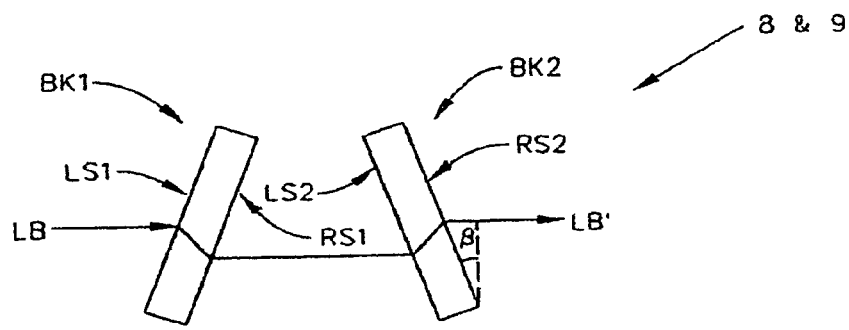
FIG. 9o1
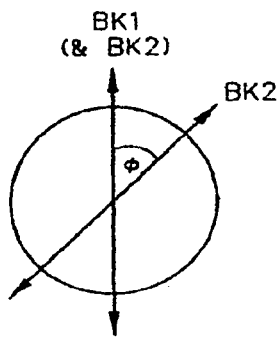
FIG. 9o2
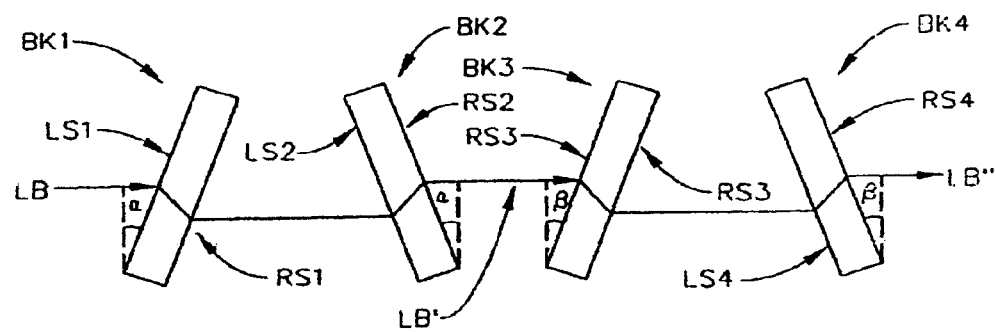
FIG. 9p1

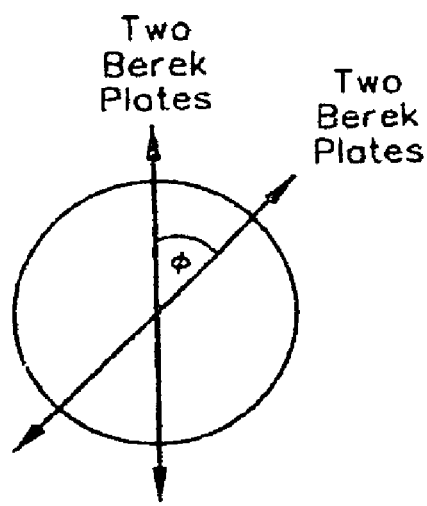
FIG. 9p2
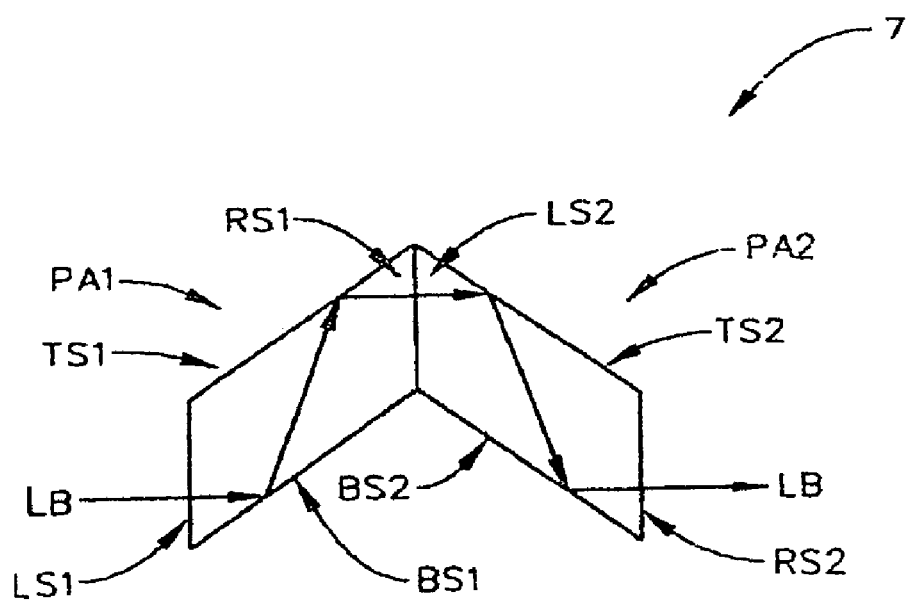
FIG. 9q

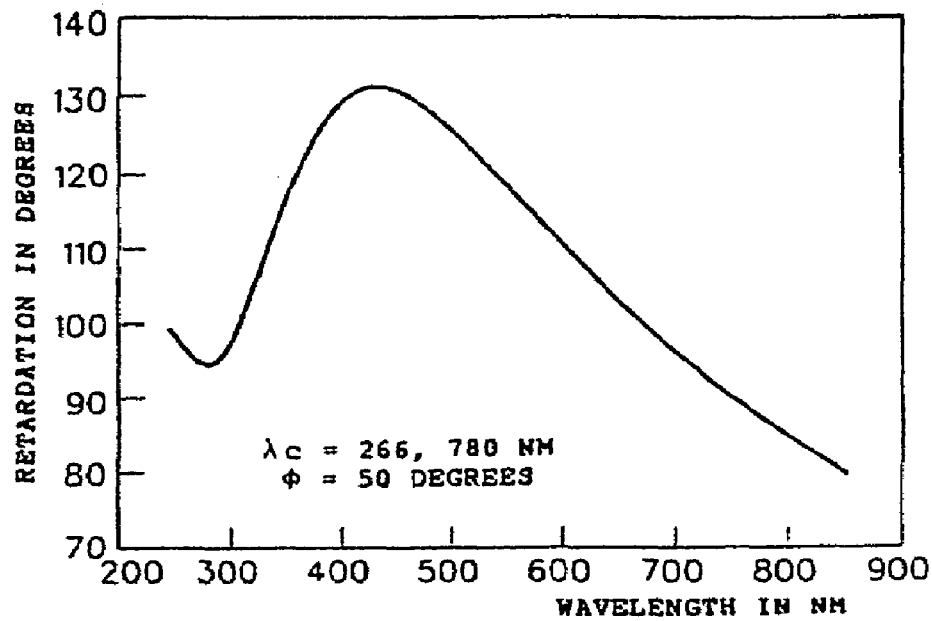
FIG. 10f
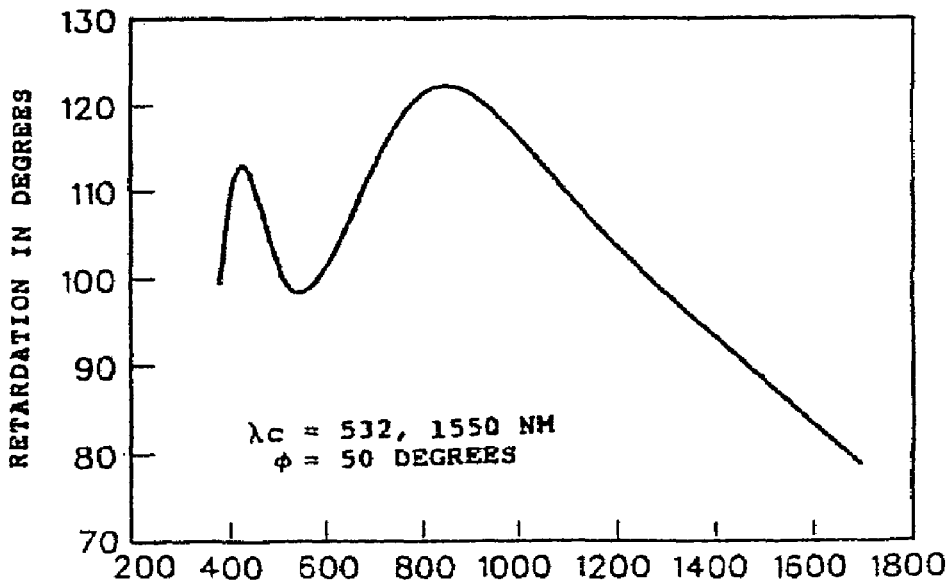
FIG. 10g₁

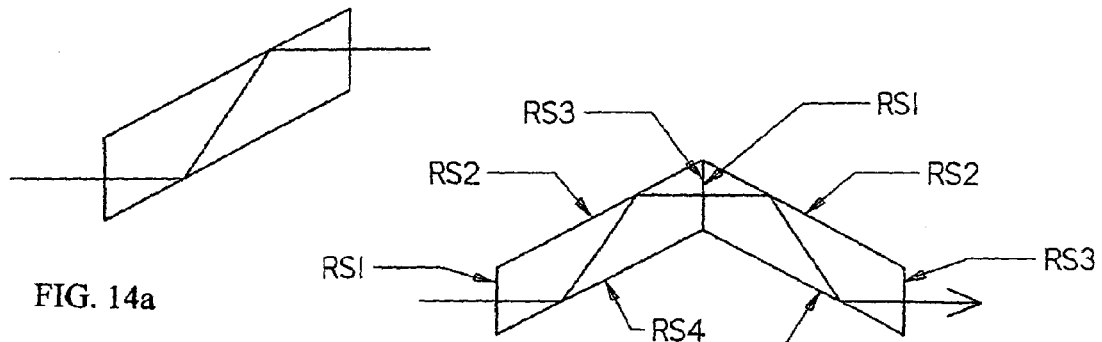
FIG. 14a
FIG. 14b
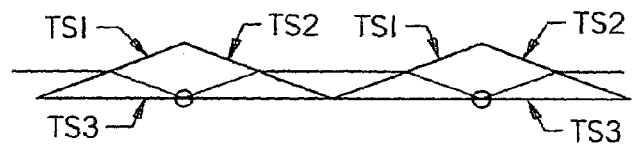
FIG. 15
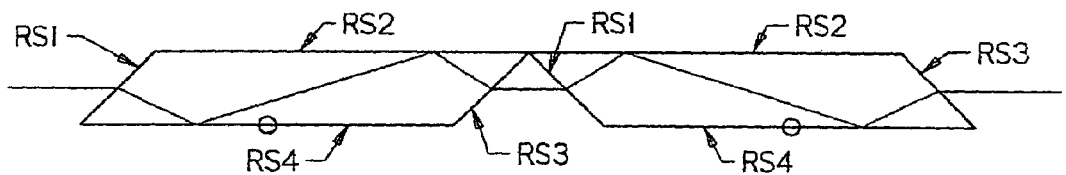
FIG. 16
FIG. 17a
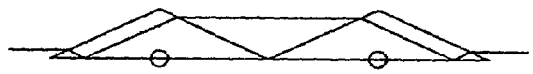
FIG. 17b
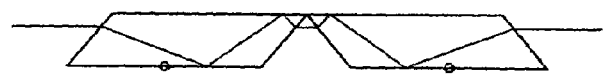
FIG. 18a
FIG. 18b Beam angle=+1°, Ψ=56.953°, Δ=70.425°

Beam angle=+1°, Ψ=52.357°, Δ=114.232°

Beam angle=0°, Ψ=56.940°, Δ=70.419°

Beam angle=0°, Ψ=52.349°, Δ=114.221°

Beam angle=-1°, Ψ=56.953°, Δ=70.425°

Beam angle=-1°, Ψ=52.357°, Δ=114.232°

SPECTROSCOPIC ELLIPSOMETER AND POLARIMETER SYSTEMS

This Application is a CIP of application Ser. No. 11/497,921 Filed Aug. 3, 2006; now U.S. Pat. No. 7,489,400 and therevia of application Ser. No. 10/613,051 Filed Jul. 7, 2003; now U.S. Pat. No. 7,009,006 and therevia Claims benefit of 60/229,755 filed Sep. 5, 2000. This Application is also a Continuation-in-Part of Co-Pending application Ser. No. 09/945,962 Filed Sep. 4, 2001, now U.S. Pat. No. 7,075,649 and therevia of application Ser. No. 09/517,125 Filed Feb. 29, 2000; (now abandoned); and of Ser. No. 09/246,888 filed Feb. 8, 1999, (now U.S. Pat. No. 6,084,675);and further of Ser. No. 09/225,118 Jan. 4, 1999 (now U.S. Pat. No. 6,084,674); Ser. No. 09/223,822 Jan. 4, 1999 (now U.S. Pat. No. 6,118,537); Ser. No. 09/232,257 Jan. 19, 1999 (now U.S. Pat. No. 6,141,102); Ser. No. 09/225,371 Jan. 4, 1999 (now U.S. Pat. No. 6,100,981); Ser. No. 09/225,076 Jan. 4, 1999 (now U.S. Pat. No. 5,963,325); which Applications depended from Ser. No. 08/997,311 filed Dec. 23, 1997, (now U.S. Pat. No. 5,946,098). Further, via the Ser. No. 09/246,888 application, this application is a Continuation-In-Part of Ser. No. 08/912,211 filed Aug. 15, 1997, (now U.S. Pat. No. 5,872,630), which Continued-In-Part from Ser. No. 08/530,892 filed Sep. 20, 1995, (now U.S. Pat. No. 5,666,201); and and is also a CIP of Ser. No. 08/618,820 filed Mar. 20, 1996, (now U.S. Pat. No. 5,706,212). In addition, priority is Claimed from Ser. No. 09/162,217 filed Sep. 29, 1998 via above Applications. This Application is further a CIP of Pending application Ser. No. 10/928,429 Aug. 27, 2004; now U.S. Pat. No. 7,316,529 and therevia Claims Benefit of Provisional Application Ser. No. 60/473,615 Filed Aug. 27, 2004. This Application is a further a CIP of Co-Pending application Ser. No. 11/585,301 Filed Oct. 23, 2006; and therevia of Ser. No. 10/829,620 Filed Apr. 22, 2004; Ser. No. 10/034,800 Filed Dec. 28, 2001; (now U.S. Pat. No. 6,822,738); Ser. No. 09/583,229 Filed May 30, 2000; (now U.S. Pat. No. 6,804,004); Ser. No. 10/699,540 Filed Nov. 1, 2003; (now U.S. Pat. No. 7,158,231); Ser. No. 08/912,211 Filed Aug. 15, 1997; (now U.S. Pat. No. 5,872,630); Ser. No. 08/530,892 Filed Sep. 20, 1995; (now U.S. Pat. No. 5,666,201); Ser. No. 10/425,801 Filed Apr. 29, 2003; and Claims Benefit therevia or directly, of Provisional Applications 60/473,616 Filed May 28, 2003; 60/553,032 Filed Mar. 15, 2004; 60/517,566 Filed Nov. 6, 2003; 60/572,204 Filed May 18, 2004; 60/527,554 Filed Dec. 6, 2003; 60/527,638 Filed Dec. 8, 2003; 60/576,466 Filed Jun. 3, 2004; 60/498,479 Filed; Aug. 28, 2003; 60/424,589 Filed Nov. 7, 2002. This Application is a further a CIP of Co-Pending application Ser. No. 11/084,827 Filed Mar. 21, 2005; now U.S. Pat. No. 7,301,631 and therevia Claims Benefit of Provisional Ser. No., 60/611,173 Filed Sep. 17, 2004. This Application further Claims benefit of Provisional Application Ser. No. 60/749,768 Filed Dec. 13, 2005.

TECHNICAL FIELD

The disclosed invention relates to spectroscopic rotating compensator ellipsometer and polarimeter systems, and more particularly to a specific configuration comprising a source of polychromatic beam of electromagnetic radiation, a polarizer, a stage for supporting a material system, an analyzer, a dispersive optics and a detector system which contains a multiplicity of detector elements, said system further comprising a rotating compensator and containment within an environmental control chamber. Preferred compensators, which enter retardance between orthogonal components of a beam of polarized electromagnetic radiation comprise multiple sequential element, substantially achromatic retarders which use multiple total internal reflections of a single, undeviated, transmitted beam to generate retardance. Said reflections can be oriented to minimize changes in the net retardance vs. the input beam angle over a wide spectral range, (for example, 130-1700 nm), as a function of compensator translation and rotation.

BACKGROUND

Ellipsometry is a well known means by which to monitor material systems, (samples). In brief, a polarized beam of electromagnetic radiation of one or more wavelengths is caused to impinge upon a material system, (sample), along one or more angles of incidence and then interact with a material system, (sample). Beams of electromagnetic radiation can be considered as comprised of two orthogonal components, tie. "P" and "S"), where "P" identifies a plane which contains both an incident beam of electromagnetic radiation, and a normal to an investigated surface of a material system, (sample), being investigated, and where "S" identifies a plane perpendicular to the "P" plane and parallel to said surface of said material system, (sample). A change in polarization state in a polarized beam of electromagnetic radiation caused by said interaction with a material system, (sample), is representative of properties of said material system, (sample). (Note polarization state basically refers to a magnitude of a ratio of orthogonal component magnitudes in a polarized beam of electromagnetic radiation, and a phase angle therebetween.) Generally two well known angles, (PSI and DELTA), which characterize a material system, (sample), at a given angle-of-incidence, are determined by analysis of data which represents change in polarization state. Additional sample identifying information is often also obtained by application of ellipsometry, including layer thicknesses, (including thicknesses for multilayers), optical thicknesses, sample temperature, refractive indicies and extinction coefficients, index grading, sample composition, surface roughness, alloy and/or void fraction, parameter dispersal and spectral dependencies on wavelength, vertical and lateral inhomogenieties etc.

Continuing, ellipsometer systems generally include a source of a beam of electromagnetic radiation, a polarizer means, which serves to impose a linear state of polarization on a beam of electromagnetic radiation, a stage for supporting a material system, (sample), and an analyzer means which serves to select a polarization state in a beam of electromagnetic radiation after it has interacted with a material system, (sample), and pass it to a detector system for analysis therein. As well, one or more compensator(s) can be present and serve to affect a phase angle change between orthogonal components of a polarized beam of electromagnetic radiation. It is noted that to obtain acceptable ellipsometer and/or polarimeter performance over a wide spectral range, compensator-based ellipsometer and/or polarimeter designs require a compensator element that provides retardance within a certain acceptable range over the entire spectral range. Traditionally, birefringent waveplates of quartz or $MgF_2$ have been used as compensator elements in rotating element designs. A single waveplate exhibits a (1/wavelength) dependence in retardance vs. wavelength, while a dual/multiple waveplate design, (as disclosed in U.S. Pat. No. 6,353,477), can minimize the effect of the (1/wavelength) dependence.

Continuing, spectroscopic ellipsometer systems utilize a source which simultaneously provides a plurality of wavelengths, which Source can be termed a "broadband" source of electromagnetic radiation. It is disclosed that sources of ultraviolet wavelength electromagnetic radiation which produce wavelengths between below 245 nm and 1100 nm at usable intensities, without generation of significant levels of ozone are known. A problem inherent in operation, however, is that to increase intensity output therefrom or extend the useable wavelength range lower limit to say 220 nm or even 160 nm and below, results in increased heat production and accompanying production of levels of ozone to which personnel can not be safely exposed. The temperature of the source can be controlled by flowing a gas therearound to dissipate increased heat, but this also serves to unacceptably distribute produced ozone into surrounding atmosphere when it is produced. It has also been discovered that flowing a cooling gas around a source of ultraviolet wavelength electromagnetic radiation serves to modulate intensity output. While not limiting, a source of ultraviolet wavelength electromagnetic radiation which can stably provide increased intensity output and/or shorter wavelengths, while not distributing accompanying produced ozone to surrounding atmosphere, or causing operator accessible outer extents thereof to exceed about 50 C, might supplement the present invention.

A number of types of ellipsometer systems exist, such as those which include rotating elements and those which include modulation elements. Those including rotating elements include rotating polarizer (RP), rotating analyzer (RA) and rotating compensator (RC). The presently disclosed invention comprises a rotating compensator ellipsometer system. It is noted that rotating compensator ellipsometer systems do not demonstrate "dead-spots" where obtaining data is difficult. They can read PSI and DELTA of a material system over a full range of degrees with the only limitation being that if PSI becomes essentially zero (0.0), one can't then determine DELTA as there is not sufficient PSI polar vector length to form the angle between the PSI vector and an "X" axis. In comparison, rotating analyzer and rotating polarizer ellipsometers have "dead spsots" at DELTA's near 0.0 or 180 Degrees and modulation element ellipsometers also have "dead spots" at PSI near 45 Degrees. The utility of rotating compensator ellipsometer systems should then be apparent. Another benefit provided by fixed polarizer (P) and analyzer (A) positions is that polarization state sensitivity to input and output optics during data acquisition is essentially non-existent. This enables relatively easy use of optic fibers, mirrors, lenses etc. for input/output.

A Search for relevant Patents was conducted. Most important is a Patent to Johs et al., U.S. Pat. No. 5,872,630, from which the present Application is derived as a CIP via intervening CIP Applications. Said 630 Patent describes:

A spectroscopic rotating compensator material system investigation system comprising a source of a polychromatic beam of electromagnetic radiation, a polarizer, a stage for supporting a material system, an analyzer, a dispersive optics and at least one detector system which contains a multiplicity of detector elements, said spectroscopic rotating compensator material system investigation system further comprising at least one compensator(s) positioned at a location selected from the group consisting of:
  before said stage for supporting a material system;
  after said stage for supporting a material system; and
  both before and after said stage for supporting a material system;
such that when said spectroscopic rotating compensator material system investigation system is used to investigate a material system present on said stage for supporting a material system, said analyzer and polarizer are maintained essentially fixed in position and at least one of said at least one compensator(s) is caused to continuously rotate while a polychromatic beam of electromagnetic radiation produced by said source of a polychromatic beam of electromagnetic radiation is caused to pass through said polarizer and said compensator(s), said polychromatic beam of electromagnetic radiation being also caused to interact with said material system, pass through said analyzer and interact with said dispersive optics such that a multiplicity of essentially single wavelengths are caused to simultaneously enter a corresponding multiplicity of detector elements in said at least one detector system.

Said 630 Patent also, amongst other disclosure, describes a mathematical regression based calibration procedure which makes possible the use of essentially any compensator regardless of non-achromatic characteristics.

Another Patent to Johs, from which the 630 Patent was continued-in part, is U.S. Pat No. 5,666,201, filed Sep. 20, 1995. The focus in said 201 Patent comprises a detector arrangement in which multiple orders of a dispersed beam of electromagnetic radiation are intercepted by multiple detector systems. However, claim 8 in the 201 Patent, in combination with a viewing the drawings therein, provide conception of the spectroscopic rotating compensator ellipsometer, as claimed in claim 1 of the Johs 630 Patent and, in fact, the 630 Patent issued in view of a terminal disclaimer based upon the 201 Patent. A CIP of the 630 Patent, is U.S. Pat. No. 6,353,477 to Johs et al. which describes preferred multiple element compensators.

Also disclosed is U.S. Pat. No. 5,706,212, Issued Jan. 6, 1998, and Filed Mar. 20, 1996 for an infrared ellipsometer system regression based calibration procedure. Said 212 Patent describes use of a substantially achromatic rotating compensator and application of mathematical regression in a calibration procedure which evaluates calibration parameters in both rotating and stationary components. The 212 Patent describes that 2 OMEGA and 4 OMEGA associated terms are generated by a detector of a signal which passes through a compensator caused to rotate at a rate of OMEGA. Said 630 Patent was continued-in-part therefrom, as is the present application via an intervening Patent application. It is noted that the 212 Patent application was filed four months prior to the earliest priority Patent Application, of Aspnes et al. Patents, (ie. U.S. Pat. Nos. 6,320,657, 6,134,012, 5,973,787 and 5,877,859), the later of which was Filed on Jul. 24, 1996. Additional Patents to Aspnes et al. include U.S. Pat. Nos. 7,173,700, 6,831,743, 6,650,415, 6,449,043 and 6,411,385. The Aspnes Patents describe broadband spectroscopic rotating compensator ellipsometer systems wherein the utility is found in the use of a "substantially non-achromatic" compensator, (see claim 1 in the 657 Patent), and selecting a wavelength range and compensator so that "an effective phase retardation value is induced covering at least from 90 degrees to 180 degrees", (012 Patent), over a range of wavelengths of at least 200-800 nm. The 787 and 859 recite that at least one wavelength in said wavelength range has a retardation imposed of between 135 and 225 Degrees, and another wavelength in the wavelength range has a retardation imposed which is outside that retardation Range. The utility of the Therma-wave Patents derives from the identified conditions being met so that at least one of a 2 OMEGA and a 4 OMEGA coefficient provided by a detector provides usable information at a wavelength, even when said coefficient does not provide usable information at other wavelengths. Again, the identified Aspnes et al. Patents recite directly, or describe the presence of a "substantially-non-Achromatic" compensator, while, it is noted at this point, the invention disclosed in this Application utlizes what are properly termed substantially-achromatic or Psuedo-Achromatic compensators. It is further noted that the U.S. Pat. No. 5,716,212 Patent application, from which this Application continues-in-part, was filed prior to Jul. 24, 1976 filing date of the 859 Aspnes et al. priority Patent Application. The disclosed invention then has Priority to simultaneous use of 2 OMEGA and 4 OMEGA signals provided from a detector in a spectroscopic rotating compensator ellipsometer system which utilizes "other-than-substantially non-achromatic" compensators, namely "substantially-achromatic" or "pseudo-achromatic" compensators, to characterize samples, emphasis added.

A recently published PCT Application is No. WO 01/90687 A2, which is based on U.S. application Ser. No. 09/575,295 filed May 3, 2001. This Application was filed by Thermawave Inc. and specifically describes separate use of a 2ω and a 4ω term to provide insight to sample thickness and temperature.

Another Patent, U.S. Pat. No. 4,053,232 to Dill et al. describes a rotating-compensator ellipsometer system, which operates utilizes monochromatic light.

Two Patents which identify systems which utilize polychromatic light in investigation of material systems, U.S. Pat. Nos. 5,596,406 and 4,668,086 to Rosencwaig et al. and Redner, respectively, were also identified.

Also identified is a Patent to Woollam et al, U.S. Pat. No. 5,373,359 as it describes a rotating analyzer ellipsometer system which utilizes white light. Patents continued from the 359 Woollam et al. Patent are, U.S. Pat. Nos. 5,504,582 to Johs et al. and 5,521,706 to Green et al. Said 582 Johs et al. and 706 Green et al. Patents describe use of polychromatic light in a rotating analyzer ellipsometer system.

A Patent to Johs et al., U.S. Pat. No. 6,034,777 describes application of ellipsometry in an evacuated chamber comprising windows.

A Patent to Johs, U.S. Pat. No. 5,929,995 is disclosed as it describes application of ellipsometry in an evacuated chamber comprising windows.

A Patent to Bernoux et al., U.S. Pat. No. 5,329,357 is identified as it describes the use of optical fibers as input and output means in an ellipsometer system.

A Patent to Chen et al., U.S. Pat. No. 5,581,350 is identified as it describes the application of regression in calibration of ellipsometer systems.

Additionally, Patents pertaining to optical elements, and particularly to compensators/retarders per se are:

U.S. Pat. No. 4,917,461 to Goldstein, describes an achromatic infrared retarder comprised of two identical prisms in combination with a reflective surface;

U.S. Pat. No. 4,772,104 to Buhrer which describes an achromatic optical filter comprised of two birefringent disks;

U.S. Pat. No. 4,961,634 to Chipman describes an infrared achromatic retarder comprised of CdS and CdSe plates aligned with the fast axes thereof perpendicular to one another;

U.S. Pat. No. 6,181,421 to Aspnes et al., describes a tipped Berek plate compensator.

U.S. Pat. No. 5,946,098 to Johs, Herzinger and Green, describes numerous optical elements. In addition Patents to Johs et al. U.S. Pat. Nos. 6,084,674; 6,118,537; 6,100,981; 6,141,102; 6,100,981; 5,963,325; 6,084,674 and to Herzinger et al. U.S. Pat. No. 6,084,675, which Applications depend from application Ser. No. 08/997,311 filed Dec. 23, 1997, now said U.S. Pat. No. 5,946,098;

Additional Patents which describe compensators are U.S. Pat. No. 548,495 to Abbe; U.S. Pat. No. 4,556,292 to Mathyssek et al.; U.S. Pat. No. 5,475,525 Tournois et al.; U.S. Pat. No. 5,016,980 Waldron; and U.S. Pat. No. 3,817,624 to Martin and U.S. Pat. No. 2,447,828 to West;

And, Patents to Robert et al., U.S. Pat. Nos. 4,176,951 and 4,179,217 are also disclosed as they describe rotating birefringent elements in ellipsometers which produce 2ω and 4ω components.

A PCT Patent Application, No. WO 01/086257 is also known and is disclosed as it describes a combination of an aperture and lens to define a spot on a sample.

A Patent to Lacey et al., U.S. Pat. No. 5,793,480 is disclosed as it describes a field stop and lens combination in an ellipsometer prior to a sample.

A Patent to Spanier et al., U.S. Pat. No. 5,166,752 is disclosed as it describes an ellipsometer with lenses and apertures before and after a sample.

A Patents to Lessner et al., U.S. Pat. No. 4,054,812 describes a Source of Spectroscopic electromagnetic radiation which provides heat sink and ozone containment.

A Patent to Ellebracht et al., U.S. Pat. No. 4,322,165 is disclosed as it describes purging in a VUV plasma atomic emission spectroscopic instrument.

A Patent to Burns et al., U.S. Pat. No. 4,875,773 is disclosed as it describes an optical system for a multidetector array spectrograph.

A Patent to Freeouf, U.S. Pat. No. 6,414,302 is disclosed as it describes a high photon energy, (up through 10 eV), range reflected light characterization system.

A Patent to Aspnes et al., U.S. Pat. No. 5,091,320 is disclosed as it describes application of ellipsometry with an evacuated chamber.

A Patent to Hartley, U.S. Pat. No. 4,770,895 is disclosed as it describes application of ellipsometry with an evacuated chamber.

A Published Patent Application by McAninch, No, 2002/0149774 A1 is disclosed as it describes purging a measurement region near a substrate in a metrology tool.

A J. A. Woollam CO. Flyer titled VUV-VASE (Registered Trademark), is disclosed as it describes a monochromater based rotating analyzer ellipsomete system in a purged chamber.

A Patent to Ivarsson, U.S. Pat. No. 6,493,097 is disclosed as it describes a Detector Array in an analytical instrument using electromagnetic radiation.

A Patent to Stewart, U.S. Pat. No. 5,229,833 is disclosed as it describes an optical sensor comprising a CCD Array.

A Patent to Azzam, U.S. Pat. No. 5,337,146 is disclosed as it describes a spectrophotometer comprising a linear array detector.

A Patent to Wilkins et al., U.S. Pat. No. 6,031,619 describes an imaging spectrometer with a CCD matrix or row detector.

A Patent to Imai et al., U.S. Pat. No. 5,818,596 is disclosed as it describes use of purging gas to prevent contaminants on samples, but does hot disclose ellipsometry or a multiple detector element detector array.

A Published Patent Application by McAninch, No, 2002/0149774 A1 is disclosed as it describes purging a measurement region near a substrate in a metrology tool.

A Published Patent Application by Wang et al., No. 2003/0071996 A1 is disclosed as it involves purging of the environment of one beam in a system involving two beams.

A Published Patent Application by Eckert et al., No. US 2003/0150997 A1 is disclosed as it describes use of VUV wavelengths and purging.

Additional known relevant Patents are:
- U.S. Pat. No. 5,706,212 to Thompson et al.;
- U.S. Pat. No. 6,353,477 to Johs et al.;
- U.S. Pat. No. 5,963,325 to Johs et al.;
- U.S. Pat. No. 6,141,102 to Johs et al.;
- U.S. Pat. No. 6,084,675 to Herzinger et al. U.S. Pat. No. 6,118,537 to Johs et al.;
- U.S. Pat. No. 6,100,981 to Johs et al.;
- U.S. Pat. No. 6,084,674 to Johs et al.
- U.S. Pat. No. 6,084,675 to Herzinger et al.

Regarding Articles,

An article by Johs, titled "Regression Calibration Method For Rotating Element Ellipsometers", which appeared in Thin Film Solids, Vol. 234 in 1993 is also identified as it predates the Chen et al. Patent and describes an essentially similar approach to ellipsometer calibration.

An Article titled "A New Purged UV Spectroscopic Ellipsometer to Characterize Thin Films and Multilayers at 157 nm", Boher et al., Proc. SPIE, Vol. 3998, (June 2000) is disclosed as it describes a UV spectroscopic ellipsometer in combination with purging.

A presentation titled "Characterisation of Thin Films and Multilayers in the VUV Wavelength Range Using Spectroscopic Ellipsometry and Spectroscopic Photometry", Boher et al., 157 nm Symposium, May 2000) is disclosed as it describes a UV spectroscopic ellipsometer.

A paper titled "Progress in Spectroscopic Ellipsometry: Applications from Ultraviolet to Infrared", Hilfiker et al., J. Vac. Sci. Technol. A, (July/August 2003).

A paper titled "Atomic Scale Characterization of Semiconductors by In-Situ Real Time Spectroscopic Ellipsometry", Boher et al., Thin Solid Flims 318 (1998) is disclosed as it mentions multichannel detectors.

A paper titled "Optical Characterization in the Vacuum Ultraviolet with Variable Angle Spectroscopic Ellipsometry: 157 nm and below", Hilfiker et al., Proc. SPIE Vol. 3998 (2000) is disclosed as it describes use of the J. A. Woollam CO. VUV-VASE which is a monochromater based purged system.

A paper titled "Feasibility and Applicability of Integrated Metrology Using Spectroscopic Ellipsometry in a Cluster Tool", Boher et al., SPIE Vol. 4449, (2001) is disclosed as it describes a multichannel ellipsometer applied outside an environmental chamber. This application required electromagnetic radiation to pass through windows to reach a sample.

Four papers authored or co-authored by Collins, which describe use of multichannels and rotating element ellipsometers, including rotating compensator, but not in an environmental chamber are:

"Characterization of Wide Bandgap Thin Film Growth Using UV-Extended Real Time Spectroscopic Ellipsometry Applications to Cubic Boron Nitride", Zapien et al., J. of Wide Bandgap Materials, Vol 9, No. 3 (January 2002);

"Automated Rotating Element Ellipsometers: Calibration, Operation, and Real-Time Applications", Collins, Rev. Sci. Instrum. 61 (8) (aug. 1990);

"Waveform Analysis With Optical Multichannel Detectors: Applications for Rapid-Scan Spectroscopic Ellipsometers", An et al., Rev. Sci. Instrum. 62(8), (August 1991); and "Multichannel Ellipsometer for Real Time Spectroscopy of Thin Film Deposition for 1.5 to 6.5 eV", Zapien et al., Rev. Sci. Instrum. Vol. 71, No. 9, (September 1991).

A book by Azzam and Bashara titled "Ellipsometry and Polarized light" North-Holland, 1977 is disclosed and incorporated herein by reference for general theory.

As well, identified for authority regarding regression, is a book titled Numerical Recipes in "C", 1988, Cambridge University Press.

Even in view of the prior art need remains for a rotating compensator ellipsometer that comprises a Detector system comprised of a multiplicity of detector elements, which detector elements simultaneously detect a multiplicity of wavelengths, said rotating compensator ellipsometer system being present in an environmental control chamber. Need further remains for compensator designs with substantially achromatic characteristics and which minimize deviation in the locus of a beam passed therethrough even while rotating.

DISCLOSURE OF THE INVENTION

The disclosed invention comprises a spectroscopic rotating compensator material system investigation system comprising a source of polychromatic beam of electromagnetic radiation, a polarizer, a stage for supporting a material system, an analyzer, a dispersive optics and at least one detector system which contains a multiplicity of detector elements, said spectroscopic rotating compensator material system investigation system further comprising at least one compensator(s) positioned at a location selected from the group consisting of:
- before said stage for supporting a material system;
- after said stage for supporting a material system; and
- both before and after said stage for supporting a material system.

When said spectroscopic rotating compensator material system investigation system is used to investigate a material system present on said stage for supporting a material system, said analyzer and polarizer are maintained essentially fixed in position and at least one of said at least one compensator(s) is caused to continuously rotate while a polychromatic beam of electromagnetic radiation produced by said source of a polychromatic beam of electromagnetic radiation is caused to pass through said polarizer and said at least one compensator(s) Said polychromatic beam of electromagnetic radiation is then caused to interact with a material system on said stage for supporting a material system, pass through said analyzer and interact with said dispersive optics such that a multiplicity of essentially single wavelengths are caused to simultaneously enter a corresponding multiplicity of detector elements in said at least one detector system.

In a specific, non-limiting, embodiment the disclosed invention can comprise a spectroscopic rotating compensator material system investigation system comprising:

a polarization state generator comprising:
- a source of polychromatic, (ie. broadband), beam of electromagnetic radiation;
- a first aperture with a nominal internal diameter of between 100 and 600 microns;
- a second aperture with a nominal internal diameter has a nominal internal diameter of 3 to 3.5 millimeters;
- a fixed polarizer;
- a rotating compensator;
- a third aperture with a nominal internal diameter of 3.5 millimeters;
- a forth aperture with a nominal internal diameter of 3.75 millimeters;

a first substantially achromatic lens;
a fifth aperture with a nominal internal diameter of 4.8 millimeters;

a stage for supporting a material system;

and a polarization state detector comprising:
a sixth aperture with a nominal internal diameter of 4.8 millimeters;
a second substantially achromatic lens,
a seventh aperture with a nominal internal diameter of 3.75 millimeters;
an eighth aperture with a nominal internal diameter of 3.5 millimeters;
a fixed analyzer;
a ninth aperture with an adjustable internal diameter;
a third substantially achromatic lens;
an optical fiber; and
at least one detector system which contains a dispersive element and a multiplicity of detector elements;

there optionally being a UV filter present between said source of a polychromatic beam of electromagnetic radiation and said stage for supporting a material system for the purpose of preventing the effects of UV radiation on a material system.

When said spectroscopic rotating compensator material system investigation system is used to investigate a material system present on said stage for supporting a material system, said fixed analyzer and fixed polarizer are maintained essentially fixed in position during data acquisition and said rotating compensator is caused to continuously rotate while a polychromatic beam of electromagnetic radiation produced by said source of polychromatic beam of electromagnetic radiation is sequentially caused to pass through said first aperture, second aperture, fixed polarizer, rotating compensator, third aperture, forth aperture, first substantially achromatic lens, fifth aperture, said polychromatic beam of electromagnetic radiation also passing through said UV filter, then interact with a material system placed on said stage for supporting a material system, then sequentially pass through said sixth aperture, second substantially achromatic lens, seventh aperture, eighth aperture, fixed analyzer, ninth aperture, third substantially achromatic lens, enter said optical fiber and therevia enter said detector system.

Another non-limiting recitation of a present invention ellipsometer or polarimeter system provides that it comprise:
a) a source of electromagnetic radiation;
b) a polarizer;
c) a stage for supporting a sample;
d) an analyzer; and
e) a detector;

said ellipsometer or polarimeter system further comprising at least one rotatable compensator present at least one location selected from the group consisting of:
between said source of electromagnetic radiation and said stage for supporting a sample; and
between said stage for supporting a sample and said detector;

wherein said at least one rotatable compensator comprises at least two sequential elements oriented with respect to one another such that said entered electromagnetic beam undergoes total internal reflection at least once in each of the elements, with the orientation, geometry, and symmetry of the elements being such that the output beam position is undeviated by a translation of the system, and the output beam angle is undeviated by a rotation of the system. One embodiment provides that two triangular shaped prisms are used for the elements. Preferred design provides that the angles of the triangular prisms are 26, 128, and 26 degrees. Another embodiment provides that two parallelogram shaped rhombs are used for the elements. Preferred design provides that angles of the parallelogram shaped rhombs are 36, 144, 36, and 144 degrees. Also, as mentioned, other embodiments can include one or more triangular shaped prisms and one or more parallelogram shape rhombs etc. Further, at least one of the elements can have a mechanism for translating and/or tilting at least one of the elements, for the purposes of aligning the system such that the locus of the exiting beam is substantially undeviated in position and angle from the locus of the input beam. Said compensators can be made from fused silica, $MgF_2$, CaF etc.

Importantly, regardless of specific design, the spectroscopic rotating compensator material system investigation system disclosed herein is functionally present in an environmental control chamber characterized by a selection from the group consisting of:
it comprises at least one chamber region in which is present polarization state generator comprising component(s) prior to said material system and polarization state detector comprising component(s) after said material system and optionally said material system;
it comprises at least three chamber regions, in one of which is present polarization state generator comprising component(s) prior to said material system, in the second of which is present the material system and in the third of which is present polarization state detector comprising component(s) after said material system;
it comprises at least two chamber regions, in one of which is present polarization state generator comprising component(s) prior to said material system and said material system, and in the second of which is present polarization state detector comprising component(s) after said material system;
it comprises at least two chamber regions, in one of which is present polarization state generator comprising component(s) prior to said material system, and in the second of which is present polarization state detector comprising component(s) after said material system and said material system.

The functional reason is that it is important to control atmospheric content where, for instance, UV range wavelengths are utilized, as wavelengths below about 200 nm are absorbed by oxygen and water vapor.

The compensator(s) can comprises a selection from the group consisting of:
comprised of a combination of at least two zero-order waveplates, said zero-order waveplates and having their respective fast axes rotated to a position offset from zero or ninety degrees with respect to one another;
comprised of a combination of at least a first and a second effective zero-order wave plate, said first effective zero-order wave plate being comprised of two multiple order waveplates which are combined with the fast axes thereof oriented at a nominal ninety degrees to one another, and said second effective zero-order wave plate being comprised of two multiple order waveplates which are combined with the fast axes thereof oriented at a nominal ninety degrees to one another; the fast axes of the multiple order waveplates in said second effective zero-order wave plate being rotated to a position at a nominal forty-five degrees to the fast axes of the multiple order waveplates and in said first effective zero-order waveplate;

comprised of a combination of at least a first and a second effective zero-order wave plate, said first effective zero-order wave plate being comprised of two multiple order waveplates which are combined with the fast axes thereof oriented at a nominal ninety degrees to one another, and said second effective zero-order wave plate being comprised of two multiple order waveplates which are combined with the fast axes thereof oriented at a nominal ninety degrees to one another; the fast axes of the multiple order waveplates in said second effective zero-order wave plate being rotated to a position away from zero or ninety degrees with respect to the fast axes of the multiple order waveplates and in said first effective zero-order waveplate; and comprised of a combination of at least one zero-order waveplate and at least one effective zero-order waveplate, said effective zero-order wave plate being comprised of two multiple order waveplates which are combined with the fast axes thereof oriented at a nominal ninety degrees to one another, the fast axes of the multiple order waveplates in said effective zero-order wave plate being rotated to a position away from zero or ninety degrees with respect to the fast axis of the zero-order waveplate;

and said compensator causes essentially no deviation or displacement in a polychromatic beam of electromagnetic radiation caused to pass therethrough while caused to rotate.

Said compensator provides that retardation effected thereby between orthogonal components of a beam of electromagnetic radiation at one wavelength is different than that provided thereby at least one other wavelength. Said variation is exemplified as being:

within a range of thirty (30.0) to less than one-hundred-thirty-five (135) degrees over a range of wavelengths defined by a selection from the group consisting of:
  a. minimum wavelength is less than/equal to a selection from the group consisting of 190; 160 and 155 nanometers; and the maximum wavelength is greater than/equal to a selection from the group consisting of 1700, 730 and 700 nanometers, respectively
  b. minimum wavelength is less than/equal to two-hundred-twenty (220) and maximum wavelength MAXW greater than/equal to one-thousand (1000) nanometers;
  c. within a range of wavelengths defined by a maximum wavelength (MAXW) and a minimum wavelength (MINW) range where (MAXW)/(MINW) is at least four-and-one-half (4.5);

or being within a range of seventy-five (75.0) to less than one-hundred-thirty-five (135) degrees over a range of wavelengths defined by a selection from the group consisting of:
  a. between one-hundred-ninety (190) and seven-hundred-fifty (750) nanometers;
  b. between two-hundred-forty-five (245) and nine-hundred (900) nanometers;
  c. between a selection from the group consisting of 380, 160 and 155 nanometers; and a selection from the group consisting of 1700, 300 and 280 nanometers, respectively;
  d. within a range of wavelengths defined by a maximum wavelength (MAXW) and a minimum wavelength (MINW) wherein the ratio of (MAXW)/(MINW) is at least one-and-eight-tenths.

The present invention can utilize essentially any Compensator, other examples of which are can be selected from the group consisting of:

a single element compensator, (which in the context of the disclosed invention could have its optic axis in the plane of a surface thereof, or have its optic axis substantially perpendicular thereto);

a compensator system comprised of at least two per se. zero-order waveplates (MOA) and (MOB), said per se. zero-order waveplates (MOA) and (MOB) having their respective fast axes rotated to a position offset from zero or ninety degrees with respect to one another, with a nominal value being forty-five degrees;

a compensator system comprised of a combination of at least a first (ZO1) and a second (ZO2) effective zero-order wave plate, said first (ZO1) effective zero-order wave plate being comprised of two multiple order waveplates (MOA1) and (MOB1) which are combined with the fast axes thereof oriented at a nominal ninety degrees to one another, and said second (ZO2) effective zero-order wave plate being comprised of two multiple order waveplates (MOA2) and (MOB2) which are combined with the fast axes thereof oriented at a nominal ninety degrees to one another; the fast axes (FAA2) and (FAB2) of the multiple order waveplates (MOA2) and (MOB2) in said second effective zero-order wave plate (ZO2) being rotated to a position at a nominal forty-five degrees to the fast axes (FAA1) and (FAB1), respectively, of the multiple order waveplates (MOA1) and (MOB1) in said first effective zero-order waveplate (ZO1);

a compensator system comprised of a combination of at least a first (ZO1) and a second (ZO2) effective zero-order wave plate, said first (ZO1) effective zero-order wave plate being comprised of two multiple order waveplates (MOA1) and (MOB1) which are combined with the fast axes thereof oriented at a nominal ninety degrees to one another, and said second (ZO2) effective zero-order wave plate being comprised of two multiple order waveplates (MOA2) and (MOB2) which are combined with the fast axes thereof oriented at a nominal ninety degrees to one another; the fast axes (FAA2) and (FAB2) of the multiple order waveplates (MOA2) and (MOB2) in said second effective zero-order wave plate (ZO2) being rotated to a position away from zero or ninety degrees with respect to the fast axes (FAA1) and (FAB1), respectively, of the multiple order waveplates (MOA1) and (MOB1) in said first effective zero-order waveplate (ZO1);

a compensator system comprised of at least one zero-order waveplate, ((MOA) or (MOB)), and at least one effective zero-order waveplate, ((ZO2) or (ZO1) respectively), said effective zero-order wave plate, ((ZO2) or (ZO1)), being comprised of two multiple order waveplates which are combined with the fast axes thereof oriented at a nominal ninety degrees to one another, the fast axes of the multiple order waveplates in said effective zero-order wave plate, ((ZO2) or (ZO1)), being rotated to a position away from zero or ninety degrees with respect to the fast axis of the zero-order waveplate, ((MOA) or (MOB));

where the identifiers are shown in FIGS. 9g1-9j.

Additional compensator systems, previously disclosed in patent application Ser. No. 08/997,311, (now U.S. Pat. No.

5,946,098), and CIP's therefrom, which are specifically within the scope of the invention and can be included in the selection group are:

a compensator system comprised of a first triangular shaped element, which as viewed in side elevation presents with first and second sides which project to the left and right and downward from an upper point, which first triangular shaped element first and second sides have reflective outer surfaces; said retarder system further comprising a second triangular shaped element which as viewed in side elevation presents with first and second sides which project to the left and right and downward from an upper point, said second triangular shaped element being made of material which provides reflective interfaces on first and second sides inside thereof; said second triangular shaped element being oriented with respect to the first triangular shaped element such that the upper point of said second triangular shaped element is oriented essentially vertically directly above the upper point of said first triangular shaped element; such that in use an input electromagnetic beam of radiation caused to approach one of said first and second sides of said first triangular shaped element along an essentially horizontally oriented locus, is caused to externally reflect from an outer surface thereof and travel along a locus which is essentially upwardly vertically oriented, then enter said second triangular shaped element and essentially totally internally reflect from one of said first and second sides thereof, then proceed along an essentially horizontal locus and essentially totally internally reflect from the other of said first and second sides and proceed along an essentially downward vertically oriented locus, then externally reflect from the other of said first and second sides of said first triangular shaped elements and proceed along an essentially horizontally oriented locus which is undeviated and undisplaced from the essentially horizontally oriented locus of said input beam of essentially horizontally oriented electromagnetic radiation even when said retarder is caused to rotate; with a result being that retardation is entered between orthogonal components of said input electromagnetic beam of radiation;

a compensator system comprised of, as viewed in upright side elevation, first and second orientation adjustable mirrored elements which each have reflective surfaces; said compensator/retarder system further comprising a third element which, as viewed in upright side elevation, presents with first and second sides which project to the left and right and downward from an upper point, said third element being made of material which provides reflective interfaces on first and second sides inside thereof; said third element being oriented with respect to said first and second orientation adjustable mirrored elements such that in use an input electromagnetic beam of radiation caused to approach one of said first and second orientation adjustable mirrored elements along an essentially horizontally oriented locus, is caused to externally reflect therefrom and travel along a locus which is essentially upwardly vertically oriented, then enter said third element and essentially totally internally reflect from one of said first and second sides thereof, then proceed along an essentially horizontal locus and essentially totally internally reflect from the other of said first and second sides and proceed along an essentially downward vertically oriented locus, then reflect from the other of said first and second orientation adjustable mirrored elements and proceed along an essentially horizontally oriented propagation direction locus which is essentially undeviated and undisplaced from the essentially horizontally oriented propagation direction locus of said input beam of essentially horizontally oriented electromagnetic radiation even when said compensator/retarder is caused to rotate; with a result being that retardation is entered between orthogonal components of said input electromagnetic beam of radiation;

a compensator system comprised of a parallelogram shaped element which, as viewed in side elevation, has top and bottom sides parallel to one another, both said top and bottom sides being oriented essentially horizontally, said retarder system also having right and left sides parallel to one another, both said right and left sides being oriented at an angle to horizontal, said retarder being made of a material with an index of refraction greater than that of a surrounding ambient; such that in use an input beam of electromagnetic radiation caused to enter a side of said retarder selected from the group consisting of: (right and left), along an essentially horizontally oriented locus, is caused to diffracted inside said retarder system and follow a locus which causes it to essentially totally internally reflect from internal interfaces of both said top and bottom sides, and emerge from said retarder system from a side selected from the group consisting of (left and right respectively), along an essentially horizontally oriented locus which is undeviated and undisplaced from the essentially horizontally oriented locus of said input beam of essentially horizontally oriented electromagnetic radiation even when said retarder is caused to rotate; with a result being that retardation is entered between orthogonal components of said input electromagnetic beam of radiation;

a compensator system comprised of first and second triangular shaped elements, said first triangular shaped element, as viewed in side elevation, presenting with first and second sides which project to the left and right and downward from an upper point, said first triangular shaped element further comprising a third side which is oriented essentially horizontally and which is continuous with, and present below said first and second sides; and said second triangular shaped element, as viewed in side elevation, presenting with first and second sides which project to the left and right and upward from an upper point, said second triangular shaped element further comprising a third side which is oriented essentially horizontally and which is continuous with, and present above said first and second sides; said first and second triangular shaped elements being positioned so that a rightmost side of one of said first and second triangular shaped elements is in contact with a leftmost side of the other of said first and second triangular shaped elements over at least a portion of the lengths thereof; said first and second triangular shaped elements each being made of material with an index of refraction greater than that of a surrounding ambient; such that in use an input beam of electromagnetic radiation caused to enter a side of a triangular shaped element selected from the group consisting of: (first and second), not in contact with said other triangular shape element, is caused to diffracted inside said retarder and follow a locus which causes it to essentially totally internally reflect from internal interfaces of said third sides of each of said first and second triangular shaped elements, and emerge from a side of said triangular shaped element selected from the group consisting of: (second and first), not in contact with said other triangular shape element, along an essentially horizontally oriented locus which is undeviated and undisplaced from the essentially horizontally oriented locus of said input beam of essentially horizontally oriented electromagnetic radiation even when said retarder is caused to rotate; with a result being that retardation is entered between orthogonal components of said input electromagnetic beam of radiation;

a compensator system comprised of a triangular shaped element, which as viewed in side elevation presents with first and second sides which project to the left and right and downward from an upper point, said retarder system further comprising a third side which is oriented essentially horizontally and which is continuous with, and present below said first and second sides; said retarder system being made of a material with an index of refraction greater than that of a surrounding ambient; such that in use a an input beam of electromagnetic radiation caused to enter a side of said retarder system selected from the group consisting of: (first and second), along an essentially horizontally oriented locus, is caused to diffracted inside said retarder system and follow a locus which causes it to essentially totally internally reflect from internal interface of said third sides, and emerge from said retarder from a side selected from the group consisting of (second and first respectively), along an essentially horizontally oriented locus which is undeviated and undisplaced from the essentially horizontally oriented locus of said input beam of essentially horizontally oriented electromagnetic radiation even when said retarder system is caused to rotate; with a result being that retardation is entered between orthogonal components of said input electromagnetic beam of radiation; and a compensator system comprised of first and second Berek-type retarders which each have an optical axes essentially perpendicular to a surface thereof, each of which first and second Berek-type retarders has a fast axis, said fast axes in said first and second Berek-type retarders being oriented in an orientation selected from the group consisting of: (parallel to one another and other than parallel to one another); said first and second Berek-type retarders each presenting with first and second essentially parallel sides, and said first and second Berek-type retarders being oriented, as viewed in side elevation, with first and second sides of one Berek-type retarder being oriented other than parallel to first and second sides of the other Berek-type retarder; such that in use an incident beam of electromagnetic radiation is caused to impinge upon one of said first and second Berek-type retarders on one side thereof, partially transmit therethrough then impinge upon the second Berek-type retarder, on one side thereof, and partially transmit therethrough such that a polarized beam of electromagnetic radiation passing through both of said first and second Berek-type retarders emerges from the second thereof in a polarized state with a phase angle between orthogonal components therein which is different than that in the incident beam of electromagnetic radiation, and in a propagation direction which is essentially undeviated and undisplaced from the incident beam of electromagnetic radiation even when said retarder system is caused to rotate; with a result being that retardation is entered between orthogonal components of said input electromagnetic beam of radiation;

a compensator system comprised of first and second Berek-type retarders which each have an optical axes essentially perpendicular to a surface thereof, each of which first and second Berek-type retarders has a fast axis, said fast axes in said first and second Berek-type retarders being oriented other than parallel to one another; said first and second Berek-type retarders each presenting with first and second essentially parallel sides, and said first and second Berek-type retarders being oriented, as viewed in side elevation, with first and second sides of one Berek-type retarder being oriented other than parallel to first and second sides of the other Berek-type retarder; such that in use an incident beam of electromagnetic radiation is caused to impinge upon one of said first and second Berek-type retarders on one side thereof, partially transmit therethrough then impinge upon the second Berek-type retarder, on one side thereof, and partially transmit therethrough such that a polarized beam of electromagnetic radiation passing through both of said first and second Berek-type retarders emerges from the second thereof in a polarized state with a phase angle between orthogonal components therein which is different than that in the incident beam of electromagnetic radiation, and in a propagation direction which is essentially undeviated and undisplaced from the incident beam of electromagnetic radiation, said compensator system further comprising third and forth Berek-type retarders which each have an optical axes essentially perpendicular to a surface thereof, each of which third and forth Berek-type retarders has a fast axis, said fast axes in said third and forth Berek-type retarders being oriented other than parallel to one another, said third and forth Berek-type retarders each presenting with first and second essentially parallel sides, and said third and forth Berek-type retarders being oriented, as viewed in side elevation, with first and second sides of one of said third and forth Berek-type retarders being oriented other than parallel to first and second sides of said forth Berek-type retarder; such that in use an incident beam of electromagnetic radiation exiting said second Berek-type retarder is caused to impinge upon said third Berek-type retarder on one side thereof, partially transmit therethrough then impinge upon said forth Berek-type retarder on one side thereof, and partially transmit therethrough such that a polarized beam of electromagnetic radiation passing through said first, second, third and forth Berek-type retarders emerges from the forth thereof in a polarized state with a phase angle between orthogonal components therein which is different than that in the incident beam of electromagnetic radiation caused to impinge upon the first side of said first Berek-type retarder, and in a direction which is essentially undeviated and undisplaced from said incident beam of electromagnetic radiation even when said retarder system is caused to rotate; with a result being that retardation is entered between orthogonal components of said input electromagnetic beam of radiation;

a compensator system comprised of first, second, third and forth Berek-type retarders which each have an optical axes essentially perpendicular to a surface thereof, each of which first and second Berek-type retarders has a fast axis, said fast axes in said first and second Berek-type retarders being oriented essentially parallel to one another; said first and second Berek-type retarders each presenting with first and second essentially parallel sides, and said first and second Berek-type retarders being oriented, as viewed in side elevation, with first and second sides of one Berek-type retarder being oriented other than parallel to first and second sides of the other Berek-type retarder; such that in use an incident beam of electromagnetic radiation is caused to impinge upon one of said first and second Berek-type retarders on one side thereof, partially transmit therethrough then impinge upon the second Berek-type retarder, on one side thereof, and partially transmit therethrough such that a polarized beam of electromagnetic radiation passing through both of said first and second Berek-type retarders emerges from the second thereof in a polarized state with a phase angle between orthogonal components therein which is different than that in the incident beam of electromagnetic radiation, and in a propagation direction which is essentially undeviated and undisplaced from the incident beam of electromagnetic radiation; each of which third and forth Berek-type retarders has a fast axis, said fast axes in said third and forth Berek-type retarders being oriented essentially parallel to one another but other than parallel to the fast axes of said first and second Berek-type retarders, said third and forth Berek-type retarders each presenting with first and second essentially parallel sides, and said third and forth Berek-type retarders being oriented, as viewed in side elevation, with first and second sides of one of said third and forth Berek-type retarders being oriented other than parallel to first and second sides of said forth Berek-type retarder; such that in use an incident beam of electromagnetic radiation exiting said second Berek-type retarder is caused to impinge upon said third Berek-type retarder on one side thereof, partially transmit therethrough then impinge upon said forth Berek-type retarder on one side thereof, and partially transmit therethrough such that a polarized beam of electromagnetic radiation passing through said first, second, third and forth Berek-type retarders emerges from the forth thereof in a polarized state with a phase angle between orthogonal components therein which is different than that in the incident beam of electromagnetic radiation caused to impinge upon the first side of said first Berek-type retarder, and in a direction which is essentially undeviated and undisplaced from said incident beam of electromagnetic radiation even when said retarder system is caused to rotate; with a result being that retardation is entered between orthogonal components of said input electromagnetic beam of radiation.

Continuing, said spectroscopic rotating compensator material system investigation system further comprises, preferably between said fixed polarizer and said ninth aperture, a beam splitting means which serves to divert a portion of the polychromatic beam of electromagnetic radiation which otherwise proceeds to said optical fiber, and transmits the remainder of said polychromatic beam of electromagnetic radiation theretoward, said diverted portion of said polychromatic beam of electromagnetic radiation being directed by said beam splitting means into an alignment means selected from the group consisting of:
  reticule; and
  electromagnetic beam detecting means;

such that in use said alignment means provides monitored alignment capability thereby allowing precise control of the locus of propagation of the portion of said polychromatic beam of electromagnetic radiation which transmits through said beam splitting means. Said electromagnetic beam detecting means can be in functional combination with electronic circuitry means which serves to automatically align said portion of said polychromatic beam of electromagnetic radiation which is transmitted toward said ninth aperture and optical fiber, based on feedback from said detector.

The preferred detector dispersive optics and detector elements are contained in an off-the-shelf diode array spectrometer system, with an operational wavelength range selected from the group consisting of:
  150-400 nm;
  150-1000 nm;
  300-1150 nm;
  190-730 nm;
  190-400 nm;
  900-2400 nm;
  1000-1700 nm;

and optionally the detector which demonstrates a quantum efficiency of at least greater than forty (40%) percent.

The dispersive optics is preferably a diffraction grating characterized by a selection from the group consisting of:
  a "lined";
  a "blazed"; and
  a "holographic" geometry;

said lined geometry consisting essentially of symmetrical alternating lines with depressions therebetween, and said blazed geometry consisting of alternating ramp shaped lines with depressions therebetween, and said holographic geometry consisting of continuous cosine shaped lines and depressions. However, said dispersive optics can comprise a prism.

Compensators can also be of a type selected from the group consisting of:
  Berek-type with optical axis essentially perependicular to a surface thereof;
  non-Berek-type with an optical axis essentially parallel to a surface thereof;
  zero-order wave plate;
  zero-order waveplate constructed from two multiple order waveplates;
  a sequential plurality of zero-order waveplates, each constructed each from a plurality of multiple order waveplates;
  rhomb;
  polymer;
  achromatic crystal; and
  pseudo-achromatic.

Where a fiber optic present after said analyzer it can be single or at least bifrucated thereby providing a plurality of fiber optic bundles, at least two of which plurality of at least two bifrucated fiber optic bundles provide input to separate detector system), each of said separate detector systems comprising a dispersion optics and a multiplicity of detector elements, said plurality of fiber optic bundles having cross-sectional shapes at ends thereof selected from the group:
  essentially circular;
  essentially slit shaped;
  other than essentially circular; and
  essentially slit shaped.

It is also to be appreciated that the disclosed spectroscopic rotating compensator material system investigation system is characterized by a mathematical model comprising calibration parameters, at least one of which is a member of the group consisting of:
  effective polarizer azimuthal angle orientation ($P_s$);
  present material system PSI ($\psi$), as a function of angle of incidence and a thickness;
  present material system DELTA ($\Delta$), as a function of angle of incidence and a thickness;
  compensator azimuthal angle orientation ($C_s$) matrix components of said compensator;

analyzer azimuthal angle orientation ($A_s$); and detector element image persistence ($x_n$) and read-out ($p_n$) nonidealities.

Further, said mathematical model is effectively a transfer function which enables calculation of electromagnetic beam magnitude as a function of wavelength detected by a detector element (DE), given magnitude as a function of wavelength provided by said source of polychromatic beam of electromagnetic radiation (EPCLB). Said calibration parameter(s) selected from the group consisting of:

effective polarizer azimuthal angle orientation ($P_s$);

present material system PSI ($\psi$), as a function of angle of incidence and a thickness;

present material system DELTA ($\Delta$), as a function of angle of incidence and a thickness;

compensator azimuthal angle orientation;

matrix components of said compensator ($C_s$) as a function of wavelength;

analyzer azimuthal angle orientation ($A_s$); and detector element image persistence ($x_n$) and read-out ($p_n$) nonidealities;

are, in use, evaluated by performance of a mathematical regression of said mathematical model onto at least one, multi-dimensional, data set(s), said at least one, multi-dimensional, data set(s) being magnitude values vs. wavelength and a at least one parameter selected from the group consisting of:

angle-of-incidence of said polychromatic beam of electromagnetic radiation with respect to a present material system (MS); and effective or actual azimuthal angle rotation of one element selected from the group consisting of:

said polarizer (P); and said analyzer (A);

obtained over time, while said compensator (C) is caused to continuously rotate;

said at least one, multi-dimensional, data set(s) each being normalized to a selection from the group consisting of:

a data set D.C. component;

a data set A.C. component;

a parameter derived from a combinations of a data set D.C. component and a data set A.C. component.

Recent Developments

Continuing, as already noted, the present invention can be applied in an ellipsometer or polarimeter system comprising:

a) a source of electromagnetic radiation;

b) a polarizer;

c) a stage for supporting a sample;

d) an analyzer; and e) a detector;

said ellipsometer or polarimeter system further comprising at least one rotatable compensator system present at least one location selected from the group consisting of:

between said source of electromagnetic radiation and said stage for supporting a sample; and between said stage for supporting a sample and said detector;

said at least one rotatable compensator comprising at least two sequential elements oriented with respect to one another such that said entered electromagnetic beam undergoes total internal reflection at least once in each of the elements, with the sequence, orientation, geometry, and symmetry of the elements being such that the locus of the output beam is substantially undeviated from that of the input beam by a translation of the system, and the locus of the output beam angle is substantially undeviated from that of the input beam by a rotation of the system.

With that in mind, the present invention then comprises a system for introducing a relative phase retardation between orthogonal components of a polarized electromagnetic beam. Said system can consist of at least two sequential elements, and said beam undergoes total internal reflection at least once in each of said elements. Importantly, the sequence, orientation, geometry, and symmetry of the elements in the system is such that the locus of an exiting output beam is substantially undeviated from that of the input beam by a translation of the system, and the exiting output beam angle is substantially undeviated from that of the input beam by a rotation of the system.

One embodiment provides that two triangular shaped prisms comprise the elements. Preferred, non-limiting, design provides that the angles of said triangular prisms are 26, 128, and 26, and fabrication of the prisms can be, but is not necessarily, from fused silica.

Another embodiment provides that two parallelogram shaped rhombs are used for the elements. Preferred, non-limiting, design provides that angles of the parallelogram shaped rhombs are 36, 144, 36, and 144 degrees or 45, 235, 45 ans 235 degrees, and again, fabrication of the parallelogram can be, but is not necessarily, from fused silica.

Another embodiment provides that four right angle prisms are used for elements. Preferred, non-limiting, design provides that angles are 45, 90 and 45, and again, fabrication of the prism can be, but is not necessarily, from fused silica.

Further, at least one of the elements can comprise a mechanism for translating and/or tilting at least one of the elements with respect to another element, for the purpose of aligning the elements of the system so as to reduce deviation between the locus of an output beam as compared to that of a beam input to said system.

The present invention can comprise a system for introducing a relative phase retardation into orthogonally polarized components of an electromagnetic beam entered thereinto, said system consisting of at least two sequential elements oriented with respect to one another such that said entered electromagnetic beam undergoes total internal reflection at least once in each of the at least two elements;

the sequence, orientation, geometry, and symmetry of the elements being such that the output beam position is substantially undeviated by a translation of the system, and the output beam angle is substantially undeviated by a rotation of the system.

The elements can be similar triangular shaped prisms each having:

first and second sides of equal length which project from one another at an angle greater than ninety degrees therebetween, and a third side oriented opposite said greater than ninety degree angle, said at least two similar triangular shaped prisms being oriented with respect to one another such that the third sides thereof are substantially colinear;

such that a beam of electromagnetic radiation caused to enter the first side of the first thereof, at a non-normal angle thereto, is refracted so that it internally reflects from said third side thereof, then exits said second side thereof in a direction such that it then enters the first side of another thereof at a non-normal angle thereto, is refracted so that it internally reflects from said third side thereof, then exits said second side thereof. The angles of the triangular prism can be 26, 128, and 26 degrees and the prisms can be fabricated from of fused silica, $MgF_2$ $CaF_2$ etc.

The elements can be parallelogram shaped rhombs, each said rhomb having first, second, third and forth sides, said first and third sides being parallel to one another and said second and forth sides being parallel to one another, said first and second, and said third and forth sides meeting of the first parallelogram shaped rhomb meeting one another at angles greater than ninety degrees therebetween, and said second and third sides and said first and forth sides thereof meeting one another at angles less than ninety degrees therebetween with the second parallelogram shaped rhomb being positioned as a mirror image thereto, said at least two parallelogram shaped rhombs being oriented with their second sides being substantially colinear and with their forth sides thereof being substantially colinear;

such that a beam of electromagnetic radiation caused to enter the first side of the first thereof, at a non-normal angle thereto, is refracted so that it internally reflects from said forth and second sides thereof, then exits said third side thereof in a direction such that it then enters the first side of the second thereof at a non-normal angle thereto, is refracted so that it internally reflects from said second and forth side thereof, then exits said third side thereof. The angles of the parallelogram shaped rhomb can be 36, 144, 36, and 144 degrees or 45, 135, 45 and 135 degrees, and can be fabricated from of fused silica.

The elements can be rhombs, each said rhomb having first, second, third and forth sides, said first and third sides being parallel to one another and said second and forth sides being parallel to one another, said first and second, and said third and forth sides of the first meeting one another at angles greater than ninety degrees therebetween, and said second and third sides and said first and forth sides of the first rhomb meeting one another at angles less than ninety degrees therebetween, with the second rhomb appearing as a mirror image;

said at least two parallelogram shaped rhombs being oriented with their first and third sides being substantially parallel to one another;

such that a beam of electromagnetic radiation caused to enter the first side of the first thereof, at substantially a normal angle thereto, then proceeds so that it internally reflects from said forth and second side thereof, then exits said third side thereof in a direction such that it then enters the first side of another thereof at a substantial normal angle thereto, then proceeds so that it internally reflects from said second and forth side thereof, then exits said third side thereof;

said system being characterized in that at least one of the sides of at least one of the parallelogram shaped rhombs has a coating thereupon which has a different, (eg. lower), refractive index than does the material from which said corresponding parallelogram shaped rhomb is comprised. The angles of the parallelogram shaped rhomb can be 36, 144, 36, and 144 degrees or 45, 135, 45 and 135 degrees, and the rhombs can be fabricated from of fused silica, with the coating being $MgF_2$.

The elements can be at least four sequential elements, said beam undergoing total internal reflection once in each of the elements, said system being characterized in that each of said at least four elements are right angle prisms having right angle sides adjacent to the right angle thereof and a side opposite the right angle thereof; said right angle prisms being oriented with respect to one another such that, as viewed in side elevation, the first right angle prism is positioned so that its side opposite the right angle thereof is facing downward and to the right, and so that directly above the first right angle prism is present the second right angle prism, which is oriented so that its side opposite the right angle thereof is facing upward and to the left, and so that directly to the right of the second right angle prism is the third right angle prism, which is oriented so that its side opposite the right angle thereof is facing upward and to the right, and so that directly below the third right angle prism is positioned the forth right angle prism, oriented so that its side opposite the right angle thereof is facing downward and to the left. The angles of the right angle prisms can be 45, 90 and 45 degrees and the right angle prisms can be fabricated from of fused silica.

As recited above, any of the foregoing embodiments can be further characterized by at least one selection from:
at least one of the sequential elements has a mechanism for translating and/or tilting the element, for the purpose of aligning the system such that the output beam is substantially undeviated from said input beam;
at least one of the sequential elements has a coating upon a surface thereof at which internal reflection of a beam of electromagnetic radiation occurs, said coating having a different refractive index than does the material from which said corresponding element is comprised;
at least one of the sequential elements has a coating upon a surface thereof through which a beam of electromagnetic radiation enters or exist, said coating having a different refractive index than does the material from which said corresponding element is comprised;
there is present an additional sequential multiple wedge system in said system for introducing a relative phase retardation into orthogonally polarized components of an electromagnetic beam, wherein one said wedge can be rotated with respect to another thereof and/or both wedges can be rotated simultaneously, for the purpose of aligning the system such that the output beam is substantially undeviated from said input beam;

A present invention method involves providing a compensator system comprising at least two elements oriented with respect to one another such that an entered electromagnetic beam undergoes total internal reflection at least once in each of the elements, with the sequence, orientation, geometry, and symmetry of the elements being such that the locus of output beam from said system is substantially undeviated from that of the input beam by a translation of the system, and the locus of the output beam angle is substantially undeviated from that of the input beam by a rotation of the system;

said method comprising the steps of:

a) providing a system for introducing a relative phase retardation into orthogonally polarized components of an electromagnetic beam, said system comprising of at least two sequential elements, said beam undergoing total internal reflection at least once in each of the elements;

b) causing a beam of electromagnetic radiation to enter said system via a first of said at least two sequential elements pass through said at least two sequential elements while undergoing at least one total internal reflection in each;

such that the exiting beam has retardation entered thereinto via said internal reflections, and such that the locus of the exiting beam is substantially undeviated from that of the entering beam.

A coating can be provided on at least one surface of at least one of element, said coating having a refractive index less than or greater than that of the material from which said element is comprised.

Said method can further comprise providing an additional sequential multiple wedge system in said system, wherein one said wedge can be rotated with respect to another thereof and/or both wedges can be rotated simultaneously, for the purpose of aligning the system such that the output beam from said forth right angle prism is substantially undeviated from the beam input to said first right angle prism.

At this point it is beneficial to recite a method of quickly simultaneously taking data at a multiplicity of wavelengths including wavelengths which are, and are not absorbed by environmental components. Said method comprises the steps of:

a) providing a spectroscopic ellipsometer or polarimeter system comprising a source of a polychromatic beam of electromagnetic radiation, a polarizer, a stage for supporting a material system, an analyzer, a dispersive optics and at least one detector system which comprises a multiplicity of detector elements;

such that when said spectroscopic ellipsometer or polarimeter is used to investigate a material system present on said stage for supporting a material system, a polychromatic beam of electromagnetic radiation produced by said source of a polychromatic beam of electromagnetic radiation is caused to pass through said polarizer and interact with a material system on said stage for supporting a material system, then pass through said analyzer, and interact with said dispersive optics such that a multiplicity of essentially single wavelengths are caused to simultaneously enter a corresponding multiplicity of detector elements in said at least one detector system;

said spectroscopic ellipsometer or polarimeter system further comprising an environmental control chamber in which the spectroscopic ellipsometer or polarimeter is contained, said environmental control chamber being characterized by a selection from the group consisting of:

it comprises at least one chamber region in which is present polarization state generator comprising component(s) prior to said material system and polarization state detector comprising component(s) after said material system, and optionally said material system;

it comprises at least three chamber regions, in one of which is present polarization state generator comprising component(s) prior to said material system, in the second of which is present the material system and in the third of which is present polarization state detector comprising component(s) after said material system;

it comprises at least two chamber regions, in one of which is present polarization state generator comprising component(s) prior to said material system and said material system, and in the second of which is present polarization state detector comprising component(s) after said material system;

it comprises at least two chamber regions, in one of which is present polarization state generator comprising component(s) prior to said material system, and in the second of which is present polarization state detector comprising component(s) after said material system and said material system.

b) placing a material system on said stage for supporting a material system and at least partially purging or evacuating said environmental control chamber;

c) causing said source of polychromatic beam of electromagnetic radiation to provide a polychromatic beam of electromagnetic radiation and causing said beam to interact with said material system on said stage for supporting a material system, and interact with said dispersive optics such that a multiplicity of essentially single wavelengths are caused to simultaneously enter a corresponding multiplicity of detector elements in said at least one detector system.

Said method of quickly simultaneously taking data at a multiplicity of wavelengths can involve providing at least one detector system which comprises a multiplicity of detector elements involves providing a one-dimensional array or a multi-dimensional array.

Further, it is generally known that many sources of electromagnetic radiation which provide wavelengths down to and below 193 nm typically provide said wavelengths at a lower intensity than is associated with longer wavelengths. Also, it is known that optical elements through which electromagnetic radiation is caused to pass often have different effects on different wavelengths, with a result being that electromagnetic radiation of one wavelength proceeds along a different path than does electromagnetic radiation of a different wavelength. Where said electromagnetic radiation is to be focused onto a spot on a sample said dispersion can lead to the spot being of a diameter greater than 35 micron. Disclosed in this Specification are a number of approaches to improving intensity at short wavelengths and of reducing spot size of electromagnetic radiation where it is caused to impinge upon a sample surface.

A first approach is to provide a back reflector behind a source of electromagnetic radiation, which serves to direct electromagnetic radiation which exits the source in a useful direction.

Another approach is to provide a reflecting means in the pathway of the electromagnetic beam, upon which reflecting means is a coating which emphasises reflection of the UV and particularly at 193 nm. An example of such a coating on a reflective means is 600 Angstroms of Silicon Dioxide atop Silicon. This approach enables setting "gain" providing means at higher levels to emphasize UV signals, while not over amplifying, and even saturating higher intensity wavelengths signals.

Another approach is to coat transmissive elements such as lenses present in the system, to minimize entry and exit losses caused thereby, and improve overall UV transmission therethrough. An example is a single 300 Angstrom layer of $MgF_2$. Multi layer coatings can also be used.

Another approach is to provide a Grating which has characteristics that emphasize UV wavelengths and/or direct a utilized "Order" of wavelengths in a direction which is subject to less influence by the zero and/or other orders.

Further, application of baffling to block access of zero and/or other orders of electromagnetic radiation to detector means can be applied.

Approaches which focus on optical fibers are:

Another approach is to eliminate optical fibers which, while convenient for use directing electromagnetic radiation, also serve to attenuate UV wavelength intensity via entry loss and transmission attenuation.

However, if optical fibers are utilized, to reduce UV intensity at fiber entry loss a narrow slit (eg. smaller that the fiber dimension), can be placed at the entry to the fiber.

The following approaches focus on increasing the amount of UV electromagnetic radiation and can be practiced independently or in combination:

Another approach is to utilize a source of electromagnetic radiation which emphasises UV wavelength production.

Various wattage lamps (eg. 35, 75 and 150 can be applied and where necessary can involve application of various indirect heat sink based cooling and produced ozone containment.

Another approach is to, in the case of rotating compensator ellipsometers, reduce the rotation speed of the compensator so that for the same number of rotations more total electromagnetic radiation passes therethrough and reaches the detector.

Another approach is to take multiple scans of data to improve signal to noise.

Another approach is to combine the output of multiple pixels in a detector which receive UV radiation.

An approach which is focused on providing a small spot size, (eg. 35 μn), is to identify optical elements which enter dispersion of wavelengths entered thereinto and reduce their effect. Dispersion, it should be appreciated causes different wavelengths in electromagnetic radiation to focus at different points on a sample. Reduced dispersion can be accomplished by, for instance, adding optical elements which offset the effect entered by existing optical elements. While increasing physical dimensions and potentially adding entry and exit and transmission attenuation effects, the result can be a smaller spot size.

The disclosed invention can also comprise a system for providing ultraviolet wavelength electromagnetic radiation which comprises a UV source chamber within which is an enclosed space. The enclosed space contains a source lamp which when electrically energized produces ultraviolet wavelength electromagnetic radiation. Said UV source-chamber further has means for allowing produced ultraviolet radiation to exit as a collimated beam. Said system further comprises means for providing electrical potential to said-source lamp, heat transfer means which is situated to accept heat from said source lamp and conduct it to outside said enclosed space to a heat sink and a gas flow production means for causing said flow of gas over said heat sink. In use voltage is applied to said lamp source by said means for providing electrical potential to said source lamp and heat and ultraviolet wavelength electromagnetic radiation and ozone are produced thereby. At least some of said heat is conducted by said heat transfer means to said heat sink and is dissipated by a gas flow therearound, which is produced by said gas flow production means. Simultaneously at least some of said ultraviolet wavelength electromagnetic radiation is caused to exit said means for allowing produced ultraviolet radiation as a collimated beam. Importantly, this approach to cooling provides that produced ozone is safely contained within said enclosed space and nearby personnel are therefore not exposed thereto.

In ellipsometry applications, for instance, said system further comprises a polarizer in the pathway of said collimated beam of electromagnetic radiation, which polarizer can be selected from the group consisting of:

Calcite;

BBO;

MgFl;

MgF$_2$ and CaF$_2$;

to impose a state of substantially linear polarization thereupon In wavelength ranges of from above 1100 nm to about:

245 nm;

220 nm;

193 nm;

150 nm.

respectively.

A preferred means for allowing produced ultraviolet radiation to exit as a collimated beam comprises a pin hole and lens means present inside a protective tube which serves to prevent air flow by said lens means.

As a specific example, the source lamp can be a Xenon bulb, and the voltage applied thereto 20 KV. A realized embodiment has been determined to, during operation, cause said Xenon Lamp temperature rises to about 200 degrees C., the heat sink to about 65 degrees C., and the exterior of said chamber to no more than about 50 degrees C. during use.

Finally, it is noted that concrete and tangible effects can be realized by applying signals developed by a detector in a spectroscopic ellipsometer or polarimeter system, by at least one selection from the group consisting of:

storing at least some data provided by said data detector in machine readable media;

analyzing at least some of the data provided by said data detector and storing at least some of the results of said analysis in machine readable media;

displaying at least some data provided by said data detector by electronic and/or non-electronic means;

analyzing at least some of the data provided by said data detector and displaying at least some of the results of said analysis by electronic and/or non-electronic means;

causing at least some data provided by said data detector to produce a signal which is applied to provide a concrete and tangible result;

analyzing at least some of the data provided by said data detector and causing at least some thereof to produce a signal which is applied to provide a concrete and tangible result.

The present invention will be better understood by reference to the Detailed Description Section of this Specification, in combination with reference to the Drawings.

BRIEF DESCRIPTION OF THE DRAWINGS

FIG. 1a shows the basic components of reflectance and transmission mode material system investigation systems.

FIG. 1b1 shows the components of a reflectance mode material system investigation systems which has five apertures in the pathway of an electromagnetic beam prior to a material system, and four thereafter.

FIG. 1b2 shows the components of a reflectance and tranmittance mode material system investigation systems which has focusing lenses.

FIG. 1c demonstrates an environmental chamber into which systems such as demonstrated in FIGS. 1a, 1b1 and 1b2 systems can be present.

FIG. 1d demonstrates an entire ellipsometer or polarimeter in an environmental chamber (CHA).

FIGS. 1e and 1f demonstrate one and multi-dimensional detectors (DET) comprising a multiplicity of detector elements (DE's).

FIG. 2 shows a spectrographic diode array spectrometer system detector.

FIGS. 9g1, 9h and 9i demonstrates construction of a preferred compensator system constructed from first and second effective zero-order waveplates, each of which effective zero-order waveplates is a constructed composite of two multiple order waveplates, the fast axes of which at least two composite effective zero-order waveplates are oriented away from zero or ninety degrees, and at a nominal forty-five degrees, with respect to one another. Optional additional third element(s) are indicated by dashed lines.

FIG. 9g2 shows three zero order plates are contacted to one another instead of having space thereinbetween. Three element compensators configured as suggested by FIGS. 9g1, 9g2 and 9j can comprise a "psuedo achromatic" which can provide retardation vs. wavelength characteristics such as those presented in FIG. 10g2.

FIG. 9j demonstrates functional construction of another preferred compensator system constructed from first and second actual per se. zero-order waveplates, each of which actual per se. zero-order waveplate is an effective single plate, the fast axes of which at least two composite actual per se. zero-order waveplates are oriented away from zero or ninety degrees, and at a nominal forty-five degrees, with respect to one another.

FIGS. 9k1-9q demonstrate additional compensators which can be applied in the present invention.

FIGS. 10f and 10g1 show that changing waveplate selection for a FIG. 9g1 compensator configuration, and the angle between fast axes thereof, provides alternative retardation plots over various wavelength ranges.

FIG. 10g2 shows retardation vs. wavelength for a three (3) zero order plate compensator. The retardation varies between about 47 degrees and 130 degrees over a wavelength range of 190 to 1700 nm. Said three (3) element compensator comprises a 422 nm quartz zero order waveplate sandwiched by two 633 nm quartz zero order waveplates. FIGS. 9g1 and 9j, wherein the dashed lines represent a present third waveplate, demonstrate the physical realization.

FIG. 14a shows a typical ¼ Wave 90 degree retardance Fresnel rhomb and demonstrates the translation effect.

FIG. 14b shows how two Fresnel rhombs can be combined to result in a non-deviated beam.

FIG. 15 shows two triangular isosceles prisms, with angles of 26, 128, and 26 degrees.

FIG. 16 shows two parallelogram rhombs, with angles of 36, 144, 36, and 144 degrees.

FIGS. 17a, 17b, 18a and 18b show that if the elements are translated up or down, the exiting beam is unchanged.

DETAILED DESCRIPTION

Invention System

Figure 3:
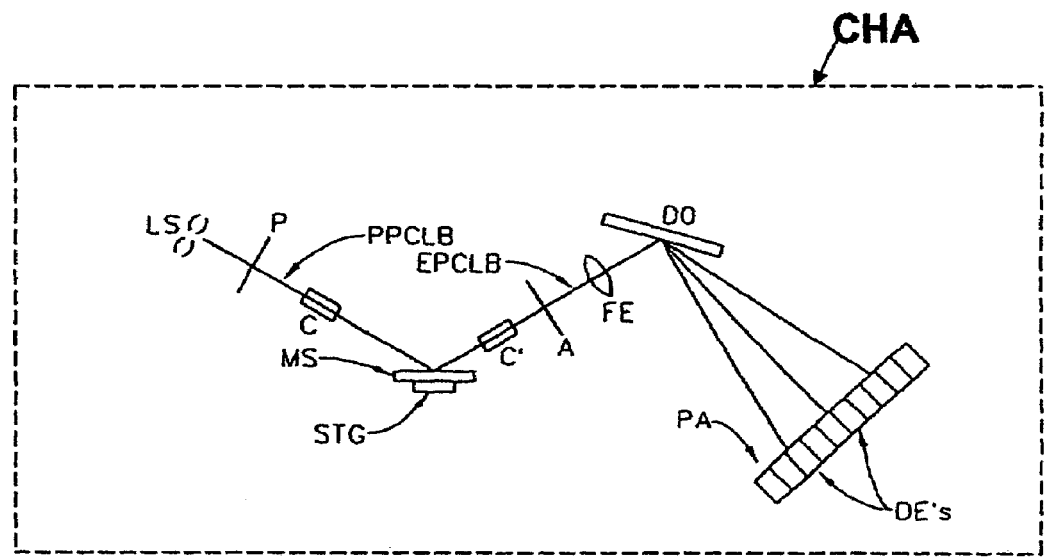
FIG. 3 shows a reflectance mode combination of components shown in FIGS. 1a and 2.

Referring now to FIG. 1a, there is demonstrated a Material System Investigation System, (ie. a Spectroscopic Ellipsometer System), with provision to investigate a Material System (MS) in either a Reflection Mode (RM) or a Transmission Mode (TM). It is to be noted that said Material System investigation System is generally comprised of a Source of a Polychromatic Beam of Electromagnetic Radiation (LS), (ie. a Broadband electromagnetic radiation source), a Polarizer Means (P), a Material System, supporting Stage (STG), an Analyzer Means (A) and a Detector Elements (DE's) containing Photo Array Detector Means System (DET). Also note, however, that FIG. 1a shows Reflection Mode System Compensator(s) Means (C) and (C') and Transmission Mode System Compensator(s) Means (C) and (C") as present. It is to be understood that a Compensator Means can be placed ahead of, and/or after a Material System (MS) supporting Stage (STG) in either a Reflection Mode or Transmission Mode System. That is only Compensator Means (C) or (C') or both Compensator Means (C) and (C') can be present in a Reflection Mode System (RM), and only Compensator Means (C) or (C") or both Compensator Means (C) and (C") can be simultaneously present in the Transmission Mode System (TM). FIG. 1a also shows the presence of a Processor (PS) for performing calculations that evaluate a sample based on the Detector (DET) intensity output signal. Note that the indicated processor (PS) is not programmed with the same type of algorithm the processor in the Aspnes et al. Patents is interpreted as containing.

Now, the configuration in FIG. 1a could be operated as a Rotating Polarizer or Rotating Analyzer System. The disclosed Rotating Compensator Material System Investigation System, however, in the preferred operational mode, essentially fixes the Polarizer Means (P) and Analyzer Means (A) during Data Acquisition from a Material System (Sample) (MS) which is placed upon the Material System supporting Stage (STG), and causes at least one present Compensator Means ((C), and/or (C') or (C) and/or (C")), to Rotate during said Data Acquisition. This serves to effectively enter a continuously varying retardance between Orthogonal Components in a Polarization Beam of Electromagnetic Radiation exiting said Compensator Means which is caused to rotate. Where two (2) Compensator Means are present, one before (C) and one after ((C') or (C")) a Material System placed upon said Material System (MS) supporting Stage (STG), only one, or both said Compensator Means can be caused to Rotate in use. If both Compensator Means are caused to rotate, both can be rotated the same rotation speed, or different rotation speeds can be utilized. It is noted that the J. A. Woollam CO. Rotating Compensator Ellipsometer can use a Stepper Motor, a Servo Motor or Three Phase Synchronous Motor to cause Compensator rotation, and a common signal can synchronizes both the Compensator and Detector. An alternative technique is to use a signal derived from the motor to synchronize the detector. It is further noted that fixing the Polarizer Means (P) and Analyzer Means (A) during data acquisition provides another benefit in that polarization state sensitivity to input and output optics during data acquisition is essentially non-existent. This allows use of Optic Fibers, Mirrors, Beam Splitters, Lenses etc. for input/output.

FIG. 1b1 shows a spectroscopic rotating compensator material system investigation system comprising a source (LS) of polychromatic beam of electromagnetic radiation, a first aperture (A1), a second aperture (A2), a fixed polarizer (P), a rotating compensator (C), a third aperture (A3), a forth aperture (A4), a first substantially achromatic lens (AL1), a fifth aperture (A5), a stage (STG) for supporting a material system, a sixth aperture (A6), a second substantially achromatic lens (AL2), a seventh aperture (A7), an eighth aperture (A8), a fixed analyzer (A), a ninth aperture (A9), a third substantially achromatic lens (AL3), an optical fiber (OF) and a detector system (DET) which contains a dispersive element and a multiplicity of detector elements, there further being a UV filter (F1) present between said source (LS) of polychromatic beam of electromagnetic radiation and said stage (STG) for supporting a material system. When said spectroscopic rotating compensator material system investigation system is used to investigate a material system (MS) present on said stage (STG) for supporting a material system, said fixed analyzer (A) and fixed polarizer (P) are maintained essentially fixed in position and said rotating compensator (C) is caused to continuously rotate while a polychromatic beam of electromagnetic radiation produced by said source (LS) of a polychromatic beam of electromagnetic radiation is sequentially caused to pass through said first aperture (A1), second aperture (A2), fixed polarizer (P), rotating compensator (C), third aperture (A3), forth aperture (A4), first substantially achromatic lens (AL1), fifth aperture (A5), said polychromatic beam of electromagnetic radiation also passing through said UV filter, then interact with a material system (MS) placed on said stage (STG) for supporting a material system (MS), then sequentially pass through said sixth (A6) aperture, second substantally achromatic lens (AL2), seventh aperture (A7), eighth aperture (A8), fixed analyzer (A), ninth aperture (A9), third substantially achromatic lens (AL3), optionally pass through another aperture and, then enter said optical fiber (OF) and therevia enter said detector system (DET).

FIG. 1b2 shows that a present invention ellipsometer or polarimeter system, for each of a Reflection and Transmission mode, can comprise:
 a) a source (LS) of electromagnetic radiation;
 b) a polarizer (P);
 c) a stage (STG) for supporting a sample (MS);
 d) an analyzer (A); and
 e) a detector (DET);

said ellipsometer or polarimeter system further comprises at least one rotatable compensator (C) (C') (C") present at least one location selected from the group consisting of:
 between said source (LS) of electromagnetic radiation and said stage (STG) for supporting a sample (MS); and
 between said stage (STG) for supporting a sample (MS) and said detector (DET);

said at least one rotatable compensator (C) (C') (C") comprising at least two sequential elements oriented with respect to one another such that said entered electromagnetic beam undergoes total internal reflection at least once in each of the elements, with the orientation, geometry, and symmetry of the elements being such that the output beam position is undeviated by a translation of the system, and the output beam angle is undeviated by a rotation of the system. Again, one embodiment provides that two triangular shaped prisms are used for the elements. Preferred design provides that the angles of the triangular prisms are 26, 128, and 26 degrees. Another embodiment provides that two parallelogram shaped rhombs are used for the elements. Preferred design provides that angles of the parallelogram shaped rhombs are 36, 144, 36, and 144 degrees. Also, as mentioned other embodiments can include one or more triangular shaped prisms and one or more parallelogram shape rhombs etc. Further, at least one of the elements can have a mechanism for translating and/or tilting at least one of the elements, for the purposes of aligning the system such that the locus of the exiting beam is substantially undeviated in position and angle from the locus of the input beam. Fabrication of the compensator can be from fused silica, $CaF_2$, $MgF_2$ etc.

It is also mentioned that in the following it will be generally assumed that a Material System (MS) under investigation by a Spectroscopic Rotating Compensator Material System Investigation System is positioned upon the Material System Supporting Stage (STG). This need not be the case, as is described in U.S. Pat. No. 5,706,087 wherein a Material System (Sample), (MS) can be positioned in a Magneto-optic System which is physically too large to be supported by said Material System Supporting Stage (STG), or in an environmental control chamber. Further, especially where Ultraviolet range wavelengths are utilized, the system of FIG. 1a, 1b1 or 1b2 can be placed into an evacuated or purged, (eg. by nitrogen or argon), Chamber to the end that UV absorbing Oxygen and Water Vapor are not present therewithin. The entire FIG. 1a, 1b1 or 1b2 system can be so encompassed within a said Chamber, or only the Sample (MS) Stage portion thereof. The Chamber can be of multiple region construction. FIG. 1c shows a Chamber (CHA) which can be interpreted to contain one or multiple interior regions and FIG. 1d shows a one region-environmental control chamber (CHA). For Instance the FIG. 1a Pre-(MS) Polarization State Generator (PSG) and Post-(MS) Polarization State Detector (PSD) can be open to the region containing the Material System (MS), or can be considered to be sequestered by (AC1) and (AC2) so that the internal environments available to each can be controlled to be are the same or different. More specifically, the environmental chamber can have a configuration characterized by a selection from the group consisting of:

it comprises at least one chamber region in which is present polarization state generator (PSG) comprising component(s) prior to said material system and polarization state detector (PSD) comprising components after said material system, and optionally also contains said material system (MS);

it comprises at least three chamber regions, in one of which is present polarization state generator (PSG) comprising component(s) prior to said material system (MS), in the second of which is present the material system (MS) and in the third of which is present polarization state detector (PSD) comprising component(s) after said material system (MS);

it comprises at least two chamber regions, in one of which is present polarization state generator (PSG) comprising component(s) prior to said material system (MS) and said material system (MS), and in the second of which is present polarization state detector (PSD) comprising component(s) after said material system MS;

it comprises at least two chamber regions, in one of which is present polarization state generator comprising component(s) prior to said material system, and in the second of which is present polarization state detector comprising component(s) after said material system and said material system.

Note that the FIG. 1c Chamber is to be interpreted to optionally allow the Sample (SS) to be sequestered. The environment in any chamber region can be individually controlled, or the environment in all chamber regions can be similarly controlled. This includes allowing the chamber regions containing the polarization state generator (PSG) and the polarization state detector (PSD) to be in ambient with only a material system (MS) under investigation being in a Controlled Environment (SES). The functional purpose is to avoid attenuation of wavelengths (eg. UV) by the presence of oxygen or water vapor etc.

FIG. 1d demonstrates an entire ellipsometer or polarimeter in an Environmental Chamber (CHA). Shown in a Controlled Environment (SES), prior to a Stage (STG) with a Sample (MS) present thereupon, are a Source of a Beam (PPCLB) of Electromagnetic Radiation (LS), a Polarizer, a Compensator (C). Alos shown are Reflection (RM) and Transmission (TM) Mode sequences of Compensator (C') (C"), Analyzer (A) and Detector (DET) into each of which is shown entering an Electromagnetic Beam (EPCLB). FIGS. 1e and 1f demonstrate that the Detector (DET) preferably comprises multiple Detector Element (DE's), as shown in FIGS. 2, 3, 4 and 5a, (any of which can likewise be in an environmental chamber (CHA)). This can be of particular benefit where speed of data acquisition is important as it allows multiple wavelengths to be simultaneously detected.

Continuing, as alluded to, the disclosed invention utilizes a Broadband source of Polychromatic Electromagnetic Radiation (LS), and FIG. 2 shows that the Detector Elements (DE's) containing Detector System (DET) is, in the preferred embodiment, comprised of a Photo Array which consists of a number of Diode Elements (DE's), (any functionally equivalent, though structurally different, Detector Element (DE's) are to be considered equivalent for the purposes of Claim construction). In use a Dispersive Optics (DO) receives a Polychromatic Electromagnetic Beam (EPCLB) which has interacted with a Material System (MS) and passed through said Analyzer Means (A), and diffracts said Polychromatic Electromagnetic Beam (EPCLB), such that each Photo Array (PA) Diode Element (DE) intercepts an Essentially Single Wavelength, (eg. a small band of wavelengths centered about a central single wavelength). Note that a Focusing Element (FE) is shown in a dashed line format to indicate that its presence is optional. The Focusing Element (FE), when present, serves to provide a focused Polychromatic Beam of Electromagnetic Waves at the input to said Detector Elements (DE's) containing Photo Array Detector System (DET), and the Detector. System (DET) provides 2ω and 4ω signals developed by the Diode Elements (DE's) in a sequential output or a parallel output from the Diode Elements (DE's). It is emphasized that a preferred Detector Elements (DE's) containing Photo Array Detector System (PET) can be an "Off-the-Shelf-System" which includes a Focusing Element (FE), and provides a self contained Dispersive Optics (DO) and Diode Element (DE) Array. One "Off-The-Shelf-System" of said preferred embodiment of the Rotating Compensator Material System Investigation System is a Zeiss Diode Array Spectrometer System identified by manufacturer numbers in the group: (MMS1 (300-1150 nm); UV/VIS MMS (190-730 nm); UV MMS (190-400 nm); AND IR MMS (900-

2400 nm)). Said identified Zeiss systems provide a very compact system comprising a multiplicity of Detector Elements (DE's), and provide focusing via a Focusing Element (FE), Slit (S), and single concave holographic grating dispersive optics (DO), as generally represented by FIG. 2. A Hamamatsu CCD Array Detector, (Series S7030/S7031), with a quantum efficiency of 40% or more has been successfully utilized.

Note that FIG. 2 also shows the presence of a Beam Splitter (BS) and a Cross Hair containing Reticule (CH) in the Detector Elements (DE's) containing Photo Array Detector System (DET). If the Beam Splitter (BS), the Dispersive Optics (DO), the Focusing Element (FE), the Detector Elements (DE's) containing Photo Array (PA), and the Cross Hair containing Reticule (CH) are mounted so as to move as a rigid unit, then it should be appreciated that causing an Alignment Electromagnetic Radiation Beam (ALB) which reflects to said Cross Hair containing Reticule (CH) to be present near a Cross Hair crossing point can effect good alignment of the Detector Elements (DE's) containing Photo Array Detector System (DET) with respect to an entering Polarized Beam of Electromagnetic Radiation (EPCLB). In practice such an arrangement has been found to work very well. It is further noted that the element identified as (CH) could represent a Quadrature Photodetector and Automatic Alignment Means, or other functionally suitable system.

Figure 8A:
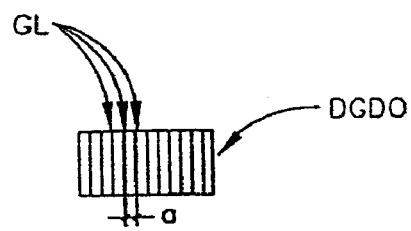
FIG. 8a shows lined diffraction grating dispersion optics geometry.
Figure 8B:
FIG. 8b shows a blazed angle lined diffraction grating dispersion optics geometry.
Figure 8C:
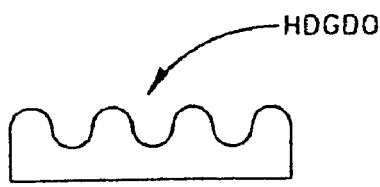
FIG. 8c shows a holographic lined diffraction grating dispersion optics geometry.
Figure 8D:
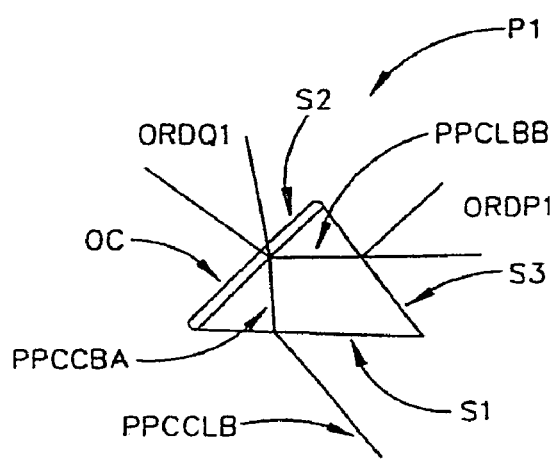
FIG. 8d shows a prism dispersion optics geometry.
Figure 9A:
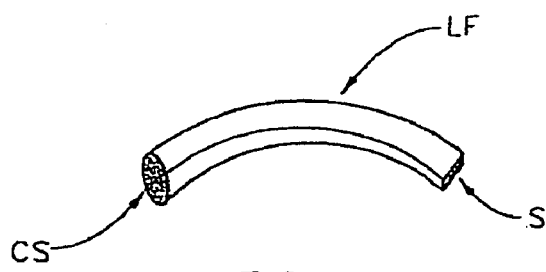
FIG. 9a shows a fiber optic which is essentially circular at the left side and which becomes of a "slit" shape at the right side.
Figure 9B:
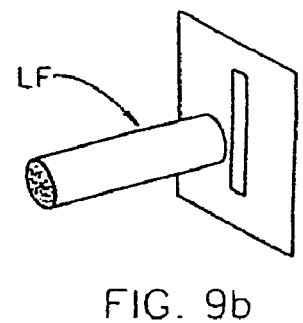
FIG. 9b shows a fiber optic which is essentially circular shaped along the entire length thereof, and which provides input to a "Slit" per se.
Figure 9C:
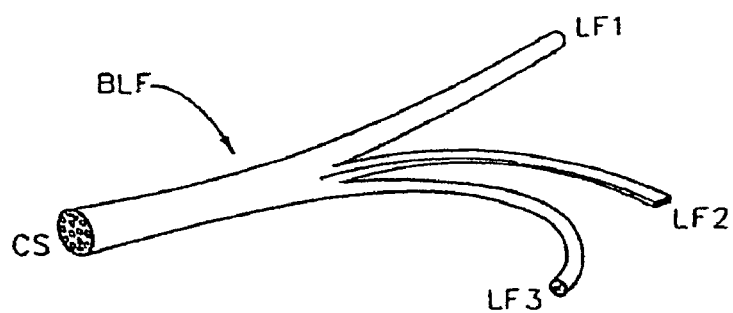
FIG. 9c shows a trifrucated fiber optic which is essentially circular at the left side, which trifrucates and then is exemplified as becoming circular or of a "slit" shape at the right side.
Figure 9D:
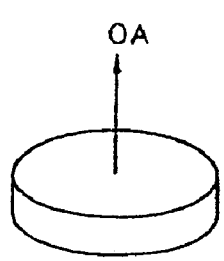
FIG. 9d shows a Berek-type compensator with an optical axis perpendicular to a surface thereof.
Figure 9E:
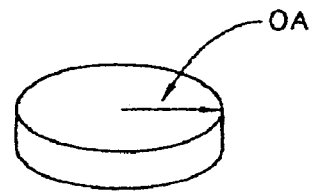
FIG. 9e shows a compensator with an optical axis parallel to a surface thereof.
Figure 9F:
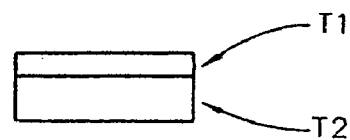
FIG. 9f demonstrates construction of a zero-order quartz waveplate from two multiple order waveplates.

It is also noted that a Compensator Means (C) (C'), (C") can utilize an Off-the-Shelf Quarter-Wave-Plate with its Optical Axis in the plane of a surface thereof, (see FIG. 9*e*), and that a Pseudo-Zero-Order Waveplate can be constructed from two (2) Multiple-Order Waveplates of different thicknesses (T1) and (T2) which have Optical Axes oriented Ninety (90) degrees to one another, such that the overall effect of retardation is in the Zero-Order, (see FIG. 9*f*). As discussed in more detail below, FIGS. 9*g*1-9*j* show that a particularly relevant Compensator Means involves a combination of two compensators means, each selected from the group consisting of: (actual or pseudo Quarter-Wave-Plates). Also, a Berek-type Compensator with its Optical Axis perpendicular to a surface thereof, (see FIG. 9*d*), can be is selected without special concern to its Achromatic Operating Characteristics, emphasis added. As well, said Compensator Means (C), (C'), (C") can be made of essentially any functional material such as Quartz or Polymer etc.

FIGS. 9*g*1, 9*h* and 9*i* demonstrate functional construction of a preferred compensator means system constructed from first (ZO1) and second (ZO2) effectively Zero-Order, (eg. Quartz or Bicrystalline Cadmium Sulfide or Bicrystalline Cadmium Selenide), Waveplates, each of which effective Zero-Order Waveplates (ZO1) & (ZO2) is shown to be constructed from two Multiple Order waveplates, (ie. (MOA1) & (MOB1) and (MOA2) & (MOB2), respectively). The fast axes (FAA2) & (FAB2) of said second effective Zero-Order Waveplate (ZO2) are oriented away from zero or ninety degrees, (eg. in a range around a nominal forty-five degrees such as between forty and fifty degrees), with respect to the fast axes (FAA1) & (FAB1) of said first effective Zero-Order Waveplate (ZO1). In particular FIG. 9*g*1 is a cross-sectional side view of a preferred compensator (PC) constructed from a first effective zero-order plate (ZO1) which is constructed from two multiple order plates (MOA1) and (MOB1), and a second effective zero-order plate (ZO2) which is constructed from two multiple order plates (MOA2) and (MOB2). An entered electromagnetic beam (EMBI) emerges as electromagnetic beam (EMBO) with a retardation entered between orthogonal components thereof with a Retardation vs. Wavelength such as demonstrated in FIGS. 15*a*-15*e*. FIGS. 9*h* and 9*i* are views looking into the left and right ends of the preferred Compensator Means (PC) as shown in FIG. 9*g*1, and show that the Fast Axes (FAA2) and (FAB2) of the second effective Zero-Order Waveplate (ZO2) are rotated away from zero or ninety degrees and are ideally oriented at forty-five degrees, with respect to the Fast Axes (FAA1) & (FAB1) of the first effective Zero-Order Waveplate (ZO1). (Note that the fast axis (FAA1) of the first effective Zero-Order Waveplate (ZO1) is shown as a dashed line in FIG. 9*i*, for reference). FIG. 9*j* demonstrates functional construction of another preferred compensator which is constructed from two per se. single plate Zero-Order Waveplates (MOA) and (MOB), which are typically made of materials such as mica or polymer. Note, It is to be understood that the space between retarder plates in FIGS. 9*g*1 and 9*j* can be reduced from that shown, even to the point where said retarder plates make contact with one another. Hence the presence of the spatial separation of the retarder plates shown in FIGS. 9*g*1 and 9*j* is not to be interpreted as indicating a required limitation. FIG. 9*g*2 shows three Zero Order Plates are contacted to one another instead of having space thereinbetween. Three element Compensators configured as suggested by FIGS. 9*g*1, 9*g*2 and 9*j* can comprise a "Psuedo Achromatic" which can provide Retardation vs. Wavelength characteristics such as those presented in FIG. 10*g*2. (See discussion of FIG. 10*g*2 later in this Specification). Note that FIGS. 9*g*1 and 9*j* show optional third elements present as dashed-lines. Addition of elements allows achieving a Compensator that provides better Psuedo-Achromatic characteristics than does a single or dual element Compensator.

It is specifically to be understood that a compensator means system can be comprised of at least one Zero-Order waveplate and at least one effectively Zero-Order waveplate in combination, as well as combinations comprised of two actual Zero-Order waveplates or two effectively Zero-Order waveplates. And, a compensator can comprise more than two Zero-Order waveplate and/or effectively Zero-Order waveplates. FIGS. 9*g*1 and 9*j*, for instance, demonstrate in dashed lines the presence of additional Zero-Order waveplate and/or effectively Zero-Order waveplates. It is specifically noted that the dashed lines in FIG. 9*g*1 can represent a true single plate Zero-Order waveplate and the dashed lines in FIG. 9*j* an effectively Zero-Order waveplate. For instance, in FIG. 9*j*, the dashed lines can be an effective Zero-Order waveplate constructed from plates similar to (MOA1) and (MOB1). Also, the dashed lines in FIG. 9*g*1 can be interpreted represent a single Zero-Order waveplate similar to (MOA) in FIG. 9*j*, by assuming deletion of one dashed line. The Claims are to be understood in light of this disclosure.

A disclosed invention embodiment as shown in FIG. 1*a*, 1*b*1 or 1*b*2 can comprise a compensator means (C) which is selected from the group consisting of:
comprised of at least two per se. zero-order waveplates (MOA) and (MOB), said per se. zero-order waveplates (MOA) and (MOB) having their respective fast axes rotated to a position offset from zero or ninety degrees with respect to one another, with a nominal value being forty-five degrees;
comprised of a combination of at least a first (ZO1) and a second (ZO2) effective zero-order wave plate, said first (ZO1) effective zero-order wave plate being comprised of two multiple order waveplates (MOA1) and (MOB1) which are combined with the fast axes thereof oriented at a nominal ninety degrees to one another, and said second (ZO2) effective zero-order wave plate being comprised of two multiple order waveplates (MOA2) and (MOB2) which are combined with the fast axes thereof oriented at a nominal ninety degrees to one another; the fast axes (FAA2) and (FAB2) of the multiple order waveplates (MOA2) and (MOB2) in said second effective zero-order wave plate (ZO2) being rotated to a position at a nominal forty-five degrees to the fast axes (FAA1) and (FAB1), respectively, of the multiple order waveplates (MOA1) and (MOB1) in said first effective zero-order waveplate (ZO1);

comprised of a combination of at least a first (ZO1) and a second (ZO2) effective zero-order wave plate, said first (ZO1) effective zero-order wave plate being comprised of two multiple order waveplates (MOA1) and (MOB1) which are combined with the fast axes thereof oriented at a nominal ninety degrees to one another, and said second (ZO2) effective zero-order wave plate being comprised of two multiple order waveplates (MOA2) and (MOB2) which are combined with the fast axes thereof oriented at a nominal ninety degrees to one another; the fast axes (FAA2) and (FAB2) of the multiple order waveplates (MOA2) and (MOB2) in said second effective zero-order wave plate (ZO2) being rotated to a position away from zero or ninety degrees with respect to the fast axes (FAA1) and (FAB1), respectively, of the multiple order waveplates (MOA1) and (MOB1) in said first effective zero-order waveplate (ZO1);

comprised of at least one zero-order waveplate, ((MOA) or (MOB)), and at least one effective zero-order waveplate, ((ZO2) or (ZO1) respectively), said effective zero-order wave plate, ((ZO2) or (ZO1)), being comprised of two multiple order waveplates which are combined with the fast axes thereof oriented at a nominal ninety degrees to one another, the fast axes of the multiple order waveplates in said effective zero-order wave plate, ((ZO2) or (ZO1)), being rotated to a position away from zero or ninety degrees with respect to the fast axis of the zero-order waveplate, ((MOA) or (MOB));

Further, essentially any Compensator which can be placed into a beam of electromagnetic radiation can be applied, such as those disclosed in claim 9 of U.S. Pat. No. 5,872,630, (which 630 Patent is incorporated by reference hereinto):

Berek-type;
Non-Berek-type;
Zero Order;
Zero Order comprising a plurality of plates;
Rhomb;
Polymer;
Achromatic Crystal; and
Psuedo-Achromatic.

(It is specifically to be understood that a present invention compensator system can be comprised of at least one Zero-Order waveplate and at least one effectively Zero-Order waveplate in combination, as well as combinations comprised of two actual Zero-Order waveplates or two effectively Zero-Order waveplates).

FIGS. 9k1-9q demonstrate additional compensators which can be applied in the present invention.

FIG. 9k1 shows that one such other present invention retarder system (3) comprises a first triangular shaped element (P1), which as viewed in side elevation presents with first (OS1) and second (OS2) sides which project to the left and right and downward from an upper point (UP1). Said first triangular shaped element (P1) first (OS1) and second (OS2) sides have reflective outer surfaces. Said retarder system (3) further comprises a second triangular shaped element (P2) which as viewed in side elevation presents with first (IS1) and second (IS2) sides which project to the left and right and downward from an upper point (UP2), said second triangular shaped element (P2) being made of material which provides internally reflective, phase delay introducing, interfaces on first (IS1) and second (IS2) sides inside thereof. Said second triangular shaped element (P2) is oriented with respect to the first triangular shaped element (P1) such that the upper point (UP2) of said second triangular shaped element (P2) is oriented essentially vertically directly above the upper point (UP1) of said first triangular shaped element (P1). In use an input electromagnetic beam of radiation (LB) caused to approach said first (OS1) side of said first triangular shaped element (P1) along an essentially horizontally oriented locus, is shown as being caused to externally reflect from an outer surface thereof and travel along as electromagnetic beam of radiation (R1) which is essentially upwardly vertically oriented. Next said electromagnetic beam of radiation (R1) is caused to enter said second triangular shaped element (P2) and essentially totally internally reflect from said first (IS1) side thereof, then proceed along an essentially horizontal locus and essentially totally internally reflect from the second (IS2) side thereof and proceed along an essentially downward vertically oriented electromagnetic beam of radiation (R3). This is followed by an external reflection from an outer surface of said second side (OS2) of said first triangular shaped element (P1) such that said electromagnetic beam (LB') of radiation proceeds along an essentially horizontally oriented locus, undeviated and undisplaced from the essentially horizontally oriented locus of said input beam (LB) of essentially horizontally oriented electromagnetic radiation. This is the case even when said retarder system (3) is caused to rotate. The result of said described retarder system (3) application being that retardation is entered between orthogonal components of said input electromagnetic beam of radiation (LB). Further, said first (P1) and second (P2) triangular shaped elements are typically right triangles in side elevation as shown in FIG. 9k1, and the outer surfaces of first (OS1) and second (OS2) sides are typically, but not necessarily, made reflective by the presence of a coating of metal thereupon. A coating of metal serves assure a high reflectance and good electromagnetic beam radiation intensity throughput. Also, assuming accurately manufactured right angle first (P1) and second (P2) triangular shaped elements are utilized, this compensator design provides inherent compensation of both angular and translational misalignments of the input light beam (LB). As well, the total retardence provided is compensated for angular misalignments of the input electromagnetic radiation beam. That is, if the input electromagnetic radiation beam (LB) is not aligned so as to form an angle of incidence of forty-five (45) degrees with the first outer surface (OS1), the reflected electromagnetic beam (R1) will internally reflect at the first internal surface (IS1) of the second triangular shaped element (P2) at a larger (smaller) angle than would be the case if said angle of incidence were forty-five (45) degrees. This effect, however, is directly compensated by a smaller (larger) angle of incidence of electromagnetic beam (R2) where it internally reflects from inner surface (IS2) of the second triangular shaped element (P2). As another comment it is to be understood that because of the oblique angles of incidence of the reflections from the outer surfaces (OS1) and (OS2) of the first triangular shaped element (P1) a polarimeter/ellipsometer in which said compensator (3) is present will require calibration to characterize the PSI-like component thereof.

FIG. 9k2 shows a variation (3') on FIG. 9k1, wherein the first triangular shaped element is replaced by two rotatable reflecting means, identified as (OS1') and (OS2'). This modification allows user adjustment so that the locus of an entering electromagnetic beam (LB') exits undeviated and undisplaced from an entering electromagnetic beam (LB).

FIG. 9*l* shows that another additional present invention retarder system (4) comprises a parallelogram shaped element which, as viewed in side elevation, has top (TS) and bottom sides (BS), each of length (d) parallel to one another, both said top (TS) and bottom (NS) sides being oriented essentially horizontally. Said retarder system (4) also has right (RS) and left (LS) sides parallel to one another, both said right (RS) and left (LS) sides being of length (d/cos(∝)), where alpha (∝) is shown as an angle at which said right (RS) and left (LS) sides project from horizontal. Said retarder system (4) is made of a material with an index of refraction greater than that of a surrounding ambient. In use an input beam of electromagnetic radiation (LB) caused to enter the left side (LS) of said retarder system (4), along an essentially horizontally oriented locus, is caused to diffracted inside said retarder system (4) and follow a locus which causes it to essentially totally internally reflect from internal interfaces of both said top (TS) and bottom (BS) sides, and emerge from said retarder system (4) as (LB') from the right side (RS) thereof, along an essentially horizontally oriented locus which is undeviated and undisplaced from the essentially horizontally oriented locus of said input beam (LB) of essentially horizontally oriented electromagnetic radiation. This is the case even when said retarder system (4) is caused to rotate. The result of said described retarder system (4) application being that retardation is entered between orthogonal components of said input electromagnetic beam of radiation at said internal reflections from the top (TS) and bottom (BS) surfaces. This retarder system is very robust as it is made of single piece construction. It is noted that adjustment of the angle alpha (∝) in manufacture allows setting the amount of retardation which is provided by the retarder system (4). In addition, coatings can be externally applied to top (TS) and bottom surface (BS) to adjust retardation effected by internal reflection from said top (TS) and bottom (BS) surfaces. A formula which defines the retardation provided thereby being:

$$\frac{d}{h} = 2 - \tan(\phi), \text{ where } \phi = \alpha + \sin^{-1}\left(\frac{\sin(90-\alpha)}{n}\right)$$

Figure 9M:
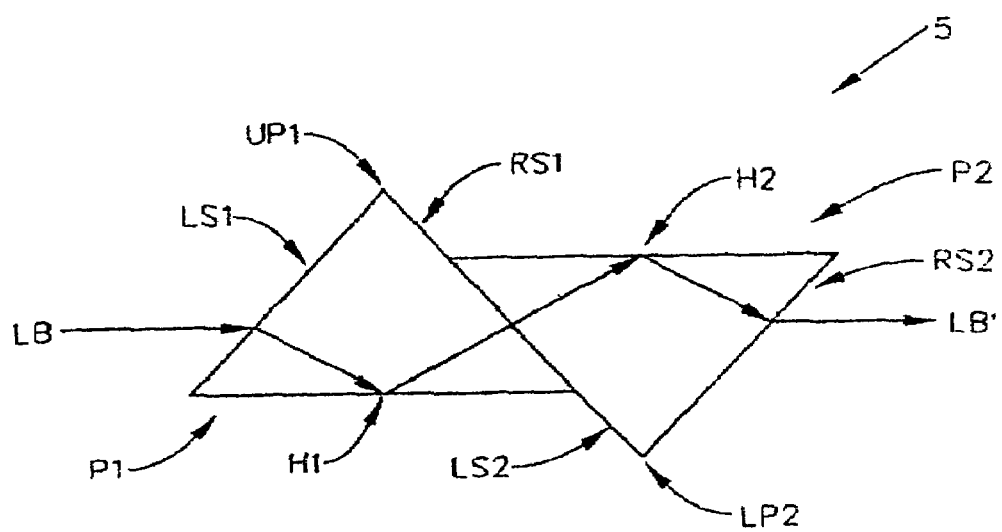

FIG. 9*m* shows that another additional present invention retarder system (5) comprises first (P1) and second (P2) triangular shaped elements. Said first (P1) triangular shaped element, as viewed in side elevation, presents with first (LS1) and second (RS1) sides which project to the left and right and downward from an upper point (UP1), said first triangular shaped element (P1) further comprising a third side (H1) which is oriented essentially horizontally and which is continuous with, and present below said first (LS1) and second (RS1) sides. Said second triangular shaped element (P2), as viewed in side elevation, presents with first (LS2) and second (RS2) sides which project to the left and right and upward from a lower point (LP2), said second triangular shaped element (P2) further comprising a third side (H2) which is oriented essentially horizontally and which is continuous with, and present above said first (LS2) and second (RS2) sides. Said first (P1) and second (P2) triangular shaped elements being positioned so that a rightmost side (RS1) of said first (P1) triangular shaped element is in contact with a leftmost side (LS2) of said second (P2) triangular shaped element over at least a portion of the lengths thereof. Said first (P1) and second (P2) triangular shaped elements are each made of material with an index of refraction greater than that of a surrounding ambient. In use an input beam (LB) of electromagnetic radiation caused to enter the left (LS1) side of said first (P1) triangular shaped element and is caused to diffracted inside said retarder system (5) and follow a locus which causes it to essentially totally internally reflect from internal interfaces of said third sides (H1) and (H2) of said first (P1) and second (P2) triangular shaped elements, respectively, and emerge from said right side (RS2) of said second (P2) triangular shaped element as electromagnetic radiation beam (LB') which is oriented along an essentially horizontal locus which is undeviated and undisplaced from the essentially horizontally oriented locus of said input beam (LB) of essentially horizontally oriented electromagnetic radiation. This is the case even when said retarder system (5) is caused to rotate. The result of said described retarder system (5) application being that retardation is entered between orthogonal components of said input electromagnetic beam of radiation (LB). It is noted that as long as the third sides (H1) and (H2) of said first (P1) and second (P2) triangular shaped elements are parallel, the output electromagnetic beam (LB') is undeviated and undisplaced from the input electromagnetic beam (LB) in use. It is noted that The triangular shape elements (P1) and/or (P2) can be made of various materials with various indicies of refraction, and coating(s) can be applied to one or both of the third sides (H1) and (H2) of said first (P1) and second (P2) triangular shaped elements to adjust retardation entered to an electromagnetic beam (LB1).

Figure 9N:
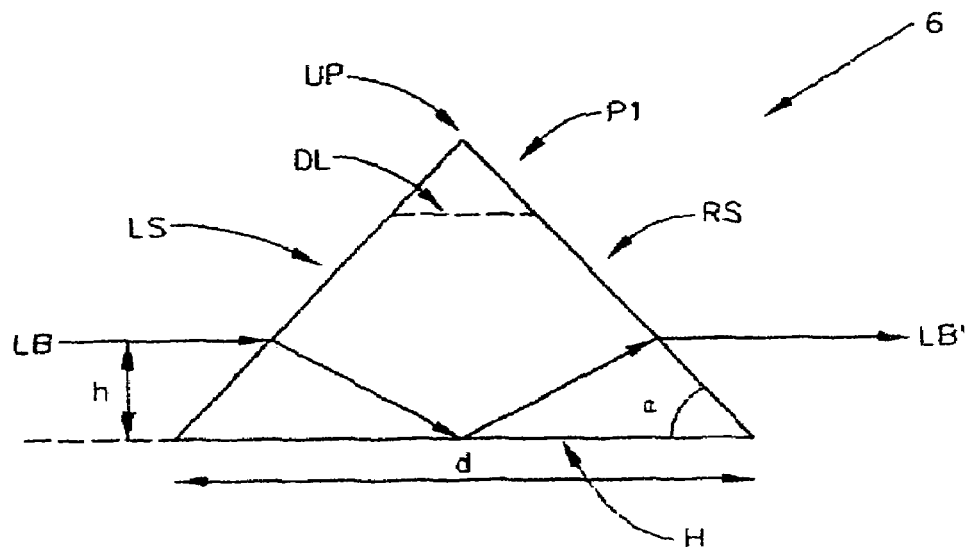

FIG. 9*n* shows that another additional present invention retarder system (6) comprises a triangular shaped element, which as viewed in side elevation presents with first (LS) and second (RS) sides which project to the left and right and downward from an upper point (UP). Said retarder system (6) further comprises a third side (H) which is oriented essentially horizontally and which is continuous with, and present below said first (LS) and second (RS) sides. Said retarder system (6) is made of a material with an index of refraction greater than that of a surrounding ambient. In use an input beam of electromagnetic radiation (LB) caused to enter the first (LS) side of said retarder system (6) along an essentially horizontally oriented locus, is caused to diffracted inside said retarder system (6) and follow a locus which causes it to essentially totally internally reflect from internal interface of said third (H) side, and emerge from said retarder system (6) from the second (RS) side along an essentially horizontally oriented locus which is undeviated and undisplaced from the essentially horizontally oriented locus of said input beam of essentially horizontally oriented electromagnetic radiation (LB). This is the case even when said retarder system (6) is caused to rotate. The result of said described retarder system (6) application being that retardation is entered between orthogonal components of said input electromagnetic beam of radiation (LB). The FIG. 9*n* retarder system (6) is typically an isosceles prism which is available off-the-shelf with an angle alpha (∝) of forty-five (45) degrees. As long as the input electromagnetic beam (LB) height (h) is chosen in accordance with the formula:

$$d = 2h\left(\frac{1}{\tan(\alpha)} + \tan(\phi)\right), \text{ where } \phi = \alpha - \sin^{-1}\left(\frac{\sin(90-\alpha)}{n}\right)$$

in conjunction with the index of refraction (n) of the material from which the retarder system (6) is made, and the locus of the input electromagnetic radiation beam (LB) is parallel with the third side (H) of said retarder system (6), the output electromagnetic beam (LB') will not be deviated or translated with respect to the input electromagnetic beam (LB). As well, note the dashed line (DL) below the upper point (UP). This indicates that as the region above said dashed line (DL) is not utilized, the portion of said retarder system (6) thereabove can be removed. It is also noted that the input electromagnetic beam (LB) enters and exits the retarder system (6) other than along a normal to a surface thereof, said retarder system is not an ideal retarder with a PSI of forty-five (45) degrees. It is noted that the third side (H) of the retarder system (6) can be coated to change the retardation effects of an internal reflection of an electromagnetic beam of radiation therefrom, and such a coating can have an adverse effect on the nonideal PSI characteristics.

FIG. 9q shows that another additional present invention retarder system (7) comprises first (PA1) and second (PA2) parallelogram shaped elements which, as viewed in side elevation, each have top (TS1)/(TS2) and bottom (BS1)/(BS2) sides parallel to one another, both said top (TS1) (TS2) and bottom (BS1) (BS2) sides each being oriented at an angle to horizontal. Said first (PA1) and second (PA2) parallelogram shaped elements also each have right (RS1)/(RS2) and left (LS1)/(LS2) sides parallel to one another, all said right (RS1) (RS2) and left (LS1) (LS2) sides being oriented essentially vertically. Said first (PA1) and second (PA2) parallelogram shaped elements are made of material with an index of refraction greater than that of a surrounding ambient. A right most vertically oriented side (RS1) of said first parallelogram is in contact with a leftmost (LS2) vertically oriented side of the second parallelogram shaped element (PA2). In use an input beam of electromagnetic radiation (LB) caused to enter an essentially vertically oriented left side (LS1) of said first parallelogram shaped element (PA1) along an essentially horizontally oriented locus, is caused to be diffracted inside said retarder system and follow a locus which causes it to essentially totally internally reflect from internal interfaces of both said top (TS1) (TS2) and bottom (BS1) (BS2) sides of both said first and second parallelogram shaped elements (PA1) (PA2), then emerge from a right side (RS2) of said second parallelogram shaped element (PA2) along an essentially horizontally oriented locus as output beam of electromagnetic radiation (LB') which is undeviated and undisplaced from the essentially horizontally oriented locus of said input beam of essentially horizontally oriented electromagnetic radiation (LB). This is the case even when said retarder system (7) is caused to rotate. The result of said described retarder system (7) application being that retardation is entered between orthogonal components of said input electromagnetic beam of radiation (LB).

FIG. 9o1 shows that another additional present invention retarder system (8) comprises first (BK1) and second (BK2) Berek-type retarders which each have an optical axes essentially perpendicular to a surface thereof. As shown by FIG. 9o2, each of said first (BK1) and second (BK2) Berek-type retarders can have fast axis which are oriented other than parallel to one another, but for the presently described retarder system it is assumed that the fast axes are aligned, (ie. an angle PHI ( ) of zero (0.0) degrees exists between fast axes of the two Berek-type (BK1) and (BK2) plates in FIG. 9o1. Said first and second Berek-type retarders each present with first and second essentially parallel sides. Said first (BK1) and second (BK2) Berek-type retarders are oriented, as viewed in side elevation, with first (LS1) and second (RS1) sides of one Berek-type retarder (BK1) being oriented other than parallel to first (LS2) and second (RS2) sides of the other Berek-type retarder (BK2). In use an incident beam of electromagnetic radiation (LB) is caused to impinge upon one of said first (BK1) Berek-type retarder on one side (LS1) thereof, partially transmit therethrough then impinge upon the second Berek-type retarder (BK2), on one side thereof (LS2), and partially transmit therethrough such that a polarized beam of electromagnetic radiation (LB') passing through both of said first (BK1) and second (BK2) Berek-type retarders emerges from the second thereof in a polarized state with a phase angle between orthogonal components therein which is different than that in the incident beam of electromagnetic radiation (LB), and in a direction which is an essentially undeviated and undisplaced from the incident beam of electromagnetic radiation. This is the case even when said retarder system (8) is caused to rotate. The result of said described retarder system (8) application being that retardation is entered between orthogonal components of said input electromagnetic beam of radiation. For insight it is mentioned that, in general, a Berek-type retarder is a uniaxial anisotropic plate with its optical axis essentially perpendicular to a surface thereof. The retardence introduced to an electromagnetic beam caused to transmit therethrough is determined by a tipping of said plate. The retardation system (8) having two such Berek-type retarders present, is, it is noted, insensitive to small angular deviations in an input electromagnetic beam as each plate contributes approximately half of achieved retardence. This insensitivity results because if the input electromagnetic beam is slightly changed, one of said plates will contribute slightly more (less), but the second slightly less (more) retardence because of offsetting effective plate "tilts" with respect to electromagnetic beams input thereto. Also, said retarder system (8) is very nearly ideal in that the PSI component of the retarder system (8) is very near a constant forty-five (45) degrees. One problem however, is that Berek-type retarder plates exhibit a (1/wavelength) retardence characteristic which, without more, makes use over a wide spectral range difficult.

A variation of the just described retarder system (8) applies to the seventh additional present invention retarder system (9) as well, with the difference being that a FIG. 9o2 offset angle PHI (φ) other than zero (0.0) is present between fast axes of the two Berek-type plates. The description of the system remains otherwise unchanged. The benefit derived, however, is that a flatter than (1/wavelength) retardation characteristic can be achieved thereby.

FIG. 9p1 serves as the pictorial reference for another additional present invention retarder system (10) which comprises first (BK1), second (BK2), third (BK3) and forth (BK4) Berek-type retarders which each have an optical axes essentially perpendicular to a surface thereof, each of which first (BK1) and second (BK2) Berek-type retarders has a fast axis, said fast axes in said first (BK1) and second (BK2) Berek-type retarders being oriented essentially parallel to one another. This is exemplified by FIG. 9p2. Said first (BK1) Berek-type retarder presents with first (LS1) and second (RS1) essentially parallel sides and said second (BK2) Berek-type retarders each present with first (LS2) and second (RS2) essentially parallel sides, and said first (BK1) and second (BK2) Berek-type retarders are oriented, as viewed in side elevation, with first (LS1) and second (RS1) sides of said first Berek-type retarder being oriented other than parallel to first (LS2) and second (RS2) sides of said second (BK2) Berek-type retarder. In use an incident beam of electromagnetic radiation (LB) is caused to impinge upon said first (BK1) Berek-type retarder on said first side (LS1) thereof, partially transmit therethrough then impinge upon the second (BK2) Berek-type retarder, on said first (LS2) side thereof, and partially transmit therethrough such that a polarized beam of electromagnetic radiation (LB') passing through both of said first (BK1) and second (BK2) Berek-type retarders emerges from the second thereof in a polarized state with a phase angle between orthogonal components therein which is different than that in the incident beam of electromagnetic radiation (LB), and in a direction which is an essentially undeviated and undisplaced from the incident beam of electromagnetic radiation (LB). Each of which third (BK3) and forth (BK4) Berek-type retarders also has a fast axis, and said fast axes in said third (BK3) and forth (BK4) Berek-type retarders are oriented essentially parallel to one another but other than parallel to the parallel fast axes of said first (BK1) and second (BK2) Berek-type retarders. Said third (BK3) Berek-type retarder presents with first (LS3) and second (RS3) essentially parallel sides, and said forth (BK4) Berek-type presents with first (LS4) and second (RS4) essentially parallel sides, and said first third (BK3) and forth (BK4) Berek-type retarders are oriented, as viewed in side elevation, with first (LS3) and second (RS3) sides of one of said third (BK3) Berek-type retarder being oriented other than parallel to first (LS4) and second (RS4) sides of said forth (BK4) Berek-type retarder; such that in use an incident beam of electromagnetic radiation (LB') exiting said second (BK2) Berek-type retarder is caused to impinge upon said third (BK3) Berek-type retarder on said first (LS3) side thereof, partially transmit therethrough then impinge upon said forth (BK4) Berek-type retarder on said first (LS4) side thereof, and partially transmit therethrough such that a polarized beam of electromagnetic radiation (LB") passing through said first (BK1), second (BK2), third (BK3) and forth (BK4) Berek-type retarders emerges from the forth (BK4) thereof in a polarized state with a phase angle between orthogonal components therein which is different than that in the incident beam of electromagnetic radiation (LB) caused to impinge upon the first (LS1) side of said first (BK1) Berek-type retarder, in a direction which is an essentially undeviated and undisplaced from said incident beam of electromagnetic radiation (LB). This is the case even when said retarder system (8) is caused to rotate. The result of said described retarder system (8) application being that retardation is entered between orthogonal components of said input electromagnetic beam of radiation.

Another additional present invention retarder system (11) is also pictorially represented by FIG. 9p1 and is similar to that just described excepting that the Berek-type retarder plates (BK1) and (BK2) fast axes need not be parallel to one another and the Berek-type retarder plates (BK3) and (BK4) need not be parallel to one another. However, if as a group Berek-type retarder plates ((BK1) and (BK2))/((BK3) and (BK4)) are parallel, they can be, but need not be parallel the fast axes of Berek-type retarder plates ((BK3) and (BK4))/((BK1) and (BK2)). This embodiment includes the case where all the fast axes of all Berek-type retarders (BK1), (BK2), (BK3) and (BK4) are all different.

Now, and very importantly, even though the Invention disclosed in this Specification is a Rotating Compensator Material System Investigation System which is Spectroscopic, (ie. simultaneously operates on a number of Wavelengths in a Beam containing many Electromagnetic Wavelengths, over a range of, for instance, 130-1700 nanometers), a Compensator Means (C), (C'), (C") utilized therein can provide a Retardance which varies with Wavelength and still be usable. A Compensator Means (C), (C'), (C") does however, typically, have to be of a nature to allow passage of a Polychromatic Electromagnetic Beam therethrough without causing significant Attenuation, Deviation or Displacement in the Direction of Propagation thereof. Particularly as regards Deviation and Displacement, if this is not the case, difficult to compensate complexities are caused in Detector Elements (DE's) containing Photo Array Detector System (DET) Detector Element Output Signals.

The reason a Spectroscopic Ellipsometer can operate with a Means (C), (C'), (C") that does not provide a Constant Ninety (90) Degree Retardance over a range of Wavelengths, (which would constitute Ideal Characteristics), is that a Regression based Calibration Procedure utilized, (see the Disclosure of the Invention Section of this Specification), provides Wavelength dependent Compensation effecting values for Calibration Parameters as required in a developed Mathematical Model of the Rotating Compensator Material System Investigation System, (ie./eg. Rotating Compensator Spectroscopic Ellipsometer). As better described in the Disclosure of the Invention Section of this Disclosure, the Inventors develop a Calibration Parameter Containing Mathematical Model of the Rotating Compensator Material System Investigation System by, for instance, utilizing Matrix Representations for various System Components involved, then multiplies out the Matrices in an appropriate order to provide a Transfer Function. This applies for all Wavelengths monitored by a Detector Elements (DE's) containing Photo Array Detector System (DET) Detector Element (DE). Next, Data Set(s) are Experimentally obtained as a function of wavelength and typically as a function of various settings of the Polarizer Means (P) or Analyzer Means (A), (or both could be rotated to various positions), while a Compensator Means (C) rotates at, typically though not necessarily, Twenty (20) to Thirty (30) Hz. Other rotation speeds can be utilized and if two Compensator Means (C) (C') are present one or both can be caused to rotate, and if both are caused to rotate, as mentioned infra herein, they can be caused to rotate at the same, or different, speeds. (Note that Data Set(s) could also be achieved utilizing variation of Angle-Of-Incidence of a Beam of Polychromatic Radiation with respect to a Material System under investigation). Calibration Parameters in the Mathematical Model are then evaluated by, typically, Mean-Square-Error based Regression onto the Data Set(s). It is also possible to effectively find Calibration Parameter containing Mathematical Expressions for Coefficients of Mathematical Series, (eg. Fourier Series), which comprise the Mathematical Model Transfer Function, and calculate Numerical Values for the Coefficients from the Data Set(s), then effectively perform Regression of said Calibration Parameter containing Mathematical Expressions for Coefficients of Mathematical Series Transfer Function onto said Numerical Values for the Coefficients from the Data Set(s). It is emphasized that a single Two-Dimensional Data Set has been found sufficient to allow excellent Calibration results to be achieved. Said Two-Dimensional Data Set typically is Intensity vs. Wavelength, and Polarizer Means or Analyzer Means Azimuthal Rotation Angle settings. In addition, said Two-Dimensional Data Set can be obtained from a Rotating Compensator Material System Investigation System oriented so that a Polychromatic Beam of Electromagnetic Radiation interacts with a Material System, (ie. the "Sample Present" Mode—see FIGS. 1a, 1b1, 1b2, 3, 4, and 5)), or such that said Polychromatic Beam of Electromagnetic Radiation passes through the Rotating Compensator Material System Investigation System without interacting with a Material System, other than a Material System, comprised of "Open Atmosphere", (ie. the "Straight-Through" Mode—see FIG. 7).

The Rotating Compensator Material System Investigation System can also, of course, be Calibrated utilizing more than one Data Set and such a procedure is reported in U.S. Pat. No. 5,706,212, wherein a Rotating Compensator Material System Investigation System utilized in the Infra-red band of wavelengths, requires that two (2) Data Sets be present, (eg. selected with the Rotating Compensator Material System Investigation System oriented in a manner selected from the group: ("Straight-Through", "Material System Present", "Alternative Material System Present")). Both Data Sets are simultaneously utilized in a Regression Procedure to evaluate numerous Calibration Coefficients in a Mathematical Model which is described in the 212 Patent. The reason that only one (1) Data Set is can suffice to practice the described Calibration Procedure, is that the number of Calibration Parameters required by the Mathematical Model of the system, (which is not operated in the Infra-red range of wavelengths), is much fewer that the number of Calibration Parameters required by the Mathematical Model of the Rotating Compensator Material System Investigation System operated in the Infra-red range of wavelengths. The Rotating Compensator Material System Investigation System Mathematical Model typically involves as few as Five (5) Calibration Parameters, (where only one Compensator Means is present), in combination with simultaneous determination of a Material System PSI and DELTA. (It is noted that a straight-through mode essentially provides open atmosphere as a Material System and that the PSI and DELTA of open atmosphere are forty-five (45) degrees and zero (0.0) degrees, respectively). Said Five (5) Calibration Parameters are Azimuthal Orientation Angles for Polarizer Means (Ps), Analyzer Means (As), Compensator Means (Cs), and Compensator Retardance Parameters (P0) and (P1). (Note that the (Ps), (Cs) and (As) Azimuthal Orientation Calibration Angles can be thought of as serving to align the Polarizer Means, Compensator Means and Analyzer Means Azimuths with a Material System, (Sample), Frame of Reference). Of course, if two Compensator Means are present then an additional Compensator Orientation Angle (Cs2) and Compensator Retardance Parameters (P0') and (P1') would also have to be evaluated. (It is noted that Retardation entered between orthogonal components of a Polarized Electromagnetic Beam, by a Compensator Means, is accounted for by a Matrix Component, and typically the r4 term of a Jones Matrix, but such is accounted for by Compensator Retardation Parameters (P0), (P1), (P0'), (P1') in the presently described Calibration Procedure).

A more complex calibration procedure provides for obtaining two (2) or three (3) data sets, and simultaneously regressing thereonto. A more complex calibration procedure can be beneficial where, for instance, a large wavelength range is being utilized and/or where multiple Angles of Incidence are to be utilized, and/or where it is desired to determine component "De-Polarization" effects and/or evaluate Mueller Matrix components. Where a multiple data set calibration procedure is practiced, a first data set is typically obtained utilizing a silicon substrate sample with two-hundred (200) to three-hundred (300) Angstroms, (eg. a nominal two-hundred-fifty (250) Angstroms), of silicon-dioxide on the surface thereof. A second data set can be obtained utilizing a sample which provides a large Ellipsometric PSI value, and an Ellipsometric DELTA value of between thirty (30) and one-hundred-fifty (150) degrees. Internal reflections from the hypotenuse of a right angle prism, either uncoated or coated with aluminum, or an optically thick metallic film, will provide such characteristics. FIGS. 1a, 1b1, 1b2, 3, 4 and 5 demonstrate sample present data set gathering configurations of a Rotating Compensator Ellipsometer System. A third data set can be obtained with the ellipsometer system configured in a "straight-through" configuration, (see FIG. 7), wherein the effective sample PSI is forty-five (45) degrees and the effective sample DELTA is zero (0.0) degrees.

In general, the disclosed invention provides that at least one, at least one-dimensional, data set(s) be obtained utilizing a selection from the group consisting of:
  all of said at least one, at least one-dimensional data set(s), are obtained utilizing a single material system (MS) placed on said stage (STG) for supporting a material system (MS), with which material system, (sample) (MS) the beam of electromagnetic radiation (PPCLB) is caused to interact;
  at least one of said at least one, one-dimensional data set(s) is obtained utilizing one material system (sample) (MS) placed on said stage (STG) for supporting a material system, (sample) (MS), and at least one other of said at least one at least one-dimensional data set(s) is obtained utilizing another material system, (sample) (MS) placed on said stage (STG) for supporting a material system, (sample) (MS)), with which material system(s), (samples), (MS) the beam of electromagnetic radiation (PPCLB) is caused to interact; and
  at least one of said at least one-dimensional data set(s) is obtained with the spectroscopic rotating compensator material system investigation system oriented in a "straight-through" configuration wherein a polychromatic beam of electromagnetic radiation (PPCLB) produced by said source (LS) of a polychromatic beam of electromagnetic radiation, is caused to pass through said polarizer means (P), pass through said analyzer means (A), and interact with said dispersive optics (DO) such that a multiplicity of essentially single wavelengths are caused to simultaneously enter a corresponding multiplicity of detector elements (DE's) in said at least one detector system (DET), with said polychromatic beam of electromagnetic radiation (PPCLB) also being caused to pass through at least one compensator means (C) (C') (C'') but without being caused to interact with any material system, (sample), (MS) placed on said stage (STG) for supporting a material system, (sample), (MS).

(Note: Preferred practice is to obtain at least two, at least one dimensional data sets; or at least one multiple dimension data set upon which to regress).

Continuing, where a multiple data set calibration procedure is utilized to calibrate a rotating compensator material system investigating system for measuring Ellipsometric and Depolarization/Mueller Matrix values, it is also disclosed that it has been found desirable to normalize data to D.C. in some portions of the calibration, and to an A.C. derived term in other portions thereof.

A method of calibrating a Spectroscopic Ellipsometer System can comprise the steps of:
  a. providing a spectroscopic ellipsometer for evaluating a sample comprising:
    broadband electromagnetic radiation source means generating a beam having wavelengths extending over a range of at least 200 to 800 nm;
    polarizer means disposed in the path of said beam;
    compensator means disposed in the path of the beam, said compensator for inducing phase retardations in the polarization state of the light beam, said compensator means having characteristics other than substantially non-achromatic, said compensator means being rotated at an angular frequency of ω;
    analyzer means that interact with the beam after the beam interacts with the sample and the compensator means;
    detector means that measure the intensity of the beam after the interaction with the analyzer means at a plurality of wavelengths across the wavelength range of at least 200 to 800 nm;

said detector means generating a time varying intensity signal simultaneously comprising 2ω and 4ω component signals, said 2 and 4ω signals being simultaneously present at all wavelengths measured unless the 2ω signal is forced to 0.0 by a sample presenting with an ellipsometric DELTA of 0.0 as opposed to being caused to be 0.0 by said compensator means;

b. developing a mathematical model of said spectroscopic ellipsometer system which comprises as calibration parameter(s) at least one selection from the group consisting of:
effective polarizer means azimuthal angle orientation;
present sample PSI (ψ), as a function of angle of incidence and a thickness;
present sample DELTA (Δ), as a function of angle of incidence and a thickness;
retardations of said compensator means as a function of wavelength;
compensator means azimuthal angle orientation;
matrix components of said compensator means; and
analyzer means azimuthal angle orientation;

which mathematical model is effectively a transfer function which enables calculation of electromagnetic beam magnitude detected by a detector element, given magnitude provided by said broadband electromagnetic radiation source means generating a beam having wavelengths extending over a range of at least 200 to 800 nm;

c. causing a polychromatic beam of electromagnetic radiation produced by said broadband electromagnetic radiation source means, to pass through said polarizer means, interact with a sample caused to be in the path thereof, pass through said analyzer means, and enter detector elements in said detector means, with said polychromatic beam of electromagnetic radiation also being caused to pass through said compensator means;

d. obtaining data as described by a selection from the group consisting of:
at least one multi-dimensional data set(s); and
least two, at least one-dimensional data sets;

said data set(s) being magnitude values vs. parameter(s) selected from the group consisting of:
wavelength;
angle-of-incidence of said polychromatic beam of electromagnetic radiation with respect to a present material system;
effective or actual azimuthal angle orientation of one element selected from the group consisting of:
said polarizer; and
said analyzer;

obtained over time, while at least one of said at least one compensator is caused to continuously rotate; said at least at least one, multi-dimensional data set(s) being obtained utilizing a selection from the group consisting of:
all of said at least one multi-dimensional data set(s), being obtained utilizing a single sample;
at least one of said at least one multi-dimensional data sets being obtained utilizing one sample, with another of said at least one multi-dimensional data sets being obtained utilizing another sample; and
at least one of said at least one multi-dimensional data set(s) being obtained with the spectroscopic ellipsometer oriented in a "straight-through" configuration wherein a polychromatic beam of electromagnetic radiation produced by said broadband electromagnetic radiation source means, generating a beam having wavelengths extending over a range of at least 200 to 800 nm, is caused to pass through said polarizer means, pass through said analyzer means and enter detector elements in said at least one detector system, with said polychromatic beam of electromagnetic radiation also being caused to pass through said compensator means but without being caused to interact with any sample other than open ambient atmosphere;

e. normalizing data in each said at least one, multi-dimensional, data set(s) with respect to a selection from the group consisting of:
a data set D.C. component;
a data set A.C. component;
a parameter derived from a combinations of a data set D.C. component and a data set A.C. component;

f. performing a mathematical regression of said mathematical model onto said normalized at least one, multi-dimensional, data set(s), thereby evaluating calibration parameters in said mathematical model;

said regression based calibration procedure serving to evaluate parameters in said mathematical model for non-achromatic characteristics and/or non-idealities and/or positions of at least one selection from the group consisting of:
effective azimuthal angle of said polarizer means;
azimuthal angle of said compensator means, retardation of said compensator means;
matrix components of said compensator means;
depolarization/Mueller Matrix components; and
azimuthal angle of said analyzer means.

g. optionally repeating steps e. and f. utilizing a different selection in step e. in normalizing data.

Continuing, the 630 Patent Method of Calibrating a Spectroscopic Rotating Compensator Material System Investigation System describes, in the step of calculating values of Coefficients of a Transfer Function from said Data Set, the calculation of values of Coefficients of a Fourier Series. Additionally, said 630 Patent Method of Calibrating a Spectroscopic Rotating Compensator Material System Investigation system can further comprise the step of Parameterizing Calibration Parameters by representing variation as a function of Wavelength, (or perhaps Angle-of-Incidence of said Polychromatic Beam of Electromagnetic Radiation with respect to a Surface of an Investigated Material System, (Sample), or Other Variable), by a Calibration Parameter containing Mathematical Equation, Calibration Parameter(s) in said Calibration Parameter containing Mathematical Equation being evaluated during said Mathematical Regression. When this is done the Calibration Parameter containing Mathematical Equation provides a functional relationship, and, it is noted, can even be a constant value over a range of, for instance, Wavelengths and/or Polarizer Azimuthal Angle settings).

It is further noted that the at least Two Dimensional Data Set can be obtained with the Spectroscopic Rotating Compensator Material System Investigation System oriented in a "Straight-Through" or "Material-System-(Sample)-Present" configuration. In the first configuration open atmosphere essentially constitutes a material system, and a Polarized Electromagnetic Beam passes directly through the Polarizer, Compensator and Analyzer into the Detector System. In the second configuration a Material System is present which presents PSI and DELTA values other than those of the open atmosphere so that a Polychromatic Electromagnetic Beam passes through the Polarizer, possibly a Compensator, and then interacts with a Material System before passing through, possibly a Compensator, an Analyzer and into the Detector System. Compensator(s), it should be understood, can be present before and/or after the Material System.

Preferred calibration procedure practise provides that data be normalized to A.C. where determining compensator means retardation (R), polarizer means azimuth (P) and compensator means fast axis azimuth (C) are fit, and that data be normalized to D.C where optical element Depolarization/ Meuller Matrix values are fit.

Now, it is to be understood that the system of the Spectroscopic Rotating Compensator Material System Investigation System is basically found in a combination of components shown in FIGS. 1a, 1b1, 1b2, 1c and 2, the basic result of said combination, for a Reflection Mode System, being shown in FIG. 3. That is, FIG. 3 shows a Spectroscopic Reflection Mode version of the Rotating Compensator Material System Investigation System shown in FIG. 1a, with the FIG. 2 Detector Elements (DE's) containing Photo Array Detector System (DET) shown present directly after the Analyzer (A).

Figure 4:
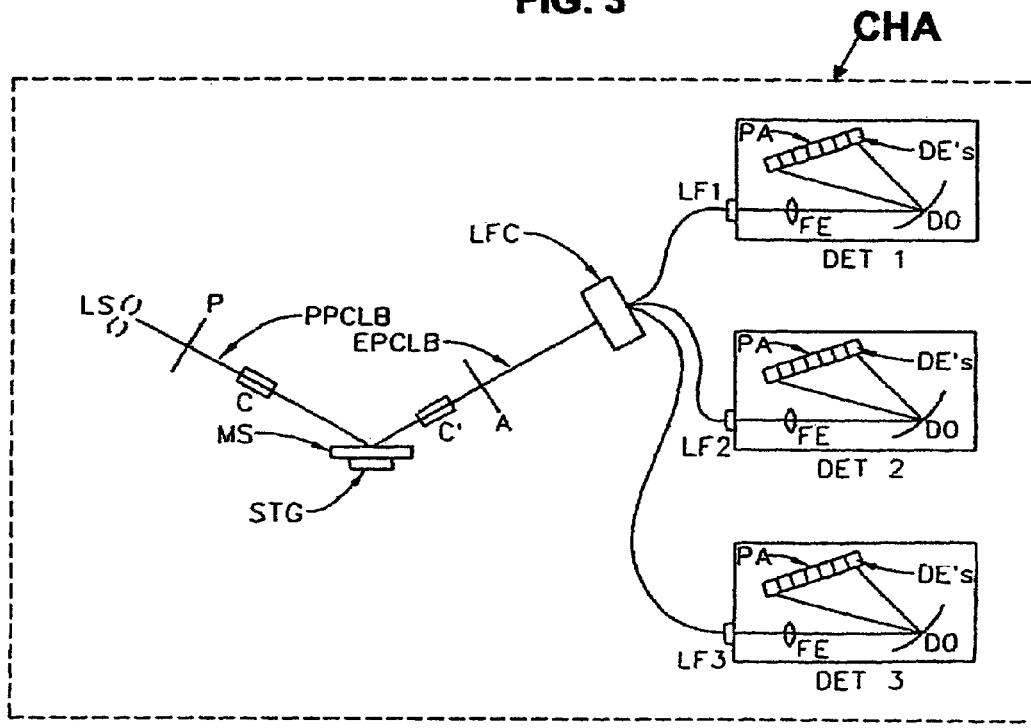
FIG. 4 shows a reflectance mode combination of components shown in FIGS. 1a and 2 in which three FIG. 2 spectrographic diode array spectrometer systems are present and provided input via light fibers.

FIG. 4 shows a Reflection Mode System configuration in which three (3) Detectors (Det 1), (Det 2) and (Det 3) are fed input by Fiber Optics (LF1), (LF2) and (LF3) present in a Fiber Optic Bundle exiting Fiber Optic Connector (LFC). Said Fiber Optic Connector (LFC) receives a Polarized Electromagnetic Beam (EPCLB) exiting the Analyzer (A). (Note that a FIG. 9c at least Bifrucated Fiber Optic could be utilized). Said three (3) Detectors (Det 1), (Det 2) and (Det 3) can be previously disclosed Off-the-shelf Zeiss Diode Array Spectrometers, and can each comprise a Focusing Element (FE) in functional combination with a Dispersive Optics (DO) and a Diode Element (DE) containing Photo Array (PA).

Figure 5A:
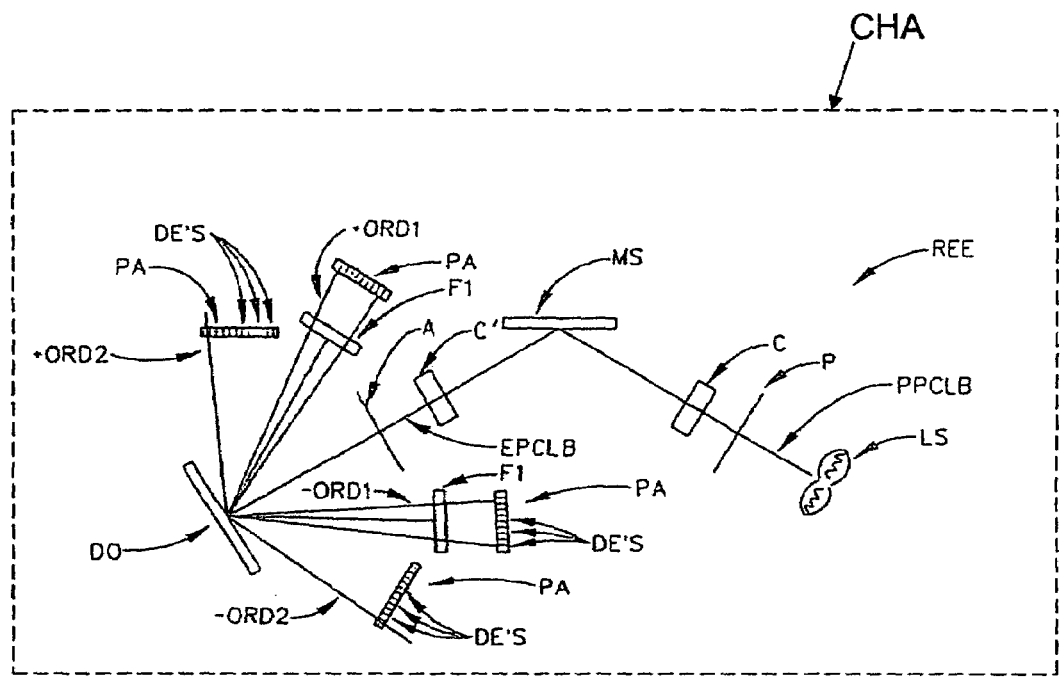
FIG. 5a shows a reflectance mode combination of components shown in FIGS. 1a and 2 in which multiple orders produced by a dispersive optics are intercepted by multiple photo arrays.

FIG. 5a shows that the described system can cause a Polychromatic Beam of Polarized Electromagnetic Radiation (PPCLB) to, after interaction with a Material System (MS), reflect therefrom. FIG. 5a shows that the Reflected Polarized Beam of Electromagnetic Radiation (EPCLB), is caused to impinge upon a Dispersive Optics (DO), (eg. a Diffraction Grating), such that a plurality of Orders (+ORD2, +ORD1, −ORD1 and −ORD2) are produced. Each said Order is comprised of a spectrum of Wavelengths, and FIG. 5a shows that Wavelengths in said Orders (+ORD2, +ORD1, −ORD1 and −ORD2) can be intercepted by Detector elements (DE's) in Photo Arrays (PA). Some embodiments of a Rotating Compensator Ellipsometer System utilize such a system. It is noted that the Dispersive Optics (DO) is typically rotatable so that the direction each Order of wavelengths generally proceeds from said Dispersive Optics (DO) is adjustable. Note that FIG. 5 also shows the presence of Filters (F1). It is noted that Wavelengths for adjacent Orders overlap, and said Filters (F1) allow a user to pass only desired Wavelengths, as well as reduce background radiation entry to Photo Arrays (PA's). Typically a Focusing Element is not present in a FIG. 5a embodiment.

It is also noted that Fiber Optics, such as demonstrated in FIGS. 9a-9c, can be utilized to carry Polychromatic Electromagnetic Radiation from a Source thereof (LS) to the position of a Polarizer Means (P), or from the position of an Analyzer Means (A) to a Detector (DET) in FIGS. 1a-5a.

Analogically similar figures to those shown in FIGS. 3-5a, but oriented for use in a Transmission Mode are not shown, but should be understood as within the scope of the implied by FIG. 1a.

Figure 6:
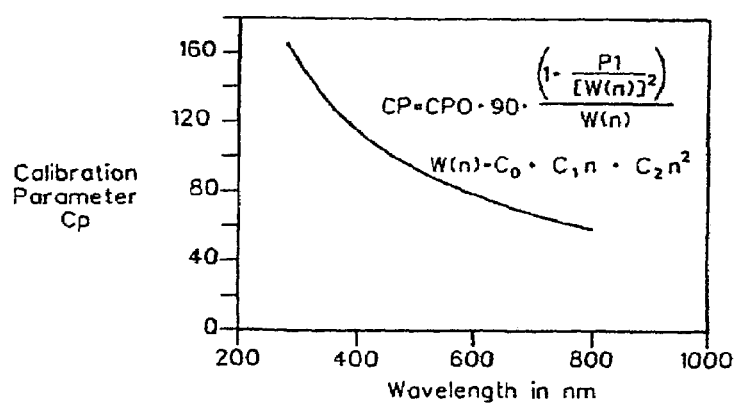
FIG. 6 demonstrates the parameterization approach to modeling calibration parameters which the disclosed invention utilizes in certain cases.

FIG. 6 demonstrates a Parameterization" approach to modeling Calibration Parameters in a Mathematical Model which was of more importance in the methodology of U.S. Pat. No. 5,872,630. Said example is retained herein as it is easy to understand. In that light, it must be understood that Calibration Parameters are often a function of Wavelength. For instance, the Retardation provided by a Compensator often varies inversely with wavelength. Where this is the case typical Mathematical Regression based evaluation of Calibration Parameters requires that a value for a Calibration Parameter be determined at each wavelength monitored. However, FIG. 6 shows that a plot of a Calibration Parameter vs. Wavelength can yield a locus which can be accurately modeled by a Mathematical Equation which requires only a few constants be known to allow calculation of the Calibration Parameter at a given Wavelength. For instance, FIG. 6 shows that a value for a Wavelength W(n) can be calculated knowing a Channel Number (n), (ie. Diode Element in an Array, such as shown in FIGS. 2-5), from which a signal is obtained, and values for three constants C0, C1 and C2. Knowing values for Parameters CP0 and P1 as well allows calculating a Calibration Parameter Value (CP) given a Diode Element Array Channel Number number (n). It can occur that (n) is two-hundred (200) or more and if a non-Parameterized approach to calibration is utilized, two-hundred (200) or more values for Calibration Parameter CP would have to be determined and stored. However, utilizing the Calibration Parameter Parameterization approach, it can be seen that a Regression procedure must return values for only Two (2) variables, (CP0 and P1). Also, if a Calibration Procedure were selected to include Angle-Of-Incidence (AOI) as a Data Set variable, it is known that where a Calibration Procedure utilizes a "Material System Present" configuration for acquiring data, that the PSI and DELTA values for the Material System, (Sample), will vary with said (AOI), and Material System and/or Surface Layer thereupon Thickness. (Note, said PSI and DELTA are equivalent to Calibration Parameters in a Regression procedure which serves to evaluate Calibration Parameters based upon Data obtained with a Material System present approach). A similar Parameterization approach could be applied to provide equations for calculating a PSI and a DELTA value given an (AOI) and/or, Material System or Surface Layer thereupon Thickness, each of said equations involving only a few variables which would have to be evaluated by a Regression procedure. (Note, the concept of "Parameterization" is often encountered in the modeling of Dielectric Functions, wherein one or more Lorentz Oscillator(s) is/are utilized. Lorentz Oscillator Structures require only a Magnitude, Energy and a Broadening Calibration Parameter be evaluated to be fully defined. Some peak regions of a Dielectric Function can be adequately modeled by said three evaluated Calibration Parameters, however, the peak and tail regions of a Lorentz Oscillator Structure are not mathematically separate and while a Lorentz Oscillator Structure might adequately define a peak region in a Dielectric Function plot, it is often inadequate in non-peak regions. This problem is the focus in U.S. Pat. No. 5,796,983 which teaches Finite Width Oscillator Structures comprised of Finite Order Polynomials and/or Finite Magnitude Essentially Zero Width Discontinuities as replacement for Lorentz Oscillator Structures). Where beneficial, Parameterization of Calibration Parameters can be utilized. That is, where a plot of a Calibration Parameter vs. a Data Set of Independent Variable demonstrates that Parameterization can be applied with benefit, the Parameterization of Calibration Parameter approach, with respect to some Data Set Independent Variable, can be applied.

Continuing, the described invention achieves a Spectroscopic Rotating Compensator Material System Investigation System (eg. Spectroscopic Rotating Compensator Ellipsometer System), preferably utilizing an "Off-The-Shelf" compact Spectrometer Systems, and utilizing "Off-The-Shelf" Compensator Means Components which are not at all "ideal", as regards Achromaticity. To put this into perspective, it is noted that prior to about 1997, there was no known Spectroscopic Rotating Compensator Ellipsometer available in the market-place. It is believed that this is because it has previously been believed that to achieve such a System an Achromatic Rotating Compensator (RC) would be required. Such Compensators are not generally commercially available, hence, are expensive and reasonable approximations thereof typically must be individually fabricated. (Note, as described in U.S. Pat. No. 5,706,212, a Dual-Rhomb Rotating Compensator (RC) which provides about seven (7%) percent variation in Retardation effected over a range of Wavelengths of approximately 2 to 14 microns, has been developed at the University of Nebraska. However, it is not clear that the identified University of Nebraska Dual-Rhomb Rotating Compensator (RC) would operate "Substantially Achromatically" outside the identified range of wavelengths, but would rather, as is generally the case with all physically realizable Compensators, it would operate Psuedo-Achromatically over a larger wavelength range).

For general information, FIGS. 8a through 8d show various Dispersive Optics geometries. FIG. 8a shows a lined geometry diffraction grating (DGDO). The grating lines (GL) are essentially rectangular in cross-section with a spacing (a) therebetween. FIG. 8b shows a "Blazed" geometry Diffraction Grating Dispersive Optics (BDGDO). The Blazing Angle (BA) shifts reflected diffracted energy between "Orders" such into +ORD1 and −ORD1 from a typically useless ORD0 which projects perpendicularly back from the surface of said Dispersive Optics shown in FIG. 5a. FIG. 8c shows a cross-sectional view of a Holographic Diffraction Grating Dispersion Optics (HDGDO) as is present in the Off-the-Shelf (Zeiss Diode Array Spectrometer systems identified infra herein. Said Zeiss Systems utilize a Holographic configuration in a concave shaped system). FIG. 8d shows a Prism Dispersive Optics (P1), with a Polarized Polychromatic Electromagnetic Beam (PPCCLB) entering Side (S1), and exiting Side (S2) and Side (S3) as Diffracted Beams in two "Orders" (ORDQ1) and (ORDP1) respectively. Note that a coating (OC) causes partial internal reflection of beam (PPCCBA) into beam (PPCLBB) to produce two "Orders". Any functional Diffraction effecting element can be utilized as a Dispersive Optics (DO) in the described invention.

Figure 5B:
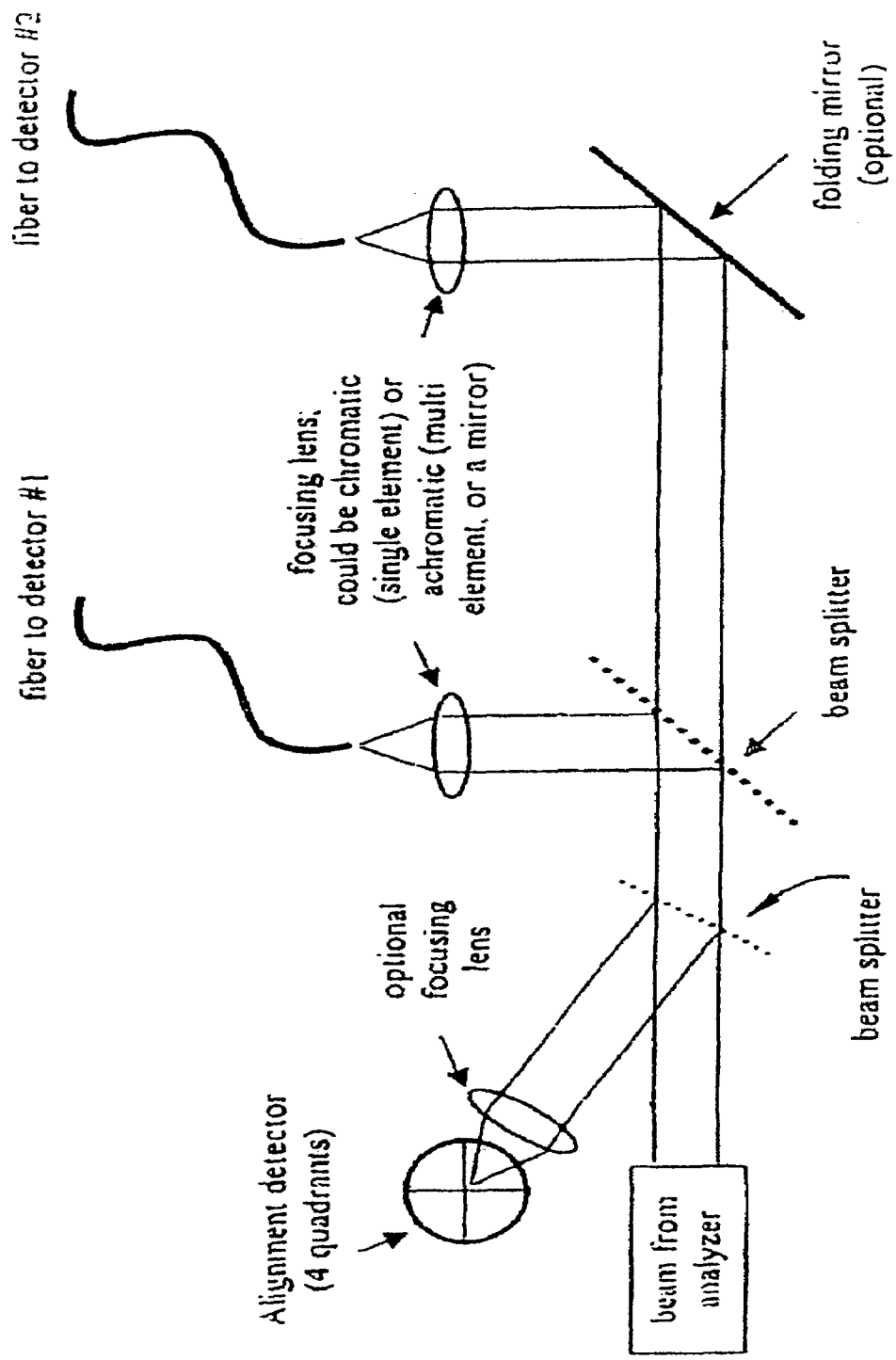
FIG. 5b shows a diagram demonstrating use of beam splitters to direct an incident electromagnetic beam into two detectors.
Figure 7:
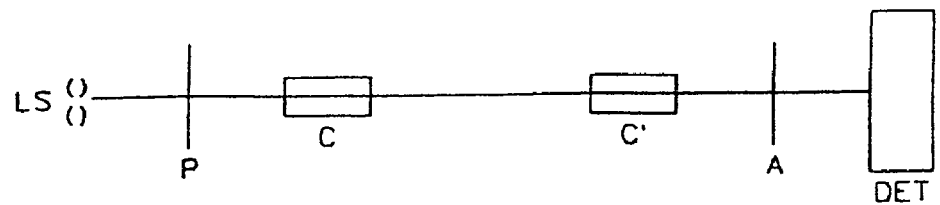
FIG. 7 demonstrates a "straight-through" configuration of a spectroscopic rotating compensator material system investigation system.

As the invention can utilize Fiber Optics, certain geometries thereof are shown in FIGS. 9a through 9c. FIG. 9a shows a Fiber Optic which is essentially circular at the left side and which becomes of a "slit" shape at the right side. FIG. 9b shows a Fiber Optic which is essentially circular shaped along the entire length thereof, and which provides input to a "Slit" per se., (as is functionally utilized in the embodiment shown in FIG. 2). The effects achieved by the Fiber Optics in FIGS. 9a and 9b are similar. FIG. 9c shows a Trifrucated Fiber Optic which is essentially circular at the left side, which trifrucates and then is exemplified as becoming circular or a of a "slit" shape at the right side. Use of an effectively Trifrucated Fiber Optics is shown applied in FIG. 4. (Noted that Optical Fibers are utilized only as convenient means by which to transport electromagnetic radiation and not to modify polarization state. Also, it has been found that a beam splitter can be used instead of the bifrucated fibers. FIG. 5b, for instance, shows a diagram demonstrating use of beam splitters to direct an incident electromagnetic beam into two detectors. The beam splitters can be a "polka-dot" type, (ie. Edmond Scientific part number 46-457 comprising a plate which is effectively half coated with a multiplicity of reflective regions), or stacked filters, or alternatively various bandgap materials, (eg. Si, Ge, GaN, ZnSe, ZnTe ZnCd etc.) can be substituted for the FIG. 5b system which reflect certain wavelengths and transmit others. FIG. 5b also shows use of a beam splitter to provide a 10% of incident electromagnetic beam as an alignment beam directed into a four quadrant detector, and demonstrates optional use of reflective means, (eg. a simple mirror or perhaps beam folding optics as described in U.S. Pat. No. 5,969,818 to Johs et al.). The presence of focusing lenses (optional), is also demonstrated, as are the presence of, where functional, fiber optic means to guide electromagnetism to indicated detectors #1 and #2.

Method of Calibration Disclosed in U.S. Pat. No. 5,872,630

Note, U.S. Pat. Nos. 5,872,630 and 6,353,477 present the mathematical equation basis for the regression based ellipsometer calibration discussed herein, and while incorporated by reference herein, presentation of the derivation thereof is lengthy and is not repeated in this Application which is focused on presenting preferred rotating compensator system embodiment aspects. The interested reader should consult the 630 and 477 Patents for additional detailed insight to the regression calibration procedure.

Continuing, in use the Spectroscopic Rotating Compensator Material System Investigation System is modeled mathematically, with Calibration Parameters being included in said Mathematical Model. Said Calibration Parameters are evaluated by a regression based approach based upon Data Set(s) obtained at a multiplicity of Angles-of-Incidence, and/or Wavelengths and/or Polarizer or Analyzer Rotation Angle Settings etc. (Note that a relatively easily obtained Two Dimensional Data Set as a function of Wavelength, and either Polarizer or Analyzer Azimuthal Angle Setting, is greatly preferred and has been found to be sufficient). As mentioned infra herein, typically, Matrix representations of the Polarizer Means (P), Compensator Means (C), Analyzer Means (A), are utilized, with calibration parameters appearing in Matrix Components. Once evaluation of the Spectroscopic Rotating Compensator Ellipsometer System (RC) Calibration Parameters is effected, a Material System (MS) can be subjected to investigation thereby, with otherwise unexplained changes effected in a Beam of Polarized Electromagnetic Radiation (LB), present after interaction with a Material System (MS), being attributed to said Material System (MS). (It is also to be noted that PSI and DELTA associated with a Material System at a specific Angle-Of-Incidence can be simultaneously evaluated with Calibration Parameter values if a Data Set is obtained utilizing a Material System present mode and the Mathematical Model includes said Material System PSI and DELTA as functions of, for instance, Material System Thickness and/or Material System Surface Layer Thickness, and Angle of Incidence of the Electromagnetic Beam with respect to the Material System Surface, as Fit Parameters).

Applications Results

Figure 10A:
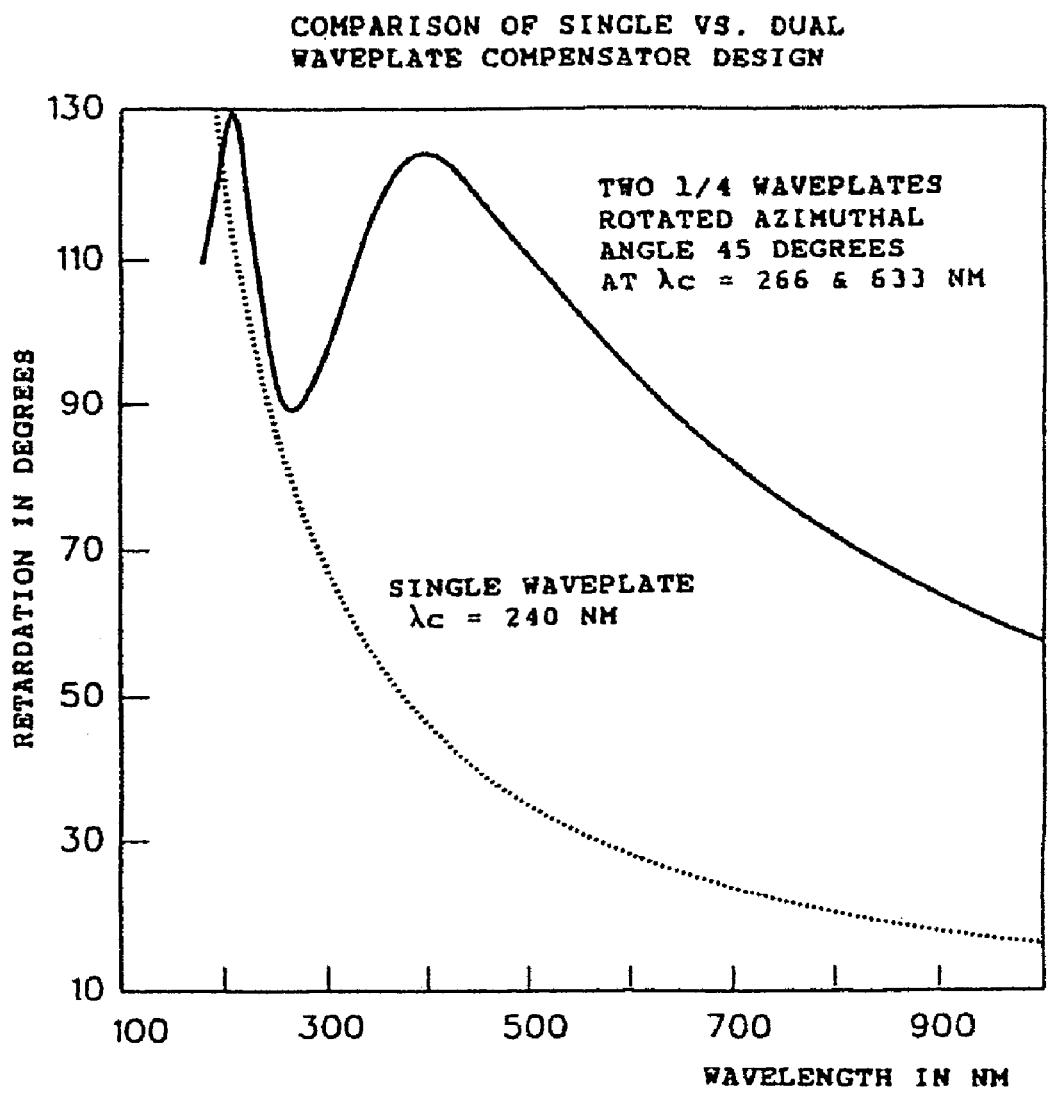
FIG. 10a shows a plot of a compensator retardation characteristic which depends as (1/wavelength), (dashed line), as well as a compensator characteristic, (solid line).

FIG. 10a shows a plot of a compensator retardation characteristic which depends as (1/wavelength), (dashed line), as well as a compensator characteristic, (solid line). The important thing to note is that a selected range of wavelengths over which a retardation of between seventy-five (75) and one-hundred-thirty (130) degrees is developed, is much greater for said compensator means. As disclosed in the Disclosure of the Invention Section of this Specification, a spectroscopic rotating compensator material system investigation system typically comprises at least one compensator means which produces a retardance of, preferably, between seventy-five (75) and one-hundred-thirty (130) degrees over a range of wavelengths defined by a selection from the group consisting of:

a. between one-hundred-ninety (190) and seven-hundred-fifty (750) nanometers;
b. between two-hundred-forty-five (245) and nine-hundred (900) nanometers;
c. between three-hundred-eighty (380) and seventeen-hundred (1700) nanometers;
d. within a range of wavelengths defined by a maximum wavelength (MAXW) and a minimum wavelength (MINW) wherein the ratio of (MAXW)/(MINW) is at least one-and-eight-tenths (1.8).

Acceptable practice however, provides for the case wherein said compensator provides a retardation vs. wavelength characteristic retardation range of less than Ninety (90) degrees over a range of Thirty (30.0) and less than one-hundred-thirty-five (135) degrees, over a range of wavelengths specified from MINW to MAXW by a selection from the group consisting of:
a. MINW less than/equal to one-hundred-ninety (190) and MAXW greater than/equal to seventeen-hundred (1700) nanometers;
b. MINW less than/equal to two-hundred-twenty (220) and MAXW greater than/equal to one-thousand (1000) nanometers;
c. within a range of wavelengths defined by a maximum wavelength (MAXW) and a minimum wavelength (MINW) range where (MAXW)/(MINW) is at least four-and one-half (4.5).

(NOTE, the specified values and ranges can not be achieved by single plates with (1/wavelength) retardation characteristics).

Figure 10B:
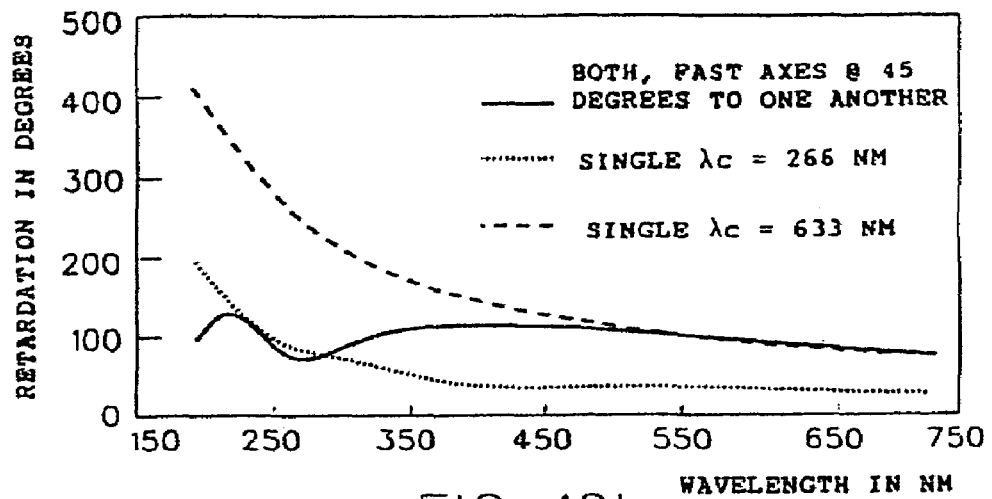
FIG. 10b shows calculated retardation vs. wavelength curves for two compensators which demonstrate (1/wavelength) retardation characteristics, (long and short dashed lines), and the retardation curve, (solid line), of a assembly as demonstrated in FIG. 9g1 which is arrived at by combining said two retarders with a 45 degree angle between the fast axes thereof.

FIG. 10b shows calculated retardation vs. wavelength curves for two compensators which demonstrate (1/wavelength) retardation characteristics, (long and short dashed lines), and the retardation curve, (solid line), of a assembly configuration as demonstrated in FIG. 9g1 which is arrived at by combining said two retarders with a 45 degree angle between the fast axes thereof.

Figure 10C:
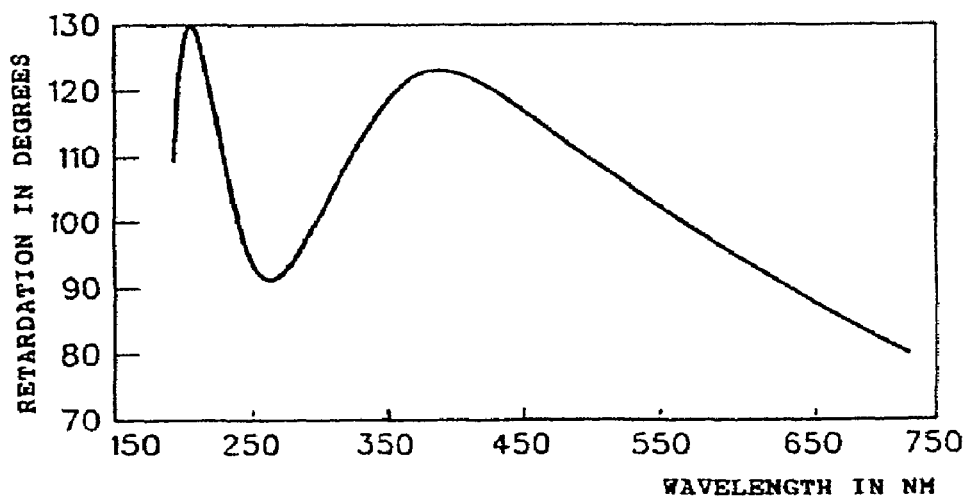
FIG. 10c shows a rescaled plot of the solid line curve shown in FIG. 10b.

FIG. 10c shows a re-scaled plot of the solid line curve shown in FIG. 10b.

Figure 10D:
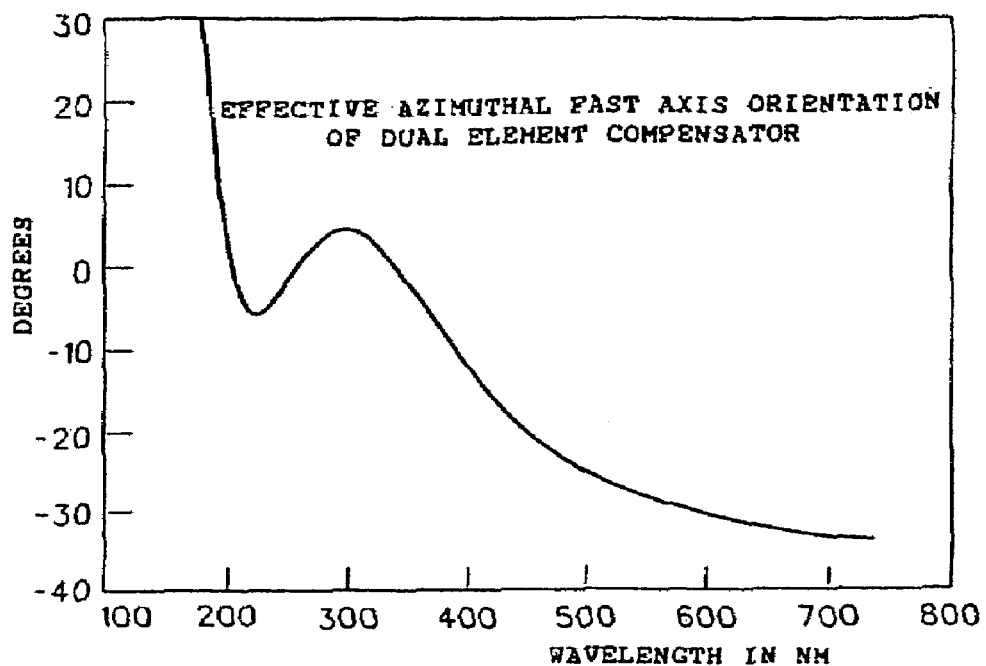
FIGS. 10d and 10e show results calculated for compensators as demonstrated in FIG. 9g1, wherein one waveplate is selected at 266 NM and the other at 633 NM., and wherein the fast axes are oriented at 45 degrees with respect to one another, over a wavelength range of from 190 to 730 NM.
Figure 10E:
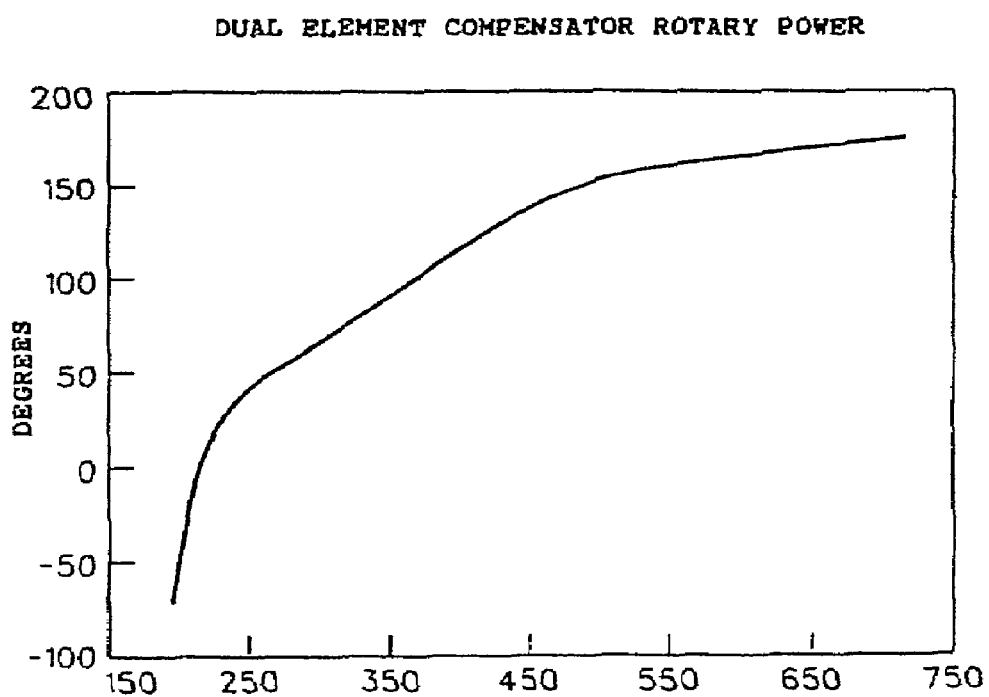

FIGS. 10d and 10e show results calculated for a compensator means as demonstrated in FIG. 9g1, wherein one waveplate is selected at 266 NM and the other at 633 NM, and wherein the fast axes are oriented at 45 degrees with respect to one another. The wavelength range is from 190 to 730 NM, (ie. deep UV to Visable). FIG. 10d shows the calculated effective fast axis orientation of a two plate compensator means and FIG. 10e shows the calculated effective rotary power. Also, as discussed in the Jones paper identified in the Background Section of this Specification, an arbitrary sequence of retarder elements can be mathematically represented by a single compensator means with "effective" retardance, fast axis and rotary power.

Figure 10G:
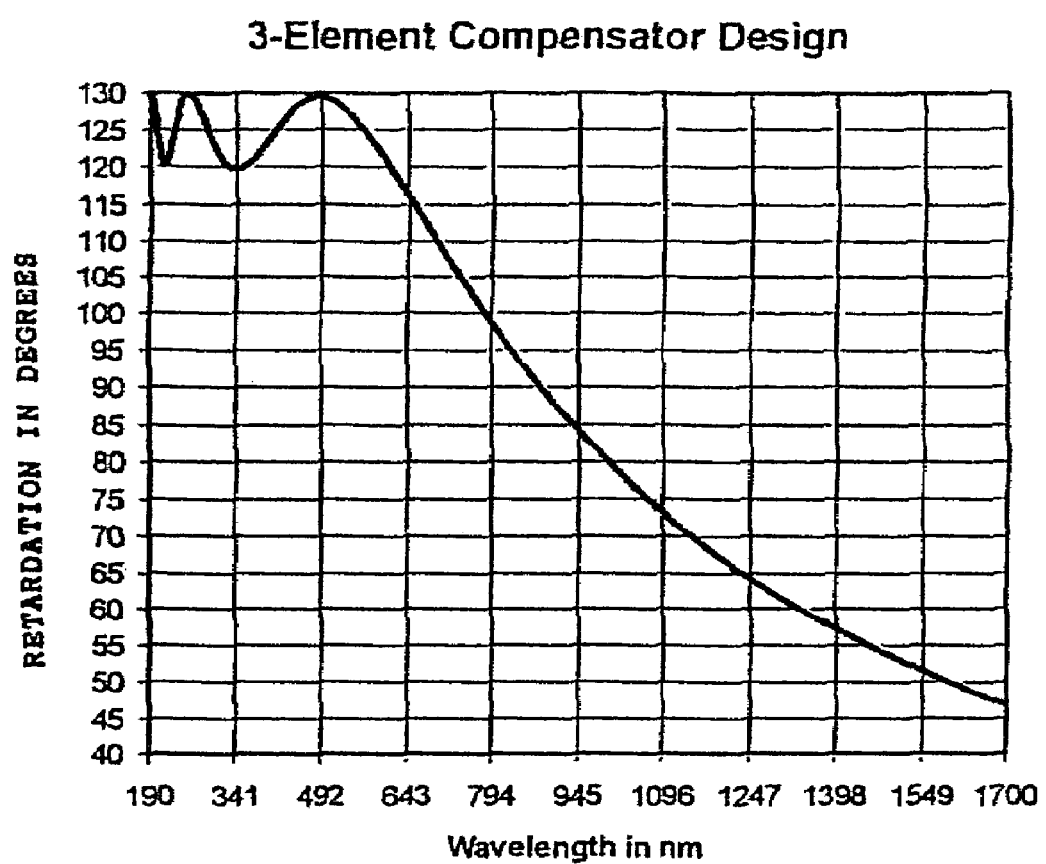

FIGS. 10f and 10g1 show that changing waveplate selection for a FIG. 9g1 compensator means configuration, and the angle between fast axes of the compensator means members thereof, provides alternative retardation plots over various wavelength ranges. FIG. 10f provides results for wavelengths between 245 and 850 NM, when waveplate selection involves 266 NM and 780 NM, and that angle between the fast axes is 50 degrees. FIG. 10g1 provides results between 380 and 1700 NM, for selection of waveplates at 532 NM and 1550 NM, and an angle between fast axes of 50 degrees. FIGS. 10f and 10g1 are included to show that compensator means design can be easily carried out, with the end result that retardations of between 75 and 130 degrees can be achieved over various wavelength ranges.

FIG. 10g2 shows retardation vs. wavelength for a three (3) Zero-Order plate element compensator as can be realized such as suggested by FIGS. 9g1, 9g2 and 9j. Note the retardation varies between about 47 degrees and 130 degrees over a wavelength range of 190 to 1700 nm. Said three (3) element compensator comprises a 422 nm quartz Zero Order waveplate sandwiched by two 633 nm quartz Zero Order waveplates. The azimuth of the 422 nm Zero Order waveplate is oriented +41 degrees with respect to the azimuth of the first 633 nm Zero Order plate, and the azimuth of the second 633 nm Zero Order Waveplate is oriented −33 degrees with respect to the azimuth of the first 633 nm Zero Order Waveplate. This compensator design then provides a retardance characteristic which varies over a range less than 90 degrees over a wavelength range, which retardance does not exceed 130 degrees. Note specifically that the retardation vs. wavelength characteristic retardation range is less than Ninety (90) degrees over a range bounded by Thirty (30.0) to less than one-hundred-thirty-five (135) degrees, over a range of wavelengths specified from a MINW of one-hundred-ninety (190), and a MAXW of seventeen-hundred (1700) nanometers, hence, even though the range of its retardation is between about 47 and 130 degrees, it is covered by Claim language which recited boundaries of 30 and less than 135 degrees.

Figure 10H:
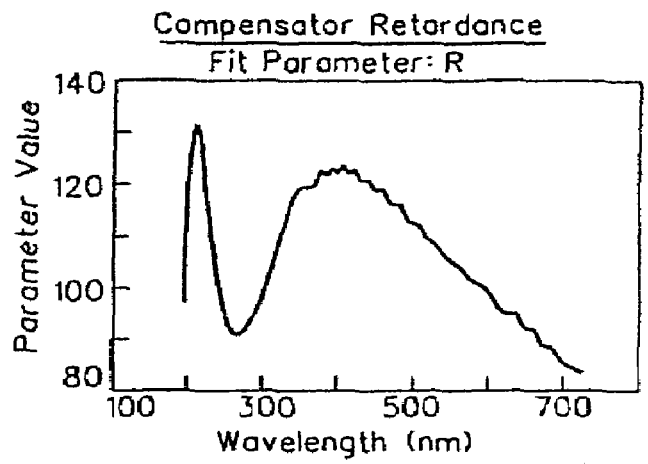
FIG. 10h shows experimentally determined compensator retardance as a function of wavelength. Note that, except for the presence of harmonic "wiggles", the curve closely corresponds to the calculated curve in FIG. 10c.
Figure 10I:
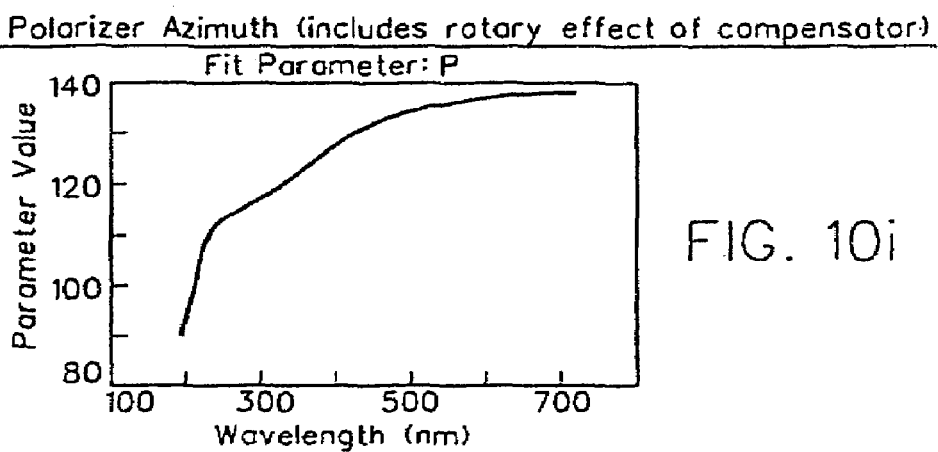
FIG. 10i shows experimentally determined effective input polarizer azimuthal angle, (including the rotary effect of the compensator). Note the agreement with FIG. 10e.
Figure 10J:
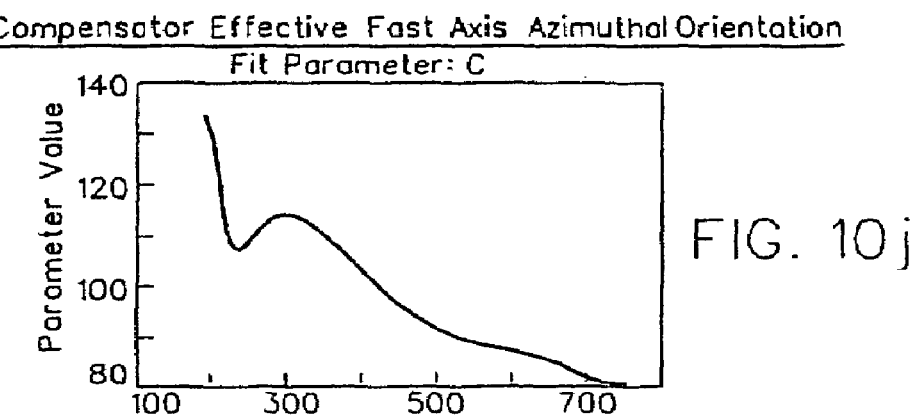
FIG. 10j shows the experimentally determined effective Fast Axis of the compensator azimuthal orientation. Note the agreement with FIG. 10d FIGS. 10k and 10L show experimentally determined depolarization factors 'c' factor 'b'.
Figure 10K:
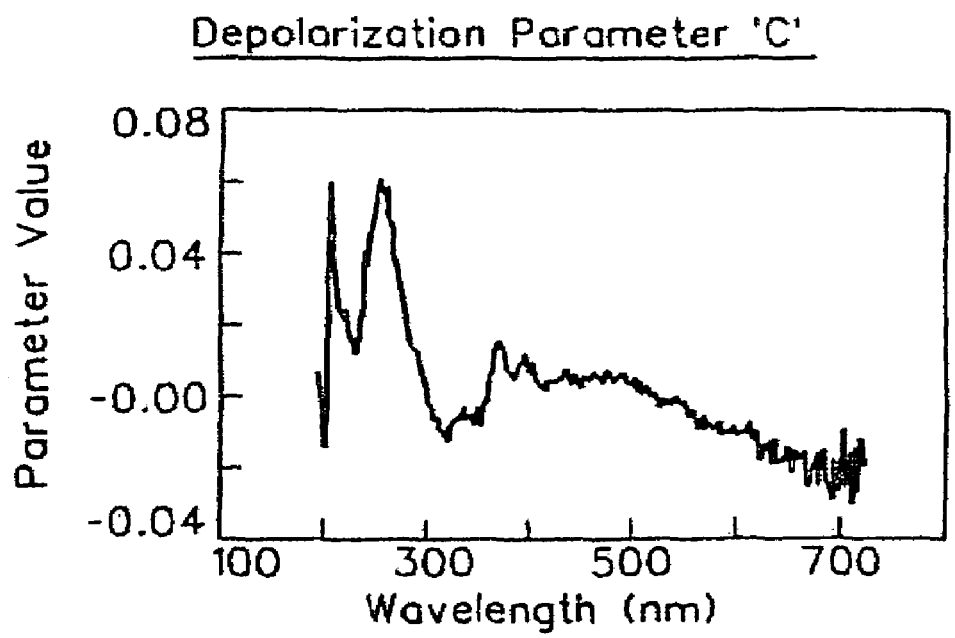
Figure 10L:
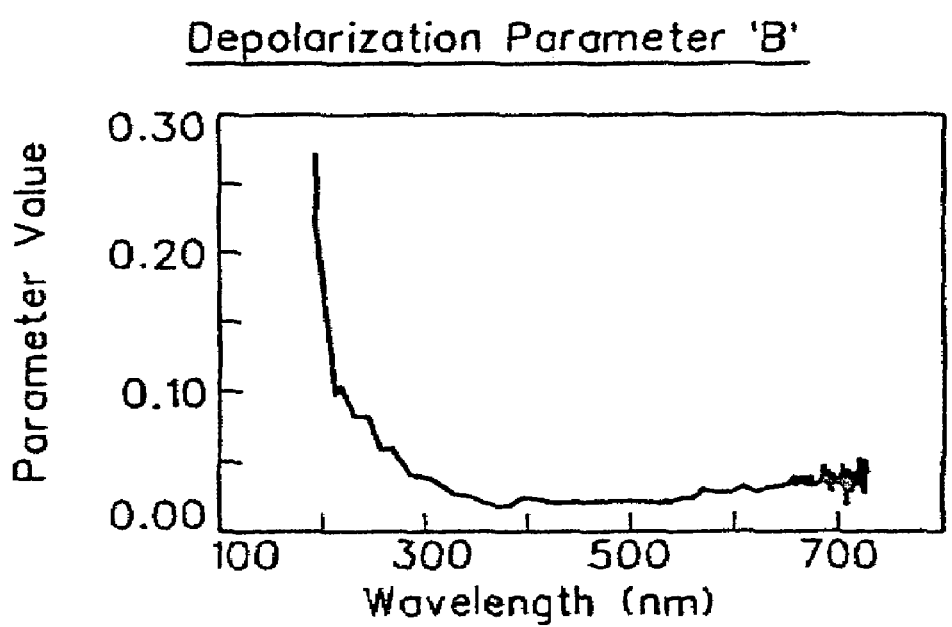

FIGS. 10h-10o show various experimentally obtained plots utilizing a J. A. Woollam CO. Inc. Rotating Compensator Ellipsometer System, (ie. the "M-2000", Registered Trademark). Curves in FIGS. 10h-10j were extracted using A.C. Normalization while curves in FIGS. 10k-10L were extracted using D.C. Normalization. In particular, FIG. 10h shows azimuthal Compensator Means Retardance as a function of Wavelength. Note that, except for the presence of harmonic "wiggles", (which are due to the imperfect alignment of the "effective" zero-order waveplate), the curve closely corresponds to the calculated curve in FIG. 10c. FIG. 10i shows Effective Input Polarizer Means Azimuthal Angle, (including the rotary effect of the Compensator). FIG. 10j shows the effective Fast Axis of the Compensator Means Azimuthal Orientation. FIG. 10k shows Depolarization factor 'c' and FIG. 10L shows Depolarization factor 'b'. (Note in particular the excellent agreement between plots in FIGS. 10c-10e, and FIGS. 10h-10j).

Figure 10M:
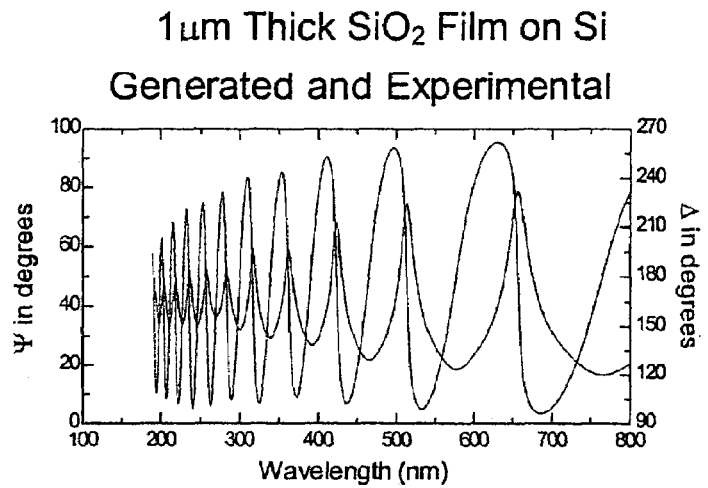
FIGS. 10m-10o show PSI and DELTA curves experimentally determined for silicon substrates with, respectively, 1 Micron, 250 Angstroms and 25 Angstroms of $SiO_2$ on the surface thereof. The experimentally determined data is essentially exact agreement with the generated data from a mathematical model fit.
Figure 10N:
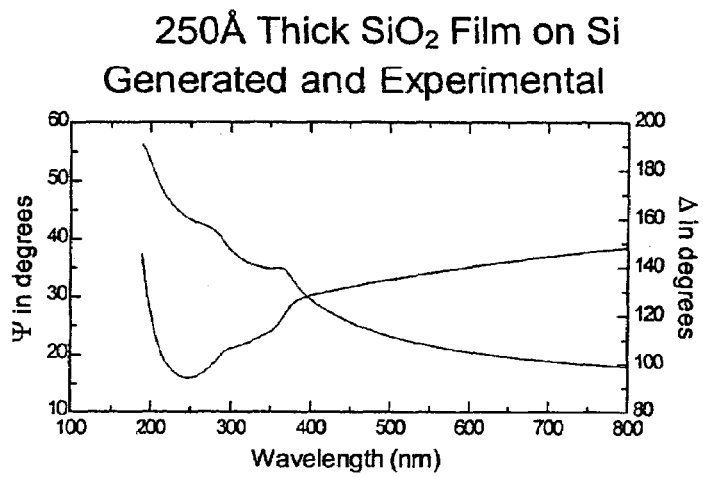
Figure 10O:
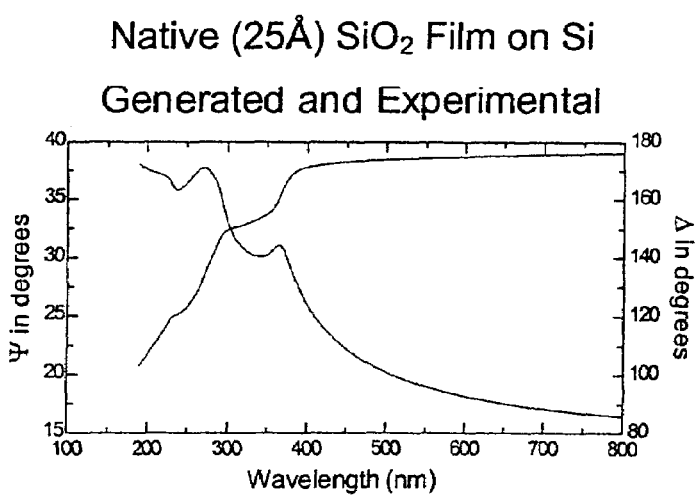

FIGS. 10m-10o show familiar PSI and DELTA Curves obtained with a Rotating Compensator Ellipsometer System, for Silicon Substrates on, respectively, 1 Micron, 250 Angstroms and 25 Angstroms of $SiO_2$ on the surface thereof.

It is noted that the described invention easily avoids the limitation inherent in the Patent to Aspnes, U.S. Pat. No. 5,877,589, which Patent was identified in the Background Section of this Disclosure, while providing excellent materials system investigation results. Further, the described invention also avoids utilization of "substantially-non-achromatic" compensator means with at least a ninety (90) degree range of retardance variance of an applicable wavelength range, hence avoids the limitations in the Aspnes et al. U.S. Pat. Nos. 6,320,657 B1 and 6,134,012, respectively, again while providing excellent materials system investigation results.

It is noted that the terminology Spectroscopic Rotating Compensator Material System Investigation System is to be interpreted sufficiently broadly to include Ellipsometers and Polarimeters with integrated electromagnetic radiation sources, and the like systems. In the Claims the terminology Spectroscopic Ellipsometer is utilized as being generic, with this in mind.

As well, it should be understood that a Mathematical Model developed to represent a Spectroscopic Rotating Compensator Material System Investigation System, (ie. Spectroscopic Ellipsometer), can be expressed as explicit equations for Intensity Transfer Function, or as equations for Coefficients of Terms which comprise such as a Transfer Function. However, in the context of performing Regression based evaluation of Calibration Parameters, it is to be understood that a Mathematical Model can "Effectively" provide such equations. That is, a computer program need not calculate a Transfer Function per se. to utilize mathematical relationships inherent therewithin. The terminology "Mathematical Model" and "Transfer Function, and "Coefficients of Terms" are to be interpreted sufficiently broadly so as to include the case where actual explicit equations therefore are not per se. generated, but where mathematical relationships inherent "Mathematical Model" and "Transfer Function, and "Coefficients of Terms" are utilized by a Regression based Calibration Parameter evaluation procedure. For instance, Numerical Equivalents to Specific Analytical Functions can be present and utilized in a Computer and be within the scope of the identified terminology, even though specific Analytical Equations are not per se., but only effectually, produced.

It is also to be appreciated that no other Spectroscopic Rotating Compensator Ellipsometer SYSTEM is known which comprises at once:

1. at least one Psuedo-Achromatic Characteristic Rotating Compensator Means (RC);
2. a Dispersive Optics (DO);
3. a Detector Elements (DE's) containing Detector System (DET) which comprises a Photo Array (PA); such that in use a Multiplicity of Material System (MS) Investigation Wavelengths in a Polychromatic Beam of Electromagnetic Wavelengths are simultaneously Monitored; and
4. is at least partially contained in an environmental control chamber.

In particular, other than as reported in Parent U.S. Pat. No. 5,872,630 and CIP's therefrom, no known Spectroscopic Rotating Compensator Material System Investigation System utilizes a, (possibly Calibration Parameter Parameterization aided), Mathematical Regression based METHOD approach to Evaluation of Calibration Parameters in a Mathematical Model of such a Spectroscopic Rotating Compensator Material System Investigation System, such that application thereof allows compensating the Psuedo-Achromatic, and other non-Ideal, aspects of a substantially Achromatic or Psuedo-Achromatic Rotating Compensator Means.

In addition, the above is particularly true where the spectroscopic rotating compensator material investigating system, (eg. ellipsometer or polarimeter), is placed into an environmentally controlled chamber.

It is emphasized that the described invention is considered to be particularly impressive as it is relatively easily constructed utilizing commercially available "Off-The-Shelf" Diode Array Spectrometer Systems, and non-ideal Compensators. The described invention conveniently provides, in a commercially realizable format, that which was thought to be, prior thereto and the version thereof presented in the Parent U.S. Pat. No. 5,872,630, essentially impossibly to provide in other than a prohibitively expensive, (and perhaps difficult to calibrate and utilize), single unit format.

It is to be understood that a Photo Array can be comprised of Diode-Elements, Charge-Coupled-Devices, Bucket-Brigade-Devices and equivalents.

It is also noted that Polychromatic Electromagnetic Beam Source can be comprised of a combined plurality/multiplicity of Laser Sources, and that Polychromatic Electromagnetic Beam Source can include an effective Polarizer therewithin, thereby eliminating the need for a separate Polarizer Means. Such cases are to be considered within the scope of the Claims with the effective Polarizer Means considered as the recited Polarizer Means.

It is further to be understood that the terminology "zero-order" is typically utilized herein to mean a single plate retarder/compensator, while the terminology "effective zero-order" is typically utilized herein to mean a zero-order retarder/compensator which is constructed from more that a single plate.

It is also to be understood that while there may be technical definitions in the literature which provide different meanings therefore, the terms "waveplate", "retarder" and "compensator" are utilized substantially interchangably in this specification.

It is also to be understood that the terminology "Straight-through" configuration provides as an effective material system, ambient atmosphere.

It is again noted that Zeiss Diode Array Spectrometer Systems identified by manufacturer numbers in the group: (MMS1 (300-1150 nm); UV/VIS MMS (190-730 nm); UV MMS (190-400 nm); AND IR MMS (900-2400 nm)); as well as Hamamatsu CCD Array Detectors, (Series S7030/S7031), with a quantum efficiency of 40% or more have been successfully utilized in the described invention system.

It is specifically to be understood that the terminology "Compensator means" is to be interpreted sufficiently broadly to include one or more than one compensator(s), and that for the purposes of this Specification and Claim interpretation, that as applied to a Compensator or Compensator Means:

"Substantially Achromatic" means that over a specified range of wavelengths the Retardation varies from just above 0.0 up to about thirty (30) degrees; and "Pseudo-Achromatic" means that over a specified range of wavelengths the Retardation varies less than Ninety (90) degrees, (ie. the maximum minus minimum retardation is less than 90 degrees), over a range of retardations with a minimum retardation of preferably at least Thirty (30) degrees and a maximum retardation of less than One-Hundred-Thirty-Five (135) Degrees.

"Non-achromatic" is to be interpreted to mean that retardance entered to a beam of electromagnetic radiation by a retarder/compensator at one wavelength is different from that entered at a different wavelength. For instance, the Aspnes et al. 012, 787 and 657 Patents suggest that if "an effective phase retardation value is induced covering at least from 90 degrees to 180 degrees", (012 Patent), over a range of wavelengths of 200-800 nm, such is definitive of a "Substantially-Non-Achromatic" compensator means.

The compensator means of the presently disclosed invention can be termed "Substantially Achromatic", but are sometimes more properly termed "Pseudo-achromatic" in that some do not produce uniform retardation at all wavelengths, but produce retardation which is far more uniform than, for instance, waveplates that provides retardance which varies proportional to (1/wavelength).

It is also to be understood that the "pin hole" present in a spatial filter can be on any functional shape, including round, oval, elliptical, rectangular and square.

It is also to be understood that while FIG. 1$c$ might imply that the disclosed invention is limited to a fixed Angle-of-Incidence (AOI), FIG. 1$d$ is to be interpreted to include systems in which a variable Anglea-of-Incidence (AOI) is possible.

It is to be understood that Detectors (DET) comprising a multiplicity of Detector Elements (DE's) can be of any functional type, (eg. Photodiode, CCD, Plasma etc.), can comprise one or more chips and can have any functional number of dimensions, (eg. linear, two-dimensional array, three dimensional array etc.).

Finally, it is again noted for emphasis that providing the described ellipsometer or polarimeter and the like systems which comprises detector systems comprising a multiplicity of Detection Elements (DE's) in a chamber in which the environment can be controlled by either purging or evacuation, enables obtaining of data corresponding to wavelengths which are absorbed by Oxygen or Water Vapor etc., very quickly as compared to the conventional practice which involves use of a monochromater and requires data be obtained at different wavelengths sequentially. Further, it is believed that a spectroscopic material system investigation system, (such as an ellipsometer or polarimeter), comprising a detector system which comprises a multiplicity of Detection Elements (DE's), which spectroscopic material system investigation system is inside an environmental control system comprising one or multiple chamber regions, is Patentable.

Recent Compensator Designs

Figure 11:
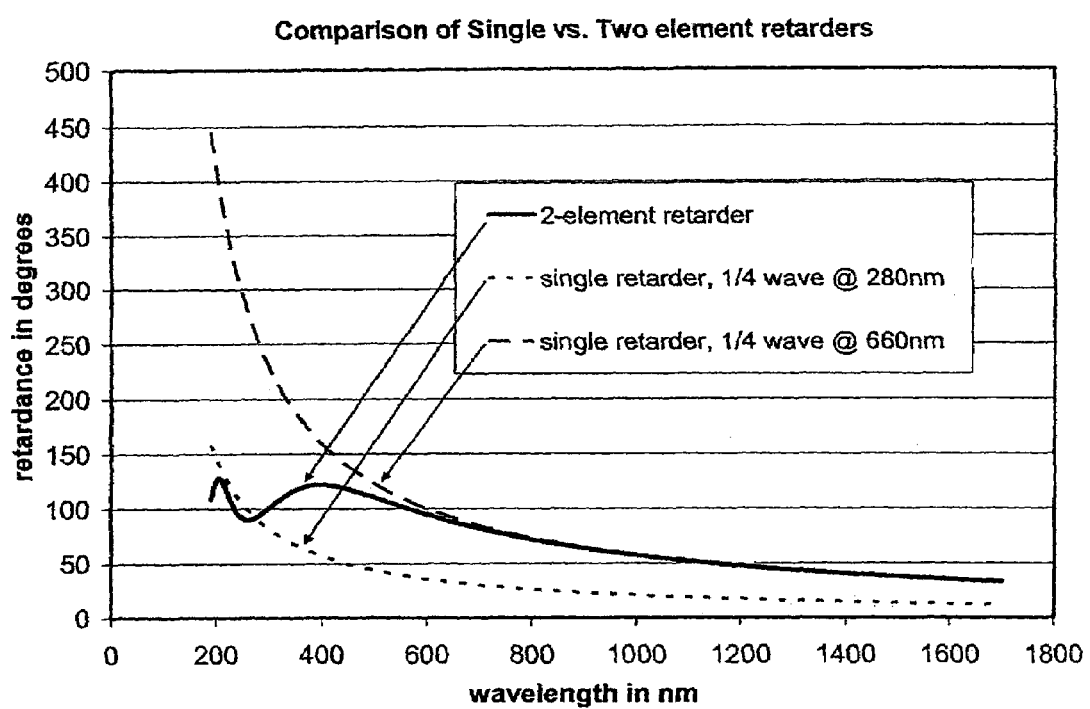
FIG. 11 shows retardance results from a retarder comprising two birefringent waveplates over a spectroscopic range.
Figure 12:
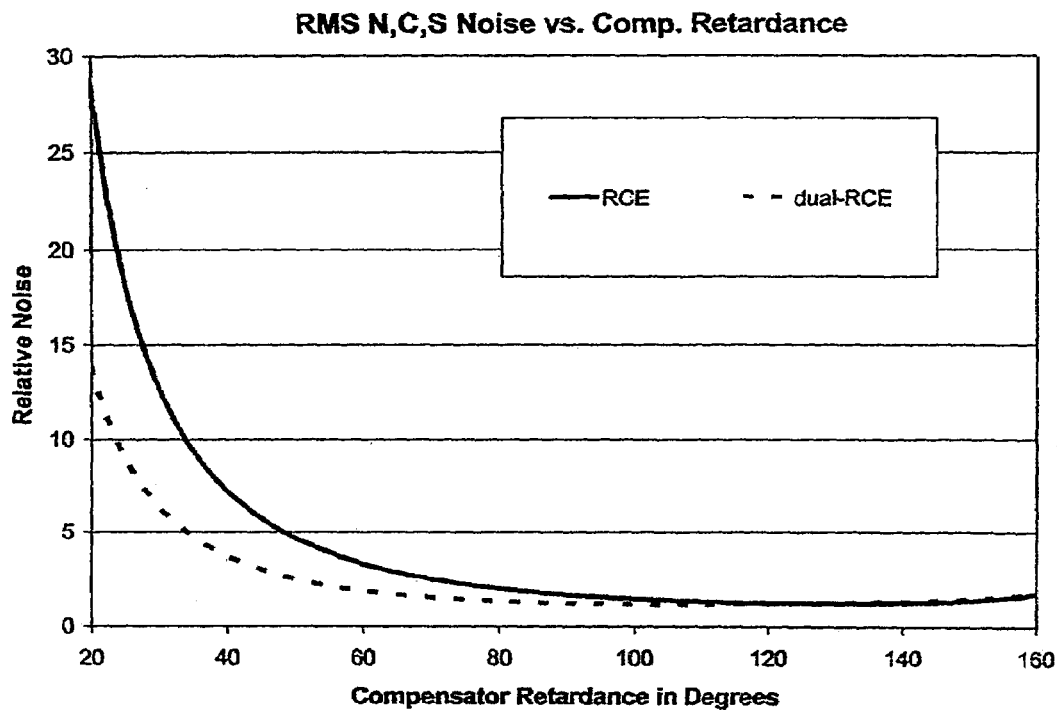
FIG. 12 shows the root mean squared (RMS) noise in ellipsometric parameters N, C and S.

Turning now to FIG. 11, as introduction, results from a retarder comprising two birefringent waveplates are shown. Note that the retardance varies from 35-130 degrees over the typical UV-VIS-NIR spectral range of 190-1700 nm. FIG. 2 shows the Root Mean Squared (RMS) noise in the ellipsometric parameters;

N=cos(2ψ);
C=sin(2ψ)cos(Δ); and
S=sin(2ψ)sin(Δ);

for the rotating compensator ellipsometer (RCE) and dual rotating compensator ellipsometer (dual-RCE) configurations as a function of compensator retardance. See FIG. 23 for insight to the construction of a rotating compensator ellipsometer (RCE) with one or two of the shown Compensators (C), (C') (C") considered as present. Continuing, for said rotating compensator ellipsometer (RCE) configuration it is disclosed that it has been determined to be beneficial to keep the retardance between 80 and 160 degrees, as this keeps the relative RMS N,C,S noise to less than 2.0. In that regard the dual-RCE configuration is slightly more forgiving over the retardance range is 60-160 degrees. It should be appreciated that FIGS. 1 and 2 show that using birefringent waveplates through which a beam of electromagnetic radiation is caused to pass, in wide spectral range rotating compensator ellipsometer systems, compromises the noise performance of the system.

In view of the above disclosure, it is disclosed that an alternative approach to effecting retardance is by total internal reflection. FIGS. 13a and 13b show retardance vs. internal angle and wavelength, (at a given angle), for the fused silica/air interface. Note that the change in retardance vs. wavelength for total internal reflectance is very small compared to the (1/wavelength) dependence of birefringence-induced retardance. Fresnel rhomb retarders which are based on this effect are readily available. However, a typical ¼ wave Fresnel rhomb design translates the beam significantly, and the retardance also changes significantly as a function of beam angle, making it impractical to use a Fresnel rhomb in a rotating compensator style ellipsometer or polarimeter design. FIG. 14a shows a Typical Wave ¼ wave 90 degree retardance Fresnel Rhomb and demonstrates the translation effect. FIG. 14b shows a known approach to combining two Fresnel Rhombs to achieve a substantially non-translated beam. The rhombs each have first (RS1), second (RS2), third (RS4) and forth (RS4) sides, said first (RS1) and third (RS3) sides being parallel to one another, and said second (RS2) and forth (RS4) sides being parallel to one another, said first (RS1) and second (RS2), and said third (RS3) and forth (RS4) sides of said first Freshnel Rhomb meeting one another at angles greater than ninety degrees therebetween, and said second (RS2) and third (RS3) sides and said first (RS1) and forth (RS4) sides thereof meeting one another at angles less than ninety degrees therebetween. Note that said at least two parallelogram shaped rhombs are oriented with their first (RS1) and third (RS3) sides being substantially parallel to one another. In use a beam of electromagnetic radiation caused to enter the first (RS1) side of the first Freshnel Rhomb, at a substantially normal angle thereto, then proceeds so that it internally reflects from said forth (RS4) and second (RS2) side thereof, then exits said third (RS3) side thereof in a direction such that it then enters the first (RS1) side of the second Freshnel Rhomb at a substantially normal angle thereto, then proceeds so that it internally reflects from said second (RS2) and forth (RS4) side thereof, then exits said third (RS3) side thereof. Said system is distinguished over known configurations in that it is characterized in that at least one of the sides (RS1) (RS2) (RS3) (RS4) of at least one of the parallelogram shaped rhombs has a coating thereupon which has a different refractive index than does the material from which said corresponding parallelogram shaped rhomb is comprised. Preferred practice is to coat sides (RS2) and (RS4) of each rhomb. The angles of the parallelogram shaped rhomb can be 36, 144, 36, and 144 degrees or 45, 135, 45 and 135 degrees, and the rhombs can be fabricated from of fused silica, with the coating being a material, (eg. MgF$_2$), with a lower refractive index.

Figure 14C:
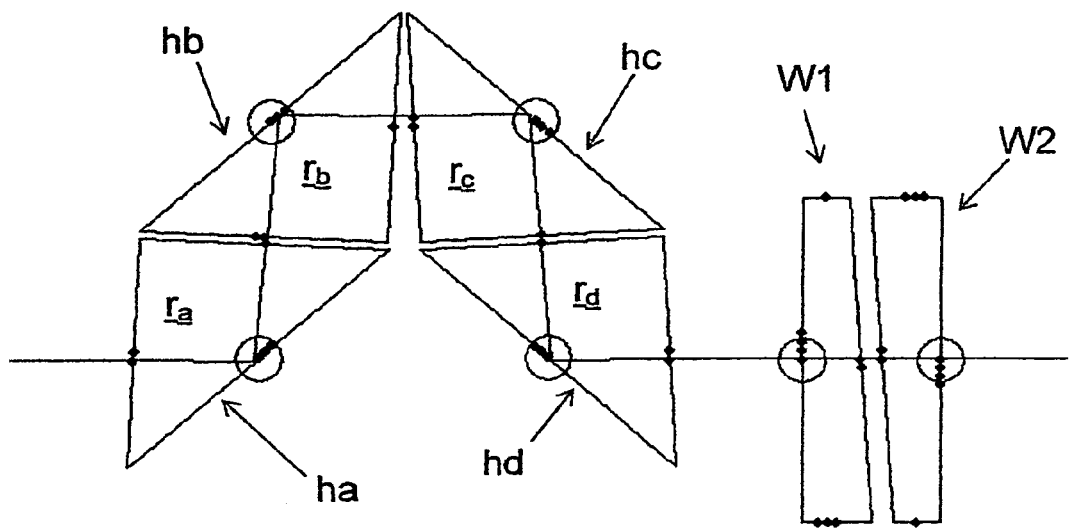
FIG. 14c shows a variation on the FIG. 14b system comprising four right angle prisms and optional wedge elements as also shown in FIG. 22b.
Figure 14D:
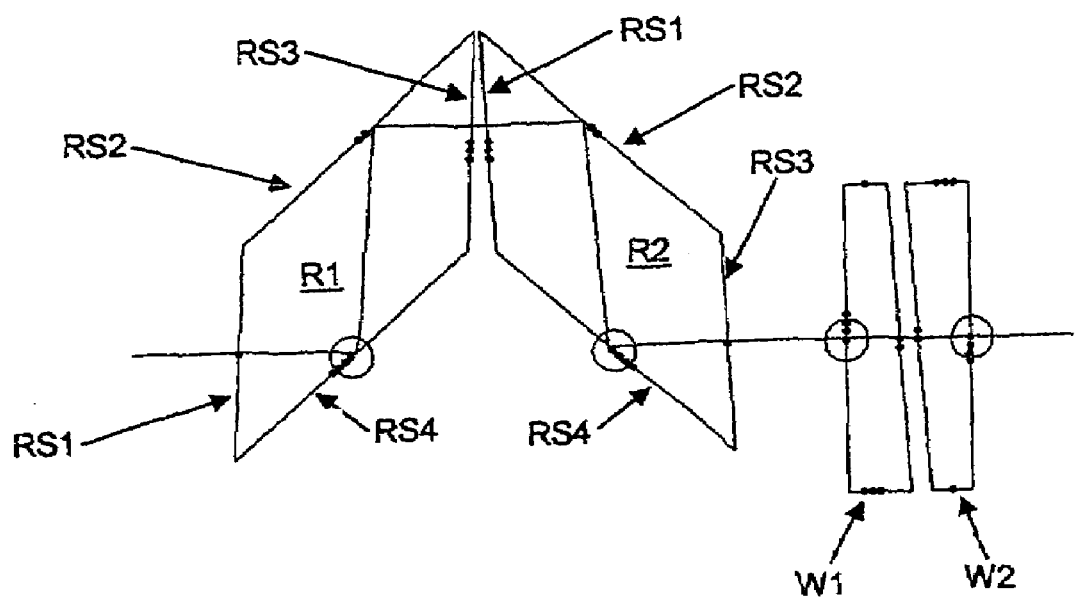
FIG. 14d shows how two Fresnel rhombs, each of which is equivalent to two right angle prisms in FIG. 14c, and two wedges, can be combined to result in a non-deviated beam.
Figure 19A:
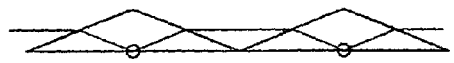
FIGS. 19a, 19b, 20a and 20b show that the most useful property of the new retarder design is that as the angle of the input beam is changed, the resulting transmitted bean angle does not change.
Figure 20A:
Figure 19B:
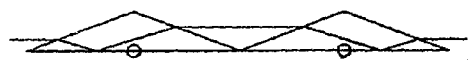
Figure 20B:
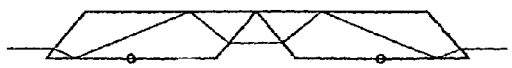
Figure 21A:
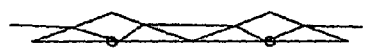
FIGS. 21a-21f show very small beam polarization change, in terms of PSI and DELTA, for a given change in beam angle.
Figure 21D:
Figure 21B:
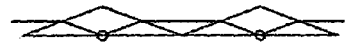
Figure 21E:
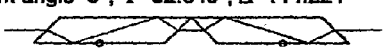
Figure 21C:
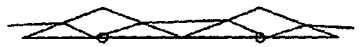
Figure 21F:

FIG. 14c shows a variation on FIG. 14b which is believed new and novel even without surface coatings. Shown are four similar right angle prisms, (ie. first (ra), second (rb), third (rc) and forth (rd)), having sides opposite their right angles of, respectively, (ha) (hb) (hc) and (hd). As viewed in FIG. 14c the first right angle prism (ra) is positioned so that its side (ha) opposite the right angle thereof is facing downward and to the right. Directly above the first right angle prism (ra) is the second right angle prism (rb), which is oriented so that its side (hb) opposite the right angle thereof is facing upward and to the left. Directly to the right of the second right angle prism (rb) is the third right of right angle prism (rc) which is oriented so that its side (hb) opposite the right angle thereof is facing upward and to the right. Finally, positioned directly below the third right angle prism (rc) is the forth right angle prism (rd), oriented so that its side (hd) opposite the right angle thereof is facing downward and to the left. Note that the sides of each element (ra) (rb) (rc) and (rd) adjacent to the right angles thereof are identifiable as "right angle sides". It is also noted that the sides of elements (ra) (rb) (rc) and (rd) opposite the right angles can be coated with a material of different refractive index material, (eg. where said elements are made of fused silica the coating can be, for instance, 35 nm of lower index MgF$_2$). Such a coating makes the retardance entered by a total internal reflection from a side opposite the right angle thereof substantially achromatic with range of retardation. Also shown in FIG. 4c are two optional Wedge Elements (w1) and (w2), the purpose of which is described with respect to FIG. 22b. It is noted that the design of FIG. 14b is also believed to be new and novel when a coating is applied to a reflective outer surface thereof. FIG. 14d shows how two Fresnel Rhombs (R1) (R2) which are equivalent to the four right angle prisms (ra)+(rb) and (rc)+(rd) of FIG. 14c, and two wedges (w1) (w2), can be combined to result in a non-deviation of a beam (B) caused to pass therethrough. The angles of the Rhombs are 45, 135, 45 and 135 degrees. Coatings with a different refractive index from that of the material from which the Rhomb is comprised can be present on surfaces thereof as well, much as for the system in FIG. 14b.

It is noted that when applying the embodiments of FIGS. 14b and 14d, the Beam (B) is typically not entered exactly along a normal to the surface entered, (eg. (RS1) in FIG. 14d). This diverts unwanted depolarizing secondary bounces out of the primary beam and such a beam entry locus can be termed "substantially normal" to the surface where the off-normal angle is sufficient to divert said reflections. A typical off-normal angle is about three (3) degrees which deviates transmitted secondary beams by about six (6) degrees. This is sufficient to provide separation from the primary transmitted beam. Also, as presented with respect to FIG. 22b, the Wedges (w1) (w2) can be rotated with respect to one another and/or simultaneously to result in a non-deviated beam, (B).

Figure 13C:
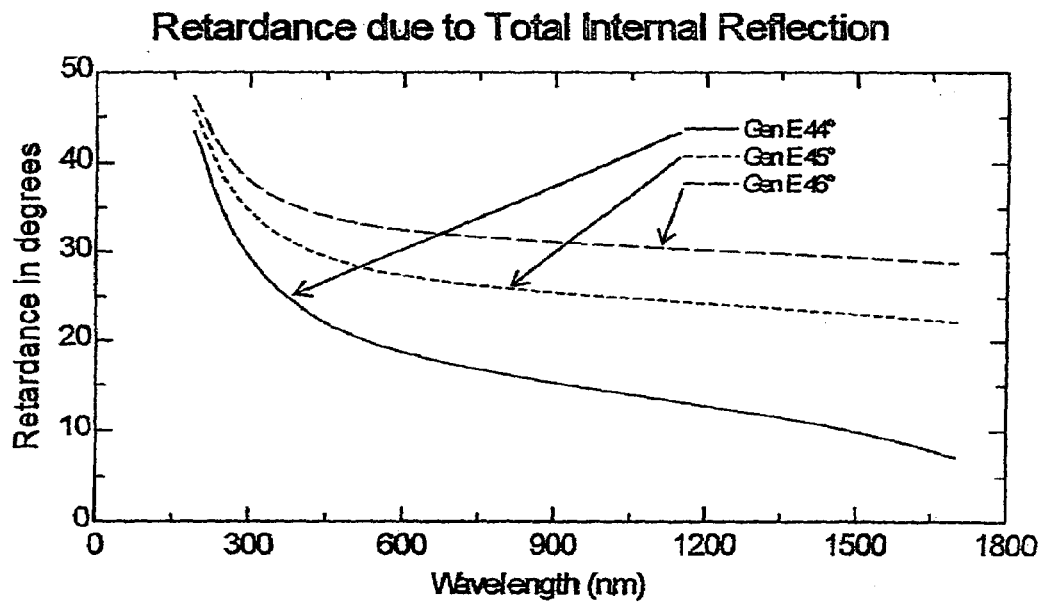
FIG. 13c shows retardance vs. and wavelength, (at a given angle), for the fused silica/air interface for a system as shown in FIG. 14c.
Figure 13A:
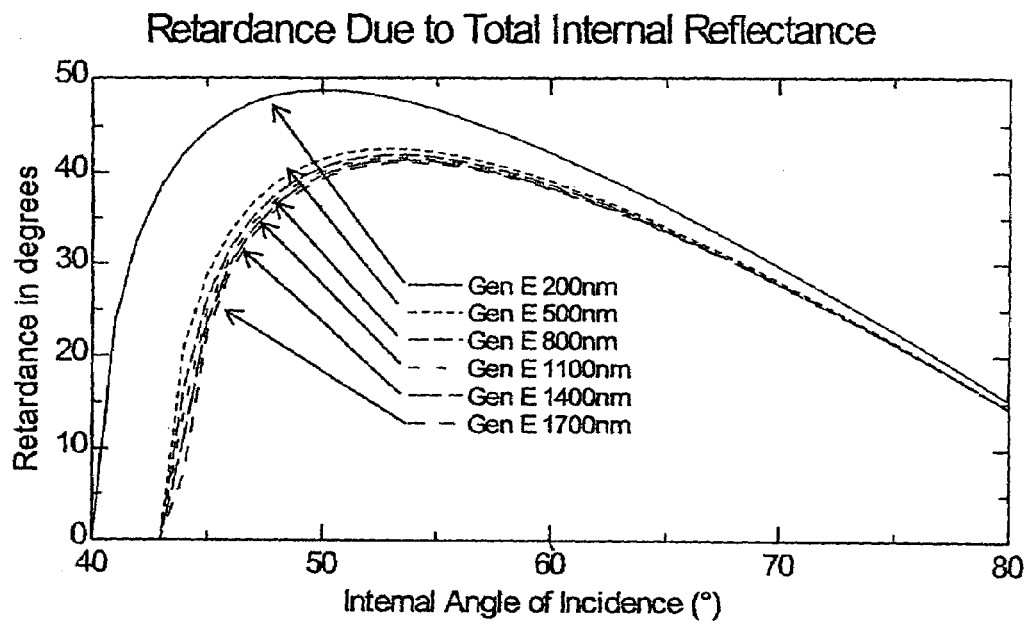
FIGS. 13a and 13b show retardance vs. internal angle and wavelength, (at a given angle), for the fused silica/air interface.
Figure 13B:
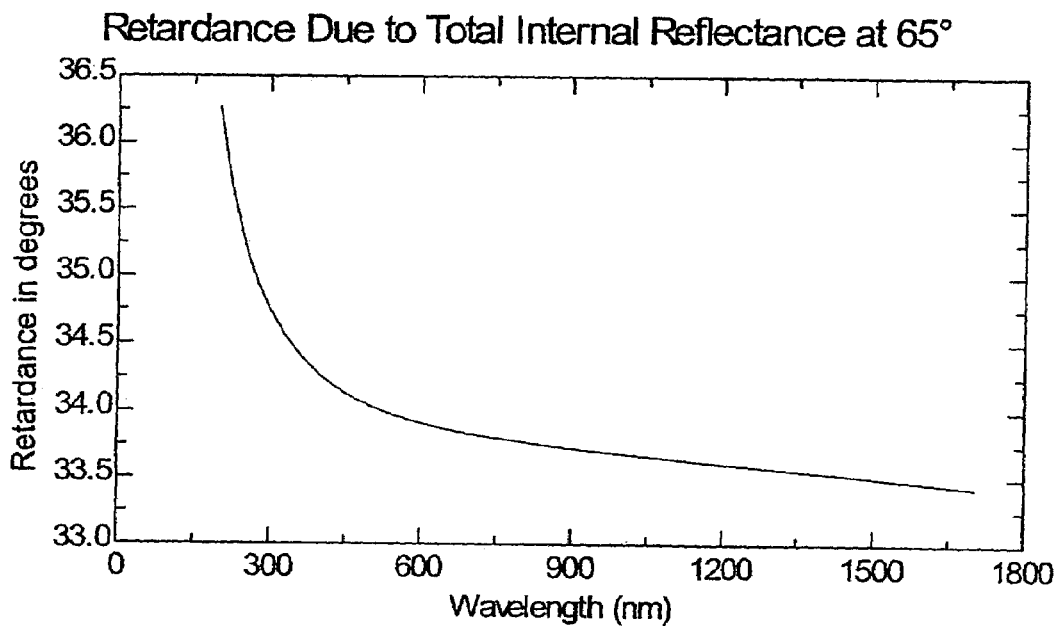
Figure 13D:
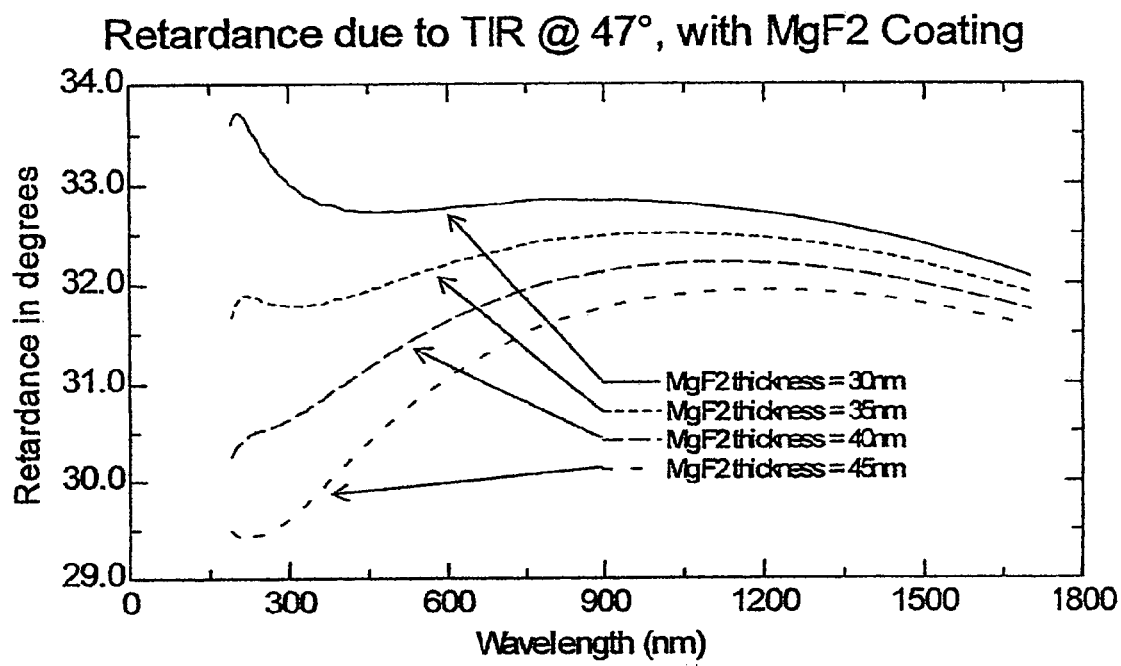
FIG. 13d show results as in FIG. 13c, but for a system having a different refractive index coating on reflective surfaces of a system as shown in FIG. 14c.

FIG. 13c shows retardance vs. internal angle and wavelength, (at a given angle), for the fused silica/air interface for a system as shown in FIG. 14c, and FIG. 13d show results as in FIG. 13c, but for a system having a different refractive index coating on reflective surfaces of a system as shown in FIG. 14c. FIGS. 13a and 13c indicate that near a 45 degree angle of incidence the retardance varies strongly as a function of both wavelength and angle of incidence. A total retardance, resulting from four reflections, varies between 180 degrees at 190 nm to less than 90 degrees at 1700 nm. FIG. 13d indicates that including a coating on the side of the elements (ra) (rb) (rc) and (rd) opposite their right angle can make said result more achromatic. For instance, where the elements (ra) (rb) (rc) and (rd) are made from Fused Silica, and the coatings are between 30-45 nm of $MgF_2$, the total retardation for four total internal reflections in the described system is between 116 and 136 degrees over a range of wavelengths of 190 nm-1700 nm.

Continuing, the present invention retarder design uses an even number of multiple total internal reflections to provide the desired amount of retardance. Furthermore, the geometry of the reflections is such that a given change in the input beam angle causes opposite changes in the internal angles of reflection, and therefore. (since the slope of the retardance vs. angle curve above is relatively linear over small angle ranges), the net retardation of the system does not change to the 1st order for small changes in the beam angle. One embodiment of the new retarder system is shown in FIG. 15. Shown are two triangular isosceles prisms, each with angles of 26, 128, and 26 degrees. Each triangular shaped prisms each has:

first (TS1) and second (TS2) sides of equal length which project from one another at an angle greater than ninety degrees therebetween, and a third side (TS3) oriented opposite said greater than ninety degree angle, said at least two similar triangular shaped prisms being oriented with respect to one another such that the third (TS3) sides thereof are substantially colinear;

such that a beam of electromagnetic radiation caused to enter the first side of the first thereof, at a non-normal angle thereto, is refracted so that it internally reflects from said third side thereof, then exits said second side thereof in a direction such that it then enters the first side of another thereof at a non-normal angle thereto, is refracted so that it internally reflects from said third side thereof, then exits said second side thereof. The prisms can be fabricated from of fused silica.

Another embodiment of the new retarder system is shown in FIG. 16. Shown are two parallelogram rhombs, with angles of 36, 144, 36, and 144 degrees. Said parallelogram shaped rhombs, each have first (RS1), second (RS2), third (RS3) and forth (RS4) sides, said first (RS1) and third (RS3) sides being parallel to one another and said second (RS2) and forth (RS4) sides being parallel to one another, said first (RS1) and second (RS2), and said third (RS3) and forth (RS4) sides of the first parallelogram shaped rhomb meeting one another at angles greater than ninety degrees therebetween, and said second (RS2) and third (RS3) sides and said first (RS1) and forth (RS4) sides thereof meeting one another at angles less than ninety degrees therebetween. Said at least two parallelogram shaped rhombs are oriented with their second (RS2) sides being substantially colinear and with their forth (RS4) sides thereof being substantially colinear, such that a beam of electromagnetic radiation caused to enter the first side (RS1) of the first parallelogram shaped rhomb, at a non-normal angle thereto, is refracted so that it internally reflects from said forth (RS4) and second (RS2) sides thereof, then exits said third (RS3) side thereof in a direction such that it then enters the first (RS1) side of the second thereof at a non-normal angle thereto, is refracted so that it internally reflects from said second (RS2) and forth (RS4) side thereof, then exits said third (RS3) side thereof. The parallelogram shaped rhomb can be fabricated from of fused silica.

Note that both the FIG. 15 and FIG. 16 embodiments have input and output surfaces into which a beam is entered, and out of which is exits, respectively, said surfaces serving to refract the beam in use. Other surfaces at which total internal reflection occurs are used to enter retardance. It is noted that the Fresnel losses at the refracting interfaces result in a relative attenuation for orthogonally polarized beams. The orthogonal beams are typically denoted p and s for light polarized parallel and perpendicular to the plane of incidence. The relative attenuation and retardation of an optical element can be quantified by the equation below, which is similar to the standard ellipsometry definition. In this case, Tp and Ts are the complex amplitudes of the orthogonal beams which are transmitted through the prism, (ψ) is the relative attenuation, and (Δ) is the retardance:

$$Tp/Ts = \tan(\psi) e^{i(\Delta)}.$$

An ideal retarder changes only the relative p-to-s phase, (ie. the retardation), of the beam, and for said case (ψ)=45 degrees. For the current invention, the (Δ) value depends on the number and angle of refracting surfaces in the design. For the triangle design (ψ) is about 57 degrees, and for the rhomb design (ψ) is about 53 degrees. Since (ψ) is dependent on the index of refraction, it varies a few degrees over the 190-1700 nm spectral range). While the (ψ) value of the retarder does have to be determined in the ellipsometer/polarimeter system calibration, the sensitivity and accuracy of the instrument has been found to not be significantly degraded as long as (ψ) is not too far from 45 degrees. It is noted that the beam enters and exits the elements at near a Brewster angle of incidence, hence substantially 100% of the p polarized light is transmitted through the system.

The geometry and symmetry of the elements results in a number of very useful properties. For example, FIGS. 17a, 17b, 18a and 18b show that if the sequential elements are translated up or down as a unit, the exiting beam remains collinear with the input beam. If the sequential elements are rotated, FIGS. 19a, 19b, 20a and 20b show that the exiting beam angle is unchanged, (though it is slightly translated).

FIGS. 21a, 21b, 21c, 21d, 21e, 21f show that the most useful property of the new retarder design is that as the angle of the input beam is changed, the resulting polarization properties (ψ) and (Δ) change very little. This is because the geometry and symmetry of the designs are such that changes in the refraction and total internal reflection angles have opposite signs for the two elements shown in the system of FIGS. 17a, 17b, 18a and 18b, which in turn cancels change in ($\psi$) and ($\Delta$) vs. input beam angle to a 1st order approximation. To give a feel for the results achieved by a present invention system, typically the change in ($\psi$) and ($\Delta$) for a one degree change in beam angle is approximately 0.01 degree. Note that FIGS. 21a-21f show that:

Beam angle=+1 degrees, ($\psi$)=56.953, ($\Delta$)=70.425;
Beam angle=0 degrees, ($\psi$)=56.940, ($\Delta$)=70.419;
Beam angle=−1 degrees, ($\psi$)=56.953, ($\Delta$)=70.425;
Beam angle=+1 degrees, ($\psi$)=52.357, ($\Delta$)=114.232;
Beam angle=0 degrees, ($\psi$)=52.349, ($\Delta$)=114.221;
Beam angle=−1 degrees, ($\psi$)=52.357, ($\Delta$)=114.232.

The net relative attenuation and retardance ($\psi$) and ($\Delta$) of the system can be controlled by adjusting the number of total internal reflections (determined by the number and length of the elements), the angles of refraction and reflection (determined by the prism and/or rhomb angles), and the material used to fabricate the elements.

Any transparent, optically isotropic material can be used for the elements, though care should be taken in mounting the elements to minimize strain-induced birefringence. Fused silica is ideal for the UV-VIS-NIR spectral range, but $CaF_2$ or $MgF_2$ is preferable in the DUV, and Si, Ge, ZnSe, KRS5, etc. are suited for use in the IR. Presently, preferred embodiment designs use fused silica, and have the following properties over a wide 190-1700 nm spectral range:

triangular prisms: ($\psi$)=56.382–59.286;
($\Delta$)=67.801–81.290;
parallelogram rhombs:
($\psi$)=51.976–54.271;
($\Delta$)=109.795–135.7010.

Said examples are not to be considered limiting, however, and other designs are possible, using different materials, angles, and/or geometries. For instance, it might be beneficial to provide for substantially normal angle entry and exit thereby avoiding the effect on ($\psi$), but the key element of any design is that symmetry is employed to enable the following properties:

1. The locus of the beam is not deviated as the system is translated;
2. The angle of the beam locus is not deviated as the system is rotated;
3. The change in polarization properties are minimal for changes in the input beam angle.

Figure 22A:
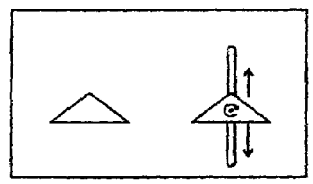
FIG. 22a demonstrates translation and rotation capability for an element of a two sequential element retarder system.
Figure 22B:
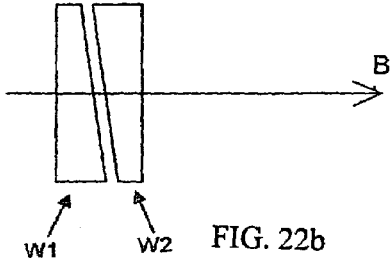
FIG. 22b shows a two wedge system which allows for relative rotation therebetween.

Another beneficial aspect of the disclosed design is that, since at least two elements are present, if the elements are not perfectly fabricated and/or aligned, the height and/or tilt of at least one of the elements can be adjusted with respect to the other such that the input beam is substantially undeviated in position and angle by the system. FIG. 22a demonstrates a system for accomplishing this by allowing translation and/or rotation of an element, and FIG. 22b shows an additional sequential two wedge (w1) (w2) system wherein relative rotation of one wedge with respect to the other provides a similar benefit. A system can then include at least one selection from the group consisting of:

at least one of the sequential elements has a mechanism for translating and/or tilting the element, for the purposes of aligning the system such that the output beam is substantially undeviated from said input beam;
there is present an additional sequential two wedge system wherein relative rotation of one wedge with respect to the other and/or combined wedge rotation can be performed for the purposes of aligning the system such that the output beam is substantially undeviated from said input beam.

It is also noted that when practicing Beam (B) deviation correction via Wedge (w1) (w2) rotations, relative rotation of one wedge with respect to the other and combined rotations of both Wedges (w1) and (w2) can be practiced.

It is noted that while not shown or preferred, a system could comprise such as one Triangular shaped element and one Trapezoidal shaped element. Such an arrangement can be viewed as a sequence of a FIG. 19a and FIG. 20a embodiment, perhaps with one of the FIG. 19a prisms removed and with one of the FIG. 20a rhombs removed. Careful attention to preserving effective symmetry is required in any such embodiment, however.

It is also noted that only a single primary beam is transmitted through the disclosed systems, as the secondary reflections from the refracting interfaces do not re-enter the primary beam path. This means that only a single polarization state is present in the transmitted beam. In contrast, multiple reflections from the parallel surfaces of birefringent plate retarders result in beam depolarization which can degrade the ellipsometer/polarimeter accuracy if not accounted for properly.

It is noted that the coating of, for instance, a material of different refractive index material, (eg. where said elements are made of fused silica the coating can be, for instance, 35 nm of $MgF_2$, which has a lower index), applied to a totally internally reflecting surface described with respect to FIGS. 14b and 14c can be applied in any of the embodiments in FIGS. 15, 16 17a, 17b, 18a, 18b, 19a, 19b, 20a, 20b, 21a-21f and 22a and 22b. Further, such a coating can be beneficially placed on non-totally internally reflecting surfaces thereof to reduce reflections therefrom.

It is noted that as regards, for instance, FIGS. 14b, 14d and 16, the rhombs, (eg. (R1) and (R2) in FIG. 14d), are oriented as functional mirror images of each other, while the side the input beam enters is, in both instances, labeled (RS1). It is felt this was the best way to disclose the invention, however, it might lead to some confusion regarding angles between, say, sides (RS1) and (RS2). In the foregoing discussion that angle is identified as being greater than 90 degrees. This is valid for the first (RS1) shown rhomb. For purposes of understanding the foregoing discussion, however, in mirror image the sides (RS1) and (RS3) in the second rhomb (RS2) can be considered reversed when the angles therebetween are described as are those in the first rhomb (RS1).

Figure 23:
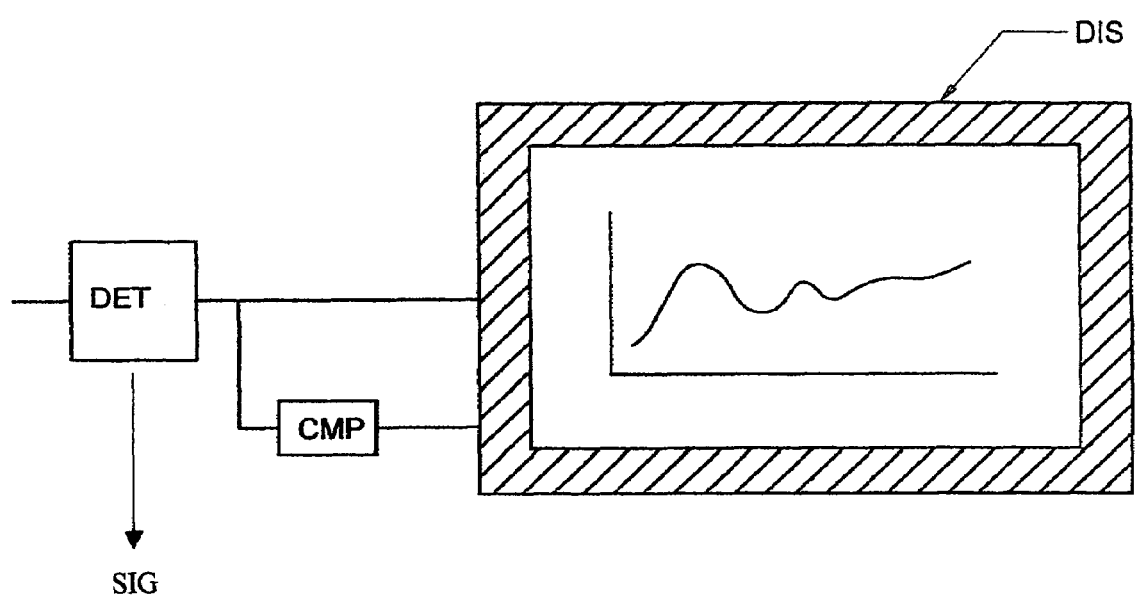
FIG. 23 shows that tangible and concrete effects can be realized using signals from a detector, such as display.

FIG. 23 is included to show that tangible and concrete effects can be realized using signals from a detector (DET), directly or after analysis by CMP), such as display (DIS) or application of a Signal (SIG).

Finally, it is to be understood that while numerous examples of ellipsometer systems are provided herein, none thereof are limiting. Except as limited by specific Claim language any Rotating Compensator Ellipsometer or Polarimeter etc. system using any compensator design, is to be considered as being within the scope of the Claims.

Having hereby disclosed the subject matter of this invention, it should be obvious that many modifications, substitutions and variations of the present invention are possible in light of the teachings. It is therefore to be understood that the present invention can be practiced other than as specifically described, and should be limited in breadth and scope only by the Claims.

I claim:

1. A method comprising the steps of:
a) providing a spectroscopic rotating compensator material system investigation system comprising a source of a polychromatic beam of electromagnetic radiation, a polarizer, a stage for supporting a material system, an analyzer, a dispersive optics and at least one detector system which contains a multiplicity of detector elements, said spectroscopic rotating compensator material system investigation system further comprising at least one compensator positioned at a location selected from the group consisting of:
  before said stage for supporting a material system;
  after said stage for supporting a material system; and
  both before and after said stage for supporting a material system;
such that when said spectroscopic rotating compensator material system investigation system is used to investigate a material system present on said stage for supporting a material system, said analyzer and polarizer are maintained essentially fixed in position and at least one of said at least one compensator(s) is caused to continuously rotate while a polychromatic beam of electromagnetic radiation produced by said source of a polychromatic beam of electromagnetic radiation is caused to pass through said polarizer and said compensator(s), said polychromatic beam of electromagnetic radiation being also caused to interact with said material system, pass through said analyzer and interact with said dispersive optics such that a multiplicity of essentially single wavelengths are caused to simultaneously enter a corresponding multiplicity of detector elements in said at least one detector system;
said spectroscopic rotating compensator material system investigation system further comprising an environmental control chamber in which said spectroscopic rotating compensator material system investigation system is functionally contained, said environmental control chamber being characterized by a selection from the group consisting of:
  it comprises at least one chamber region in which is present polarization state generator (PSG) comprising component(s) prior to said material system and polarization state detector (PSD) comprising component(s) after said material system, and optionally also contains said material system (MS);
  it comprises three chamber regions, in one of which is present polarization state generator comprising component(s) prior to said material system, in the second of which is present the material system and in the third of which is present polarization state detector comprising component(s) after said material system;
  it comprises at least two chamber regions, in one of which is present polarization state generator comprising component(s) prior to said material system and in addition to said material system, and in the second of which is present polarization state detector comprising component(s) present after said material system;
  it comprises at least two chamber regions, in one of which is present polarization state generator comprising component(s) prior to said material system, and in the second of which is present polarization state detector comprising component(s) after said material system in addition to said material system;
b) placing a material system on said stage for supporting a material system and at least partially purging or evacuating said environmental control chamber;
c) causing said source of polychromatic beam of electromagnetic radiation to provide a polychromatic beam of electromagnetic radiation and causing said beam to interact with said material system on said stage for supporting a material system, and interact with said dispersive optics such that a multiplicity of essentially single wavelengths are caused to simultaneously enter a corresponding multiplicity of detector elements in said at least one detector system; and
d) providing a concrete and tangible effect by applying at least one signal developed by at least one of said detector elements, by practicing at least one selection from the group consisting of:
  storing at least some data provided by said data detector in machine readable media;
  analyzing at least some of the data provided by said data detector and storing at least some of the results of said analysis in machine readable media;
  displaying at least some data provided by said data detector by electronic and/or non-electronic means;
  analyzing at least some of the data provided by said data detector and displaying at least some of the results of said analysis by electronic and/or non-electronic means;
  causing at least some data provided by said data detector to produce a signal which is applied to provide a concrete and tangible result;
  analyzing at least some of the data provided by said data detector and causing at least some thereof to produce a signal which is applied to provide a concrete and tangible result.

2. A spectroscopic rotating compensator material system investigation system comprising a source of a polychromatic beam of electromagnetic radiation, a polarizer, a stage for supporting a material system, an analyzer, a dispersive optics and at least one detector system which contains a multiplicity of detector elements, said spectroscopic rotating compensator material system investigation system further comprising at least one compensator positioned at a location selected from the group consisting of:
  before said stage for supporting a material system;
  after said stage for supporting a material system; and
  both before and after said stage for supporting a material system;
such that when said spectroscopic rotating compensator material system investigation system is used to investigate a material system present on said stage for supporting a material system, said analyzer and polarizer are maintained essentially fixed in position and at least one of said at least one compensator(s) is caused to continuously rotate while a polychromatic beam of electromagnetic radiation produced by said source of a polychromatic beam of electromagnetic radiation is caused to pass through said polarizer and said compensator(s), said polychromatic beam of electromagnetic radiation being also caused to interact with said material system, pass through said analyzer and interact with said dispersive optics such that a multiplicity of essentially single wavelengths are caused to simultaneously enter a corresponding multiplicity of detector elements in said at least one detector system;
said spectroscopic rotating compensator material system investigation system further comprising an environmental control chamber in which said spectroscopic rotating compensator material system investigation system is functionally contained, said environmental control chamber being characterized by a selection from the group consisting of:
  it comprises at least one chamber region in which is present polarization state generator (PSG) comprising component(s) prior to said material system and polarization state detector (PSD) comprising component(s) after said material system, and optionally also contains said material system (MS);

it comprises three chamber regions, in one of which is present polarization state generator comprising component(s) prior to said material system, in the second of which is present the material system and in the third of which is present polarization state detector comprising component(s) after said material system;

it comprises at least two chamber regions, in one of which is present polarization state generator comprising component(s) prior to said material system and in addition to said material system, and in the second of which is present polarization state detector comprising component(s) present after said material system;

it comprises at least two chamber regions, in one of which is present polarization state generator comprising component(s) prior to said material system, and in the second of which is present polarization state detector comprising component(s) after said material system and in addition to said material system.

* * * * *